US012753180B2

(12) United States Patent
Zhou et al.

(10) Patent No.: US 12,753,180 B2

(45) Date of Patent: Oct. 6, 2026

(54) Sirt6 ACTIVATORS

(71) Applicant: The Board of Regents of The University of Texas System, Austin, TX (US)

(72) Inventors: Jia Zhou, Galveston, TX (US); Wenbo Zhang, Galveston, TX (US); Hua Liu, Galveston, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 237 days.

(21) Appl. No.: 18/471,912

(22) Filed: Sep. 21, 2023

(65) Prior Publication Data

US 2024/0327411 A1 Oct. 3, 2024

Related U.S. Application Data

(60) Provisional application No. 63/427,435, filed on Nov. 22, 2022.

(51) Int. Cl.

| | |
|---|---|
| ***C07D 487/04*** | (2006.01) |
| ***A61K 31/4985*** | (2006.01) |
| ***A61K 31/5377*** | (2006.01) |
| ***A61K 31/5383*** | (2006.01) |
| ***A61K 31/541*** | (2006.01) |
| ***A61K 31/551*** | (2006.01) |
| ***C07D 498/04*** | (2006.01) |
| ***C07D 519/00*** | (2006.01) |

(52) U.S. Cl.

CPC ........ *C07D 487/04* (2013.01); *A61K 31/4985* (2013.01); *A61K 31/5377* (2013.01); *A61K 31/5383* (2013.01); *A61K 31/541* (2013.01); *A61K 31/551* (2013.01); *C07D 498/04* (2013.01); *C07D 519/00* (2013.01)

(58) Field of Classification Search

None

See application file for complete search history.

(56) References Cited

PUBLICATIONS

Budke et al (ChemMedChem 14:1031-1040, 2019) (Year: 2019).*

Williams et al (Foye's Principles of Medicinal Chemistry, 5th Edition, pp. 59-63, 2002) (Year: 2002).*

* cited by examiner

*Primary Examiner* — Craig D Ricci

(74) *Attorney, Agent, or Firm* — HYLTON-RODIC LAW PLLC

(57) ABSTRACT

The present invention relates to novel small molecule activators of Sirt6, for example, compounds of the general Formula (I), their methods and use for the treatment of various human diseases such as cancer, inflammatory diseases, neurodegenerative diseases, and infectious diseases:

Formula (I)

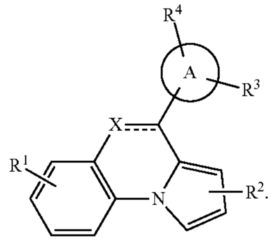

10 Claims, 8 Drawing Sheets

1 (Myristic acid)

2 (Oleoylethanolamide)

3 (Cyanidin)

4 (UBCS039)

5 (CL5D)

6 (MDL-800), R = COOMe 7 (MDL-811), R =

8

Figure 1:
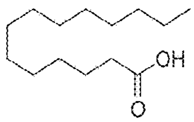
Figure 1:
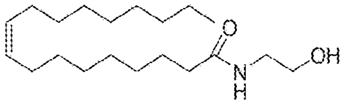
Figure 1:
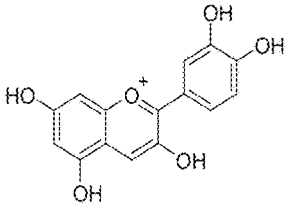
Figure 1:
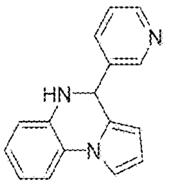
Figure 1:
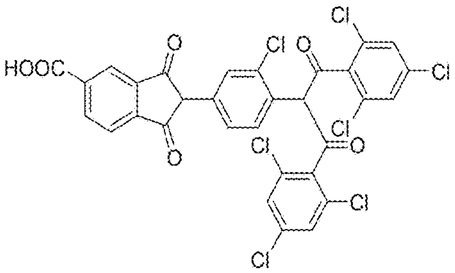
Figure 1:
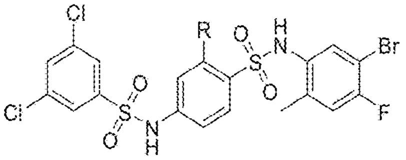
Figure 1:
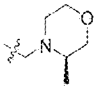
Figure 1:
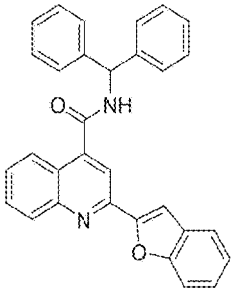

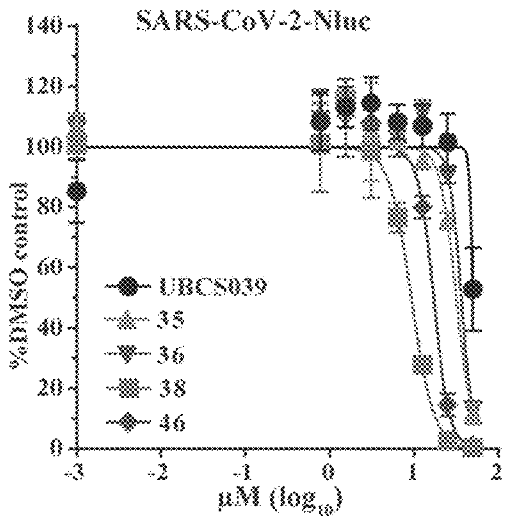
FIG. 8A
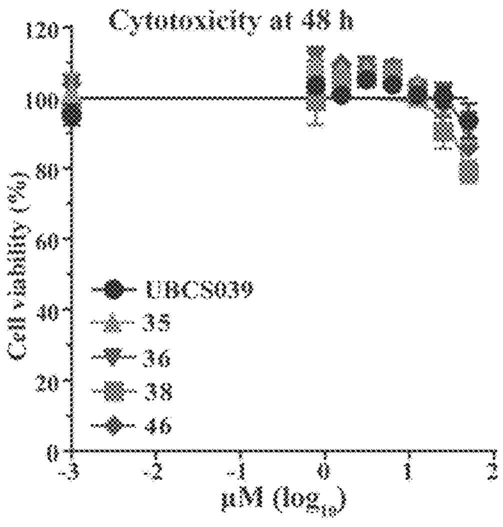
FIG. 8B
| Compound | UBCS039 | 35 | 36 | 38 | 46 |
|---|---|---|---|---|---|
| $EC_{50}$ | 50 | 32.1 | 36.7 | 9.3 | 17.1 |
| $CC_{50}$ | >50 | >50 | >50 | >50 | >50 |
FIG. 8C

Sirt6 ACTIVATORS

CROSS REFERENCE TO RELATED APPLICATIONS

This application claims the benefit of the filing date of U.S. Application No. 63/427,435, filed Nov. 22, 2022, the contents of which are hereby incorporated by reference in their entirety.

STATEMENT OF FEDERALLY SPONSORED RESEARCH AND DEVELOPMENT

This invention was made with government support under NIH Grant No. EY031054 awarded by the National Institutes of Health (NIH). The government has certain rights in the invention.

FIELD OF THE INVENTION

The field of the invention relates generally to activation of sirtuin (Sirt) enzymes for the treatment of human diseases. More specifically, the invention relates to small molecule activators of Sirt6.

DESCRIPTION

1.1 Definitions

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated invention, and further applications of the principles of the invention as illustrated therein are herein contemplated as would normally occur to one skilled in the art to which the invention relates.

Unless defined otherwise, all technical and scientific terms used herein have the same meaning as commonly understood by one of ordinary skill in the art to which this invention pertains.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

The use of "or" means "and/or" unless stated otherwise.

The use of "a" herein means "one or more" unless stated otherwise or where the use of "one or more" is clearly inappropriate.

The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" refers to a ±10% variation from the nominal value. It is to be understood that such a variation is always included in any given value provided herein, whether or not it is specifically referred to.

The term "pharmaceutically acceptable salt" refers to those salts of the compounds of the present invention which are, within the scope of sound medical judgment, suitable for use in contact with the tissues of patients without undue toxicity, and the like. As used herein, the term "pharmaceutically acceptable salt" may include acetate, hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. (See S. M. Barge et al., "Pharmaceutical Salts," J. Pharm. Sci., 66:1-19 (1977), which is incorporated herein by reference in its entirety, for further examples of pharmaceutically acceptable salt).

The term "HBTU" refers to 3-[Bis(dimethylamino)methyliumyl]-3H-benzotriazol-1-oxide hexafluorophosphate (also known as 2-(1H-benzotriazol-1-yl)-1,1,3,3-tetramethyluronium hexafluorophosphate).

The term "HOBt" refers the following structure, known as 1-hydroxybenzotriazole, (including hydrates and polymorphs, thereof):

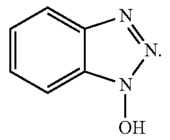

The term "DIEA" refers to N,N-Diisopropylethylamine (also known as Hünig's base, DIPEA, and ethyldiisopropylamine).

The term "DCM" refers to dichloromethane (also known as methylene chloride).

The term "TFA" refers to trifluoroacetic acid.

The term "rt" refers to room temperature.

The term "alkyl" as used herein by itself or as part of another group refers to both straight and branched chain radicals, and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The term "alkyl" may include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, and N. The heteroatom(s) may be placed at any interior position of the heteroalkyl group or at the position at which the alkyl group is attached to the remainder of the molecule. Up to two heteroatoms may be consecutive.

The term "alkylene" as used herein refers to straight and branched chain alkyl linking groups, i.e., an alkyl group that links one group to another group in a molecule. In some embodiments, the term "alkylene" may include $—(CH_2)—$ where n is 2-8.

The term "aryl" means a polyunsaturated hydrocarbon substituent. Aryl groups can be monocyclic or polycyclic (e.g., 2 to 3 rings that are fused together or linked covalently). Non-limiting examples of aryl and heteroaryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

The term "heteroaryl" as used herein refers to groups having 5 to 14 ring atoms; 6, 10 or 14 7π-electrons shared in a cyclic array; and containing carbon atoms and 1, 2 or 3 oxygen, nitrogen or sulfur heteroatoms. A heteroaryl group can be attached to the remainder of the molecule through a carbon or heteroatom. Especially preferred heteroaryl groups include 1,2,3-triazole, 1,2,4-triazole, 5-amino 1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, 2-aminopyridine, 4-aminopyridine, 2-aminoimidazoline, and 4-aminoimidazoline.

An "amino" group refers to an —$NH_2$ group.

An "amido" group refers to an —$CONH_2$ group. An alkylamido group refers to an —CONHR group wherein R is as defined above. A dialkylamido group refers to an —CONRR' group wherein R and R' are as defined above.

The term "halogen" or "halo" as used herein by itself or as part of another group refers to chlorine, bromine, fluorine or iodine.

The term "hydroxy" or "hydroxyl" as used herein by itself or as part of another group refers to an OH group.

An "alkoxy" group refers to an —O-alkyl group wherein "alkyl" is as defined above. In one embodiment, the alkyl group has 1-12 carbons. In another embodiment, the alkyl group has 1-7 carbons. In a further embodiment, the alkyl group has 1-6 carbons. In another embodiment, the alkyl group has 1-4 carbons.

A "thio" group refers to an —SH group.

An "alkylthio" group refers to an —SR group wherein R is alkyl as defined above.

The term "heterocycle" or "heterocyclic ring", as used herein except where noted, represents a stable 5- to 7-membered monocyclic-, or stable 7- to 11-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Rings may contain one oxygen or sulfur, one to three nitrogen atoms, or one oxygen or sulfur combined with one or two nitrogen atoms. The heterocyclic ring may be attached at any heteroatom or carbon atom that results in the creation of a stable structure.

The term "alkylamino" as used herein by itself or as part of another group refers to an amino group which is substituted with one alkyl group having from 1 to 6 carbon atoms. The term "dialkylamino" as used herein by itself or as part of another group refers to an amino group which is substituted with two alkyl groups, each having from 1 to 6 carbon atoms.

The term "arylamine" or "arylamino" as used herein by itself or as part of another group refers to an amino group which is substituted with an aryl group, as defined above.

As used herein, the term "arylalkyl" denotes an alkyl group substituted with an aryl group, for example, Ph-$CH_2$— etc.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, alkyl, heteroalkyl, alkoxy, alkylthio, alkylamino, $(alkyl)_2$amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl (—$C(O)NR_2$), unsubstituted alkyl, unsubstituted heteroalkyl, alkoxy, alkylthio, alkylamino, $(alkyl)_2$amino, alkylsulfinyl, alkyl sulfonyl, aryl sulfonyl, unsubstituted cycloalkyl, unsubstituted heterocyclyl, unsubstituted aryl, or unsubstituted heteroaryl. Exemplary optional substituents include, but are not limited to: —OH, oxo (=O), —Cl, —F, —Br, $C_{1-4}$alkyl, phenyl, benzyl, —$NH_2$, —NH($C_{1-4}$alkyl), —N(C1-4alkyl)$_2$, —NO2, —S($C_{1-4}$alkyl), —$SO_2$($C_{1-4}$alkyl), —$CO_2$($C_{1-4}$alkyl), and —O($C_{1-4}$ alkyl).

A "therapeutically effective amount" is an amount sufficient to decrease, prevent or ameliorate the symptoms associated with a medical condition.

The phrase "effective amount" or "therapeutically effective amount" as used herein refers to an amount necessary (at dosages and for periods of time and for the means of administration) to achieve the desired therapeutic result. An effective amount is at least the minimal amount, but less than a toxic amount, of an active agent which is necessary to impart therapeutic benefit to a subject.

As used herein, the terms "cell" and "cells" refer to any types of cells from any animal, such as, without limitation, rat, mice, monkey, and human.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

1.2 Abbreviations

Sirt, sirtuin; NAD, nicotinamide adenine dinucleotide; OA, osteoarthritis; HCC, hepatocellular carcinoma; CRC, colorectal cancer; SAR, structure-activity relationship; HDAC, histone deacetylase; PDAC, pancreatic ductal adenocarcinoma; HEK, human embryonic kidney; SARS-CoV-2, severe acute respiratory syndrome coronavirus 2; COVID-19, coronavirus disease 2019; LPS, lipopolysaccharide.

1.3 Brief Description of Drawings

FIG. 1: FIG. 1 displays a few representative Sirt6 activators.

Figure 2A:
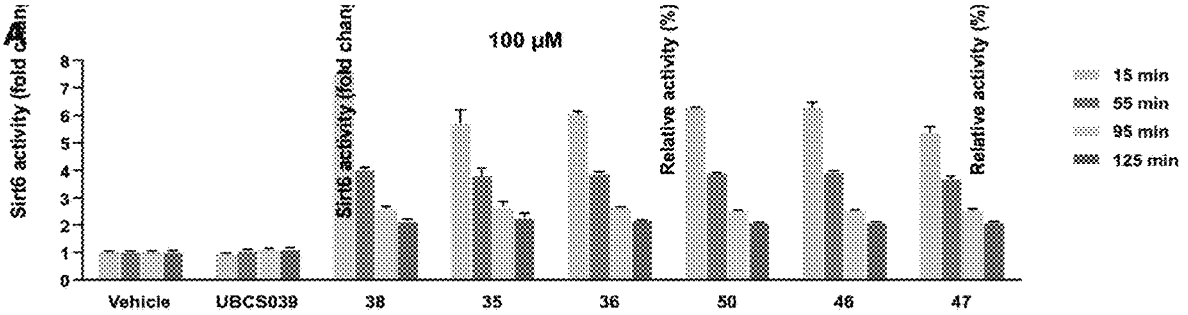
Figure 2B:
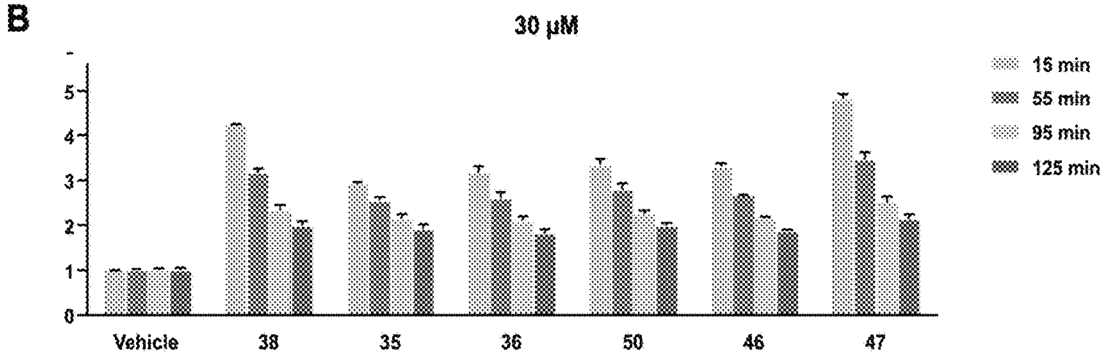
Figure 2C:
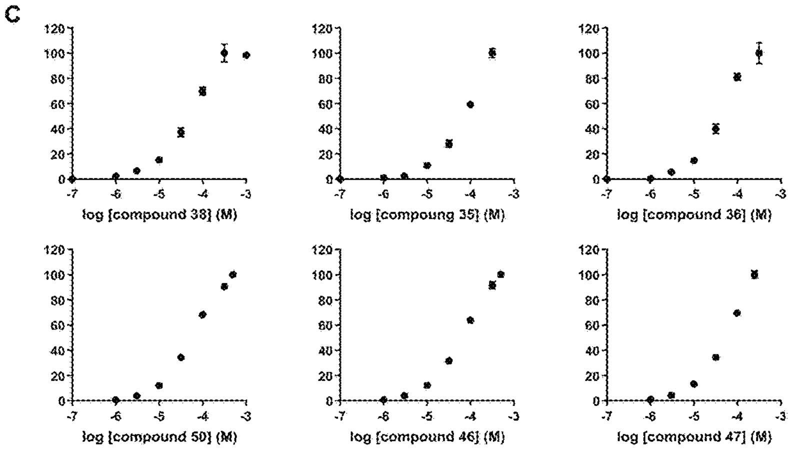

FIGS. 2A-2C: FIGS. 2A-2C display the effect of selected compounds on Sirt6 activities. FIGS. 2A and 2B show the Sirt6 activities of lead compound UBCS039 and six selected compounds: 35, 36, 38, 46, 47, and 50, which were assessed by the Sirt6 Activity Assay Kit at 100 μM and 30 μM at indicated time points. FIG. 2C displays the concentration-response curves of compounds 35, 36, 38, 46, 47, and 50 for Sirt6 activities. Data were presented as mean±SEM. Experiments were repeated at least twice.

Figure 3A:
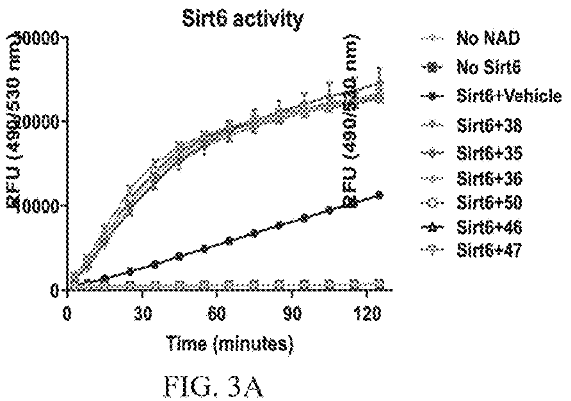
Figure 3B:
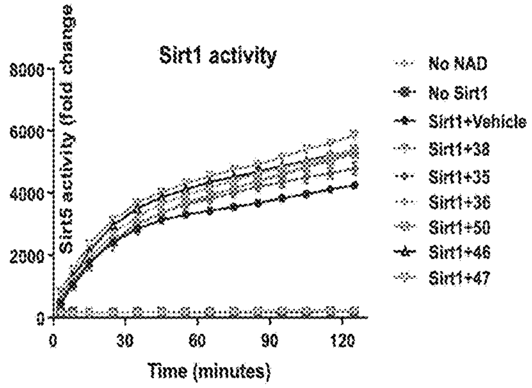
Figure 3C:
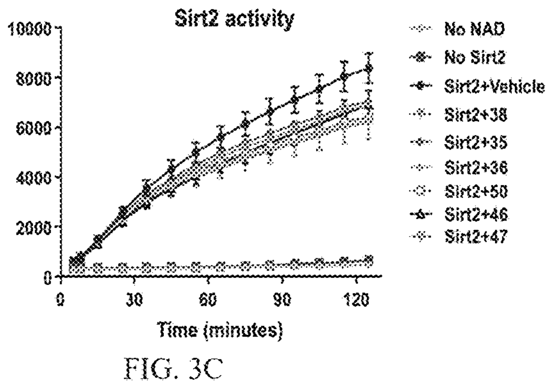
Figure 3D:
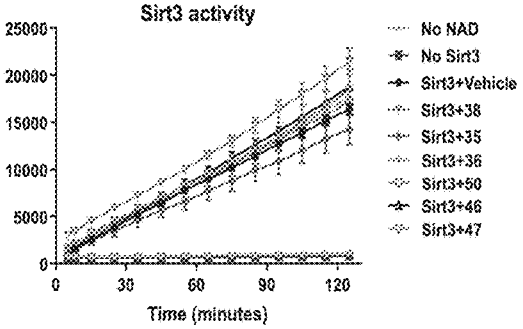
Figure 3E:
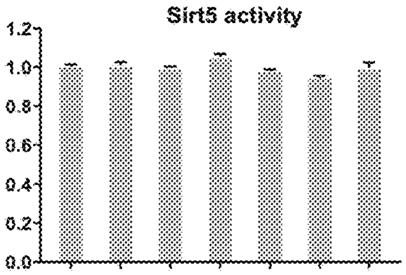

FIGS. 3A-3E: FIGS. 3A-3E display the effects of selected compounds on Sirt1, Sirt2, Sirt3, Sirt5 and Sirt6 activities. FIGS. 3A-3D show the time courses of Sirt6, Sirt1, Sirt2 and Sirt3 deacetylation activities in response of selected compounds. FIG. 3E shows the fold change of Sirt5 desuccinylation activity in response of selected compounds. Data were presented as mean±SEM. Experiments were performed at least twice.

Figure 4A:
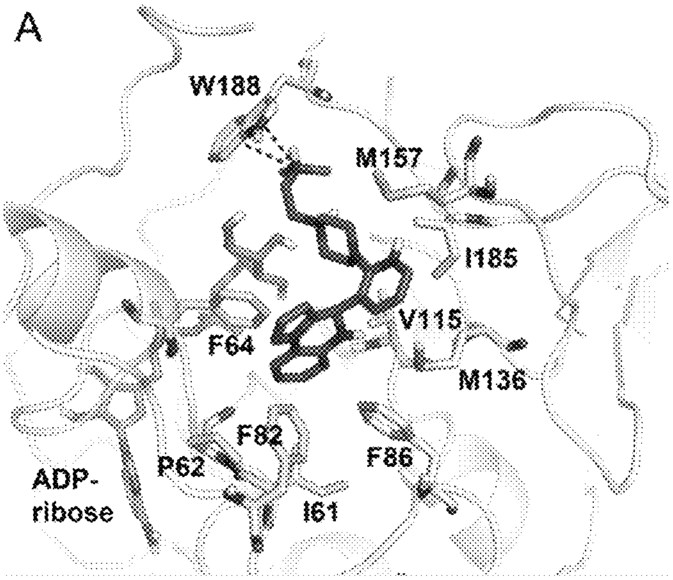
Figure 4B:
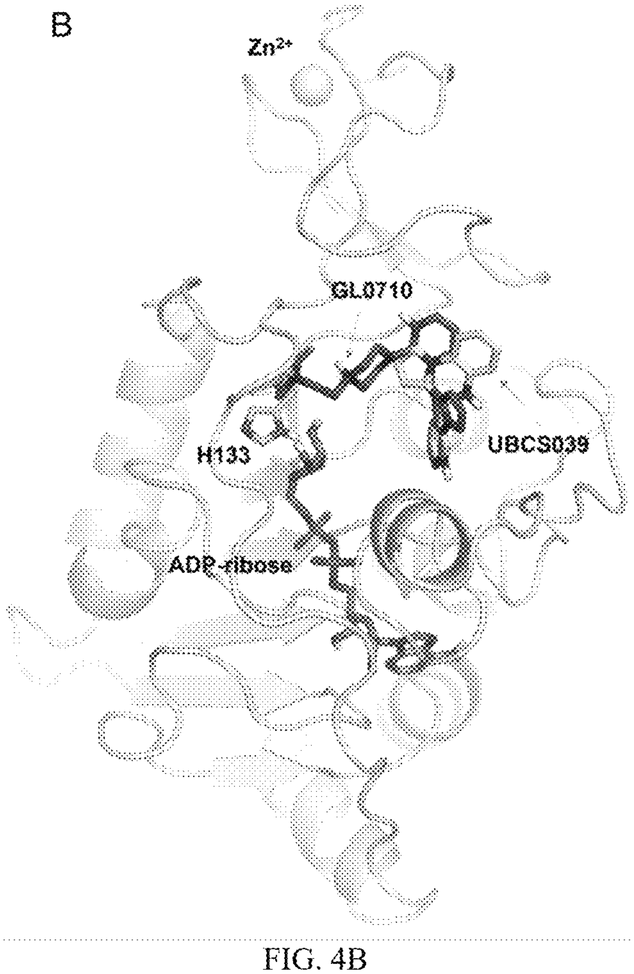

FIGS. 4A-4B: FIGS. 4A-4B display the docking analysis of compound 38 (GL0710) with Sirt6 protein. FIG. 4A shows GL0710 (magenta sticks) docked into Sirt6/ADP ribose structure (PDB ID: 5MF6). ADP-ribose is shown as orange sticks and binding site residues are shown as gray sticks. π-cation interaction is shown as blue dashed lines. FIG. 4B shows the overlay of Sirt6/ADP ribose/UBCS039 complex with GL0710 docked pose (GL0710 in magenta sticks, UBCS039 in yellow sticks, and ADP ribose in orange sticks). The catalytic residue H133 indicates the active site.

Figure 5A:
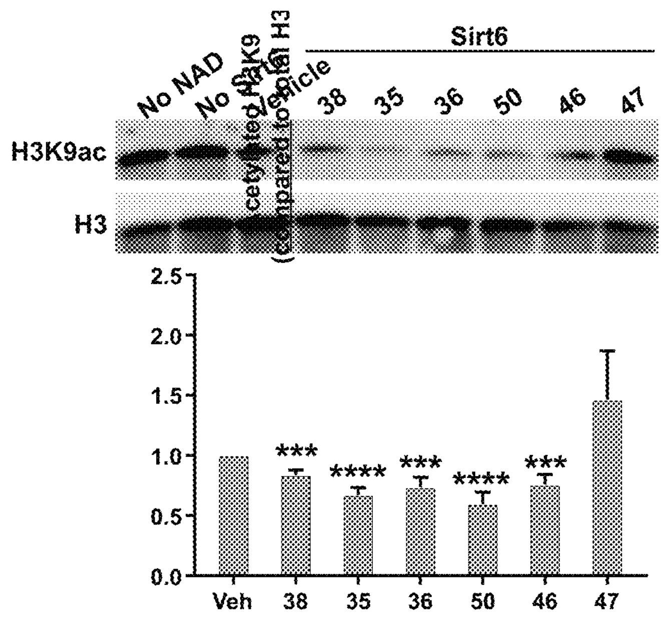
Figure 5B:
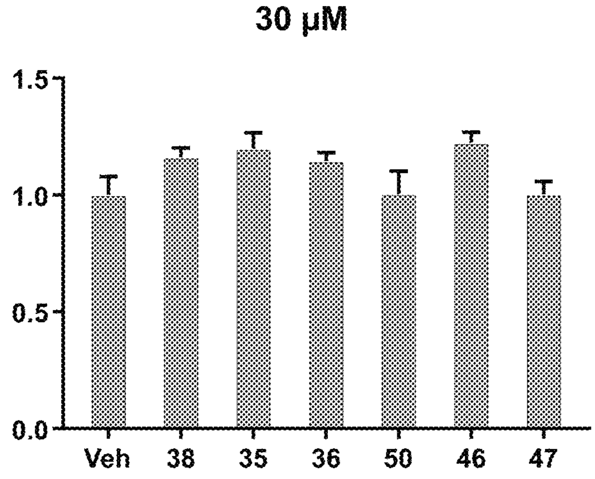
Figure 5C:
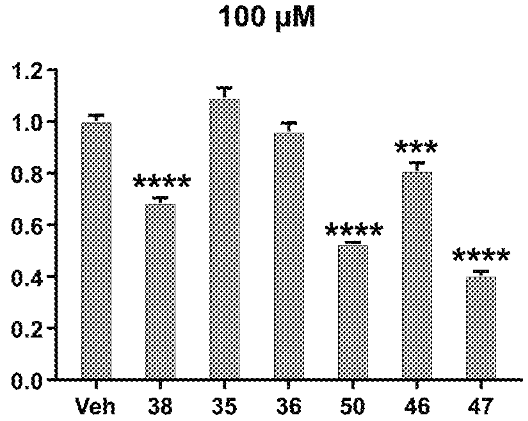

FIGS. 5A-5C: FIGS. 5A-5C display the deacetylation effect and cytotoxicity of selected compounds. FIG. 5A shows the deacetylation effects on H3K9 of six selected compounds which were detected in nucleosomes. Nucleosomes extracted from HEK293T cells were incubated with 100 μM of selected compounds or Vehicle at 30° C. for 60 minutes. Acetylated H3K9 and total H3 were detected by Western blot. The level of acetylated H3K9 was quantified by Image Lab software. FIGS. 5B and 5C show the cell viability which was assessed by MTT assay. R28 cells were treated with 30 μM or 100 μM compounds for 24 hours. Data were presented as mean±SEM. The experiment was repeated at least three times. *$p<0.001$; **$p<0.0001$.

Figure 6A:
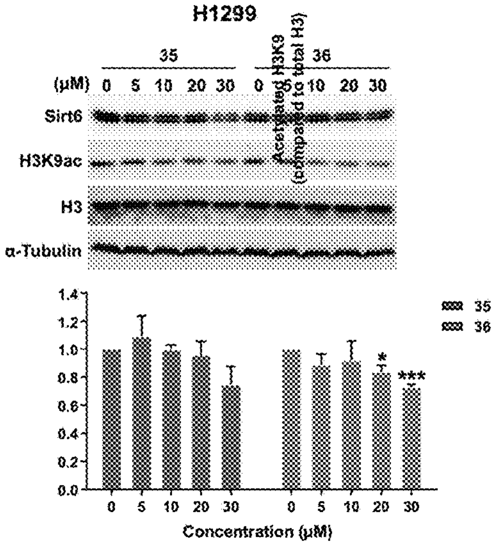
Figure 6B:
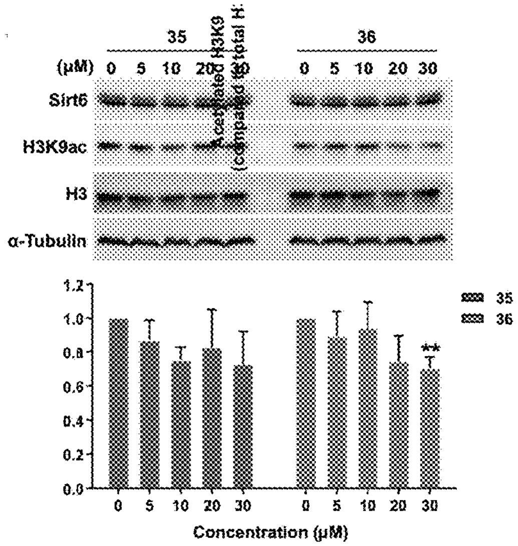
Figure 6C:
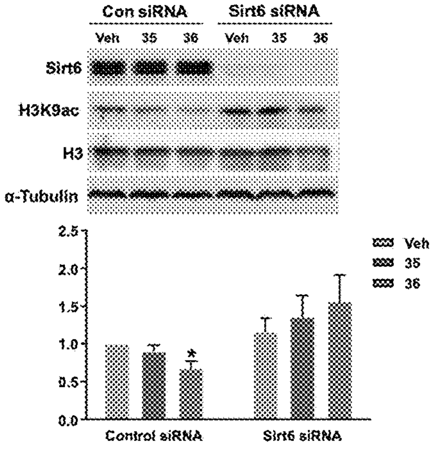
Figure 6D:
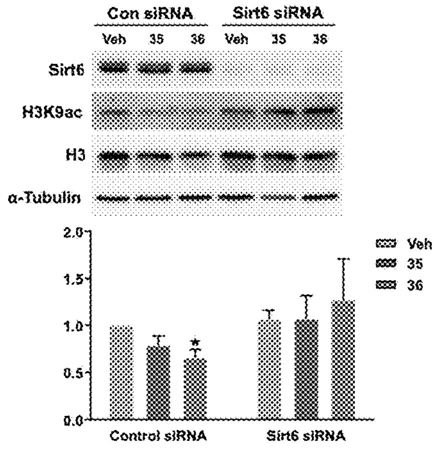
Figure 6E:
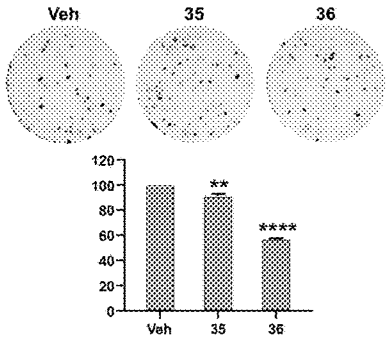
Figure 6F:
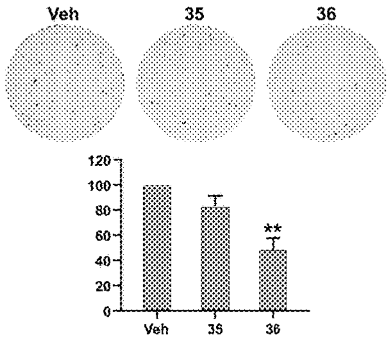

FIGS. 6A-6F: FIGS. 6A-6F display the deacetylation effects of compounds 35 and 36 in cancer cells. FIGS. 6A and 6B show that H1299 and PLC/PRF/5 cells were treated with compounds 35 and 36 at indicated concentrations for 24 hours, and the expression of Sirt6, acetylated H3K9, and total H3 was detected by Western blot and quantified. FIGS. 6C and 6D show that H1299 and PLC/PRF/5 cells were transfected with control or Sirt6 siRNA, followed by the treatment with 30 μM compounds 35 and 36 for 24 hours. The expression of Sirt6, acetylated H3K9, and total H3 was detected by Western blot and quantified. FIGS. 6E and 6F show that the colony formation assay was performed in H1299 and PLC/PRF/5 cells which were exposed to 30 μM compounds 35 and 36 or Vehicle for one week. Colony formation was calculated as the ratio of the area by colonies to total plate area using Image J. All experiments were repeated three times. Data are presented as mean±SEM. *$p<0.05$, $p<0.01$, *$p<0.001$ compared to relevant controls.

Figure 7A:
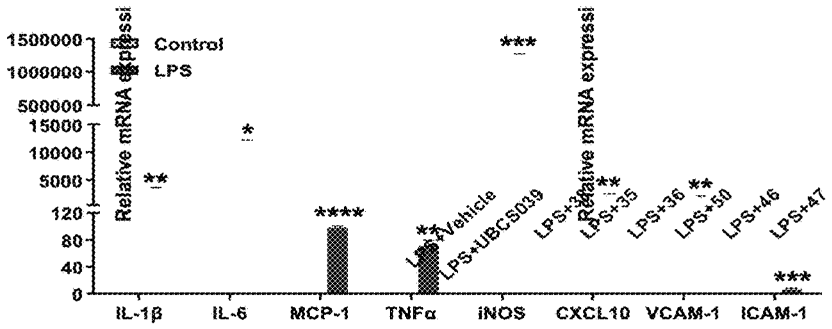
Figure 7B:
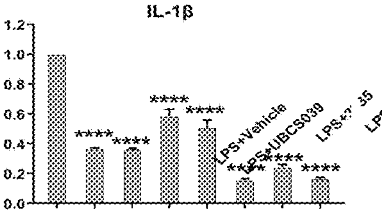
Figure 7C:
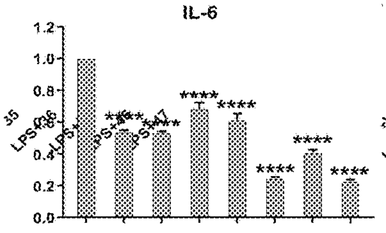
Figure 7D:
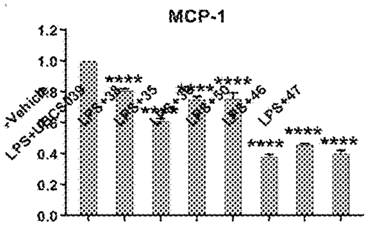
Figure 7E:
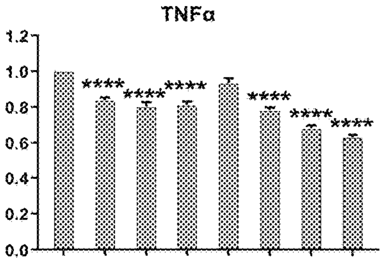
Figure 7F:
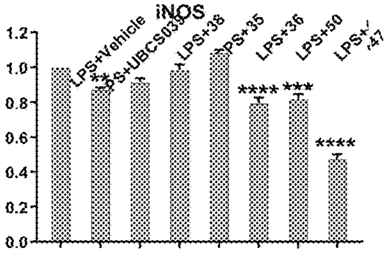
Figure 7G:
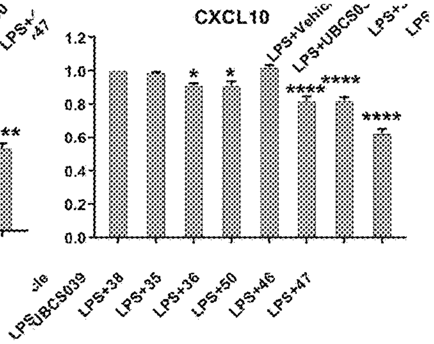

FIGS. 7A-7I: FIGS. 7A-7I display the anti-inflammatory effects of the selected compounds. FIG. 7A shows that inflammatory genes were induced by LPS stimulation in BV2 cells. FIGS. 7B to 7I show that BV2 cells were pretreated with 30 μM selected compounds or Vehicle and followed by 100 ng/mL LPS for 6 hours. The mRNA expression of inflammatory genes was examined by q-PCR. Data were presented as mean±SEM. The experiment was repeated three times. *$p<0.05$; $p<0.01$; *$p<0.001$; ****$p<0.0001$.

FIGS. 8A-8C: FIGS. 8A-8C display the antiviral activities of selected compounds against SARS-CoV-2. FIG. 8A shows dose-dependent inhibition of SARS-CoV-2-Nluc by selected compounds. FIG. 8B shows the cell viability assay. A549-hACE2 cells were incubated with various concentrations of selected compounds and then assayed for viability at 48 h post-incubation. FIG. 8C shows the summary of $EC_{50}$ and $CC_{50}$ of selected compounds.

1.4 SIRTUIM (SIRT) FAMILY DESCRIPTION

The sirtuin (Sirt) family is a class of enzymes that possess $NAD^+$-dependent either deacylase or mono-ADP-ribosyltransferase activity, regulating many cellular processes such as energy metabolism, stress responses, and genomic stability [1-4]. Currently, there are seven mammalian sirtuins (Sirt1-7), characterized by a highly conserved catalytic core, but differing in their cellular localization and substrate preferences [5-7]. Of these members, Sirt6 specifically catalyzes the deacetylation of $N^{\varepsilon}$-acetyl-lysines 9, 18, and 56 of histone H3 (H3K9ac, H3K18ac, and H3K56ac, respectively) and associates with chromatin to modulate DNA repair, gene expression, and telomeric maintenance [8-13]. In addition, Sirt6 can hydrolyze long-chain acylated substrates and catalyze mono-ADP-ribosylation [14, 15]. Sirt6 knockout mice display smaller body size, shortened lifespan, and aging-associated degenerative phenotypes such as cancers and metabolic defects, while Sirt6 overexpression impairs the development of several cancer types and prolongs the lifespan of male mice [16-19]. It was reported that siRNA-mediated Sirt6-knockdown led to a significant increase in the yield of human cytomegalovirus (HCMV), herpes simplex virus 1 (HSV-1), human adenovirus 5 (HAdV-5), and influenza virus H1N1 in cultured cells, suggesting an antiviral role of Sirt6 [20]. Sirt6 inhibits dengue virus (DENV)-induced proinflammatory cytokine and chemokine production via RIG-I-like receptor (RLR) and Toll-like receptor 3 (TLR3) signaling pathways [21]. Besides, Sirt6 was also found associated with many other human diseases including osteoarthritis (OA), diabetes, heart diseases, neurodegenerative diseases, etc., and its emerging role in a variety of human diseases has been comprehensively reviewed recently by our group [5](see G. Liu, H. Chen, H. Liu, W. Zhang, J. Zhou, Emerging roles of SIRT6 in human diseases and its modulators, Med. Res. Rev., 41 (2021) 1089-1137).

A summary list of human diseases involving Sirt6 includes, for example, a cancer chosen from hepatocellular carcinoma, colon cancer, lung cancer, breast cancer, glioma cancer, bone cancer, or skin cancer. Additional diseases involving Sirt6 can include, for example, Alzheimer's disease, retinopathies, corneal diseases, dengue virus, autoimmune encephalitis, hepatitis virus, nonalcoholic steatosis (NASH), osteoarthritis, Parkinson's disease, rheumatoid arthritis, retinitis pigmentosa, type 2 diabetes mellitus, cardiac hypertrophy, myocardial fibrosis, heart failure, atherosclerosis, myocardial infarction, coronary heart disease, or renal injury.

Thus, targeting Sirt6 activation has been considered a promising approach for the treatment of Sirt6-related human conditions such as cancers, inflammation, viral infections, and aging-related diseases [22].

1.5 Description of Sirt6 Activators

Despite the great clinical application prospect, not many Sirt6 activators have been reported so far [2, 5]. Long-chain fatty acids (containing 14-18 carbons) were found to stimulate Sirt6 deacetylation, represented by myristic acid (1, FIG. 1) which increased the activity of Sirt6 deacetylation up to 10.8-fold, with an $EC_{50}$ value of 246 μM [23]. Oleoylethanolamide (2) is an ethanolamide analog of oleic acid which displayed a 2.1-fold maximum activation ($E_{max}$) on Sirt6 deacetylation with an $EC_{50}$ of 3.1 μM [24]. Flavonoids was found to increase Sirt6 deacetylation activity at high concentrations, and cyanidin (3) showed the most potent activating effect with a 55-fold $E_{max}$ and an $EC_{50}$ of 460 μM [25, 26]. Moreover, cyanidin could ameliorate the aggressive course of OA in surgical destabilization of the medial meniscus mouse models, possibly exerting the protective effect through regulating the Sirt6/NF-κB signaling axis [27]. UBCS039 (4) is the first synthetic Sirt6 activator that increased Sirt6 deacetylation activity in a dose-dependent manner with a ~2-fold $E_{max}$ and an $EC_{50}$ of 38 μM. Meanwhile, it displayed no obvious effects on basal Sirt1, 2, and 3 deacetylation activities [28]. Through activity-based screening and subsequent chemical optimization, CL5D (5) was identified as a potent Sirt6 activator, inducing 4-fold activation at a low concentration of 3 μM [29]. MDL-800 (6), a Sirt6 allosteric activator, increased the deacetylation activity of Sirt6 up to 22-fold with an $EC_{50}$ of 10.3 μM and showed more than 10-fold selectivity over Sirt1-5, Sirt7, and HDAC1-11 [30]. It significantly promoted H3K9 and H3K56 deacetylation dose-dependently in human hepatocellular carcinoma (HCC) cells, consequently inhibited their proliferation through Sirt6-mediated cell cycle arrest, and suppressed HCC tumor growth in mouse xenograft models [30]. Compared to MDL-800, MDL-811 (7) with an extra water-soluble fragment showed improved Sirt6 deacetylation activity ($EC_{50}$=5.3 μM) and bioavailability (F=92.96%) in mice. Notably, MDL-811 displayed broad antiproliferative effects on various colorectal cancer (CRC) cell lines and in vivo anti-tumor efficacy in cell line- and patient-derived xenografts as well as in the $APC^{min/+}$ spontaneous CRC model [31]. The quinoline derivative 8 was reported to activate Sirt6-dependent peptide deacetylation and demyristoylation ($EC_{50}$=5.35 μM and 8.91 μM, respectively) and exhibit weak or no activity against other HDAC family members [32]. In addition, it inhibited the proliferation and migration of pancreatic ductal adenocarcinoma (PDAC) cells, decreased the levels of H3K9ac, H3K18ac, and H3K56ac in PDAC cell lines (PANC-1 and BXPC-3), and significantly suppressed tumor growth in a PDAC tumor xenograft model. However, it has several drawbacks such as limited aqueous solubility, poor absorption, and low oral bioavailability (F=4.24%) [32]. Therefore, it remains an unmet need to develop more effective and selective Sirt6 activators with favorable druglike properties.

Based on the lead compound UBCS039, herein, structure-activity relationship (SAR) studies were explored by introducing a functional hydrophilic side chain at the 2-position of the 3-pyridyl moiety assisted by molecular modeling/docking and identified a series of novel pyrrolo[1,2-a]quinoxaline-based derivatives as potent and selective Sirt6 activators with improved efficacy and low cytotoxicity. The Sirt6-knockdown experiment has further validated the on-target effects of this class of Sirt6 activators. Molecular docking studies indicated that the protonated nitrogen on the side chain of compound 38 forms π-cation interactions with Trp188, further stabilizing it into this extended binding pocket. This functional hydrophilic side chain provided us a useful moiety for designing novel and potent Sirt6 activators with new scaffolds while also tuning their druglike properties such as aqueous solubility. New compounds 35, 36, 38, 46, 47, and 50 strongly repressed lipopolysaccharide (LPS)-induced proinflammatory cytokine/chemokine production, while 38 also significantly suppressed severe acute respiratory syndrome coronavirus 2 (SARS-CoV-2) infection with an $EC_{50}$ value of 9.3 μM, indicating the use of this class of Sirt6 activators as anti-inflammatory and anti-SARS-CoV-2 agents. Moreover, compound 36 significantly inhibited the colony formation of cancer cells. These new molecules may serve as powerful pharmacological tools for elucidating the role of Sirt6 in various human conditions or as therapeutics against such relevant disorders including cancer, inflammation, and infectious diseases.

2. PREPARATION OF EXEMPLARY NOVEL ACTIVATORS OF SIRT6

2.1. Chemistry

The description of preparation of certain compounds of the invention is meant to be exemplary of certain embodiments of the invention. The reagents and reactant used for synthetic conversions outlined herein and below is merely exemplary. The invention contemplates using the same or different reagents discussed herein to achieve preparation of the compounds of the invention.

The general synthesis of new derivatives with different amino side chains on the pyridine ring is outlined in Scheme 1. Substitution of commercially available 2-chloronicotinaldehyde (9) with various amines gave the intermediates 11a-o, and the subsequent condensation of 9 or 11a-o with 2-(1H-pyrrol-1-yl)aniline (10) in the presence of acetic acid in ethanol afforded derivatives 14-29. 2-Fluoronicotinaldehyde (12) was treated with N-Boc-ethanolamine to generate the intermediate 13, which was then coupled with 10, followed by acidic Boc-deprotection, to provide compound 30.

Scheme 1. Synthesis of Compounds 14-30.

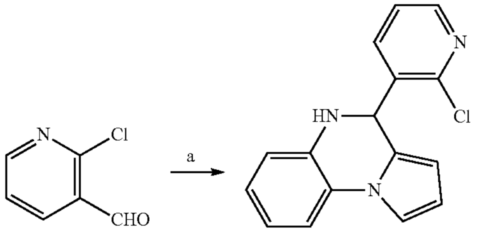

9 14

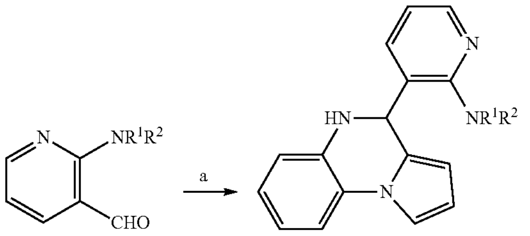

11a-o 15-29

-continued

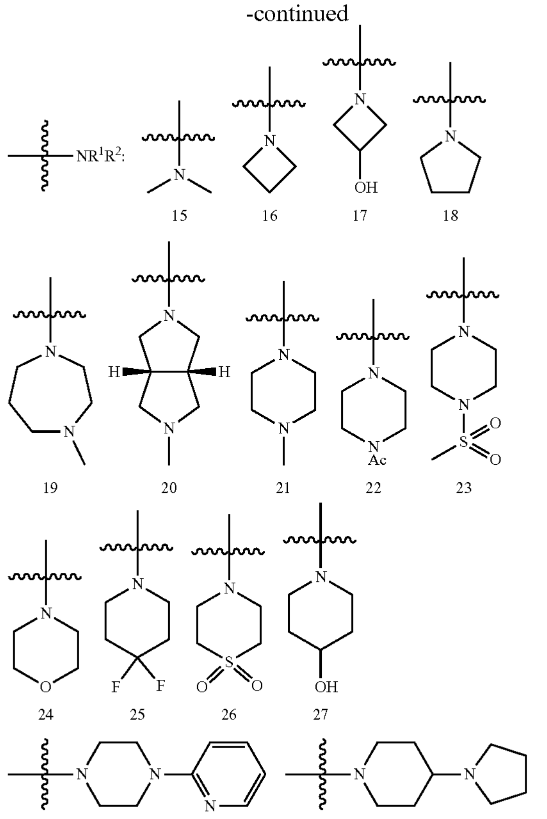

15 16 17 18 19 20 21 22 23 24 25 26 27 28 29

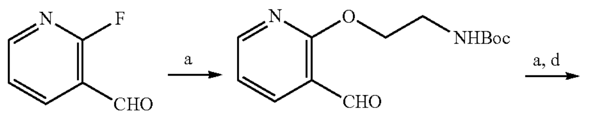

12 13

-continued

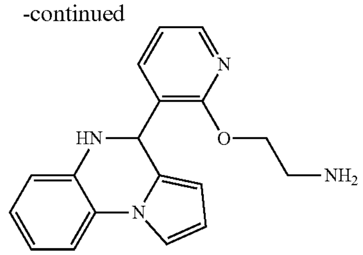

30

Reagents and conditions: (a) 2-(1H-pyrrol-1-yl)aniline (10), EtOH, AcOH, 50° C., 3 h. (b) $NHR^1R^2$, or $NHR^1R^2$ hydrochloride and $K_2CO_3$, toluene or DMF, 100-110° C., overnight. (c) N-Boc-ethanolamine, $Na_2CO_3$, DMF, 110° C., 6 h. (d) TFA, $CH_2Cl_2$, room temperature (RT), 3 h.

Compounds 35-50 with different substituted piperazine moieties were synthesized following similar procedures to that of preparing 14-30 (Scheme 2). Direct substitution of 9 with appropriately substituted piperazines or with piperazine followed by a second substitution with bromide or chloride afforded the key intermediates 32a-i, which were then condensed with 10 to yield new compounds 35-40, 42, 44, and 48. Amide 41 was accessed from nitrile 40 via hydrolysis. Substitution of 42 with dimethylamine produced compound 43. Chlorination of 32a using $SOCl_2$ gave chloride 33, which was then treated with different amines to yield the intermediates 34a-e. Condensation of 34a-e with 10 afforded new derivatives 45-47, 49, and 50, respectively.

Scheme 2. Synthesis of Compounds 35-50.

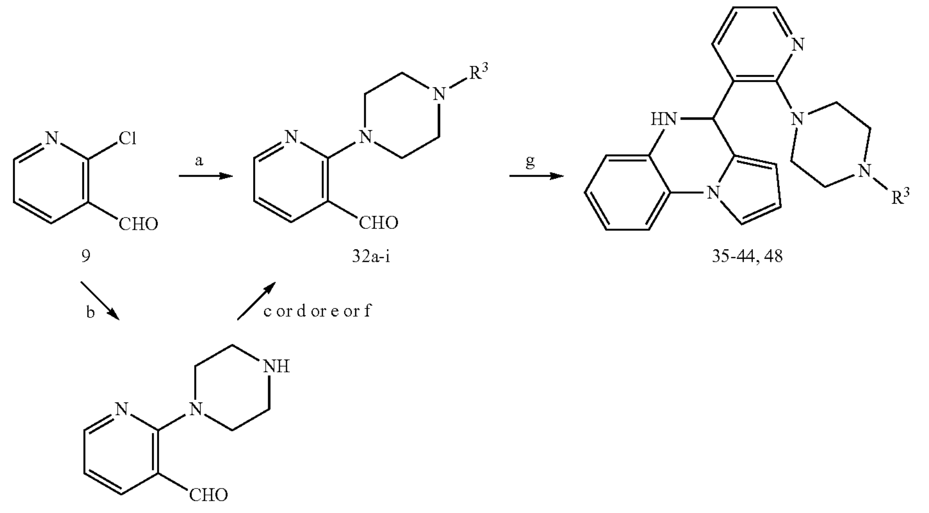

9 32a-i 35-44, 48 31

-continued $R^1$:

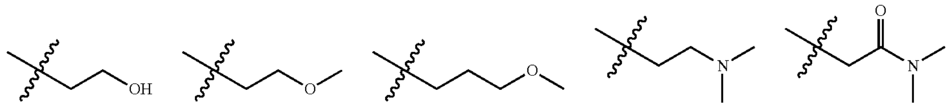

32a, 35 32b, 36 32d, 37 32c, 38 32e, 39

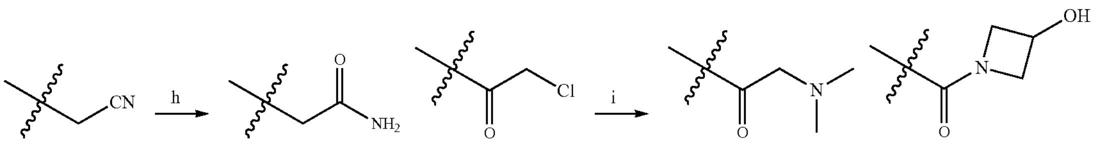

32f, 40 41 32g, 42 43 32h, 44

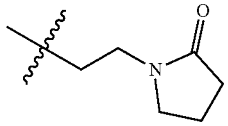

32i, 48

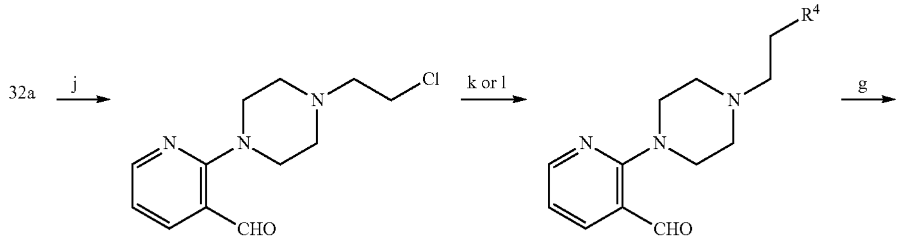

34a-e

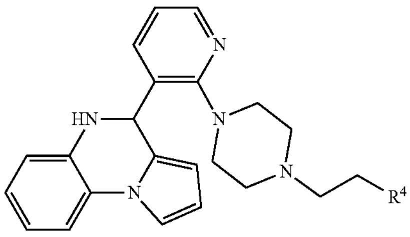

45-47, 49, 50

$R^4$:

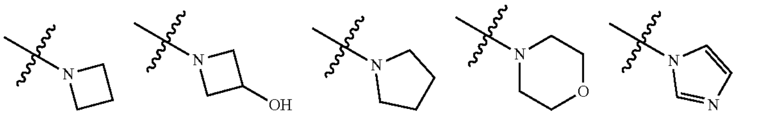

34a, 45 34b, 46 34c, 47 34d, 49 34e, 50

Reagents and conditions: (a) N—$R^3$ substituted piperazine (for compounds 32a-c), toluene, 110° C., 5 h. (b) piperazine, $K_2CO_3$, DMF, 90° C., overnight. (c) $R^3Cl$ or $R^3Br$ (for compounds 32d-f), $K_2CO_3$, $CH_3CN$, 50° C., 3 h. (d) 2-chloroacetyl chloride, $K_2CO_3$, $CH_2Cl_2$, 0° C., 1 h. (e) (1) 4-nitrophenyl chloroformate, $Et_3N$, $CH_2Cl_2$, 0° C., to RT, overnight; (2) 3-hydroxyazetidine hydrochloride, $K_2CO_3$, $CH_3CN$, 60° C., overnight. (f) 1-(2-chloroethyl)pyrrolidin-2-one, $Et_3N$, toluene, 110° C., overnight. (g) 10, EtOH, AcOH, 50° C., 3 h. (h) KOH, t-BuOH, 110° C., 1 h. (i) dimethylamine, $K_2CO_3$, DMF, 50° C., 4 h. (j) $SOCl_2$, $CH_2Cl_2$, 50° C., 2 h. (k) $R^4H$ or $R^4H$ hydrochloride, $Cs_2CO_3$, EtOH, 70° C., 2 h. (l) imidazole, NaOH, TBAB, toluene, RT to 110° C., 6 h.

As described in Scheme 3, the substitution of aldehydes 51a-d with substituted piperazine 52 produced the intermediates 53a-d, which were then converted into compound 60-63 by similar condensations with 2-(1H-pyrrol-1-yl)aniline 10. Acylation of 38 provided compound 64. Compound 65 was formed by a reaction of 32c with 10 and acetic acid in ethanol at a higher temperature of 70° C. overnight. The starting material 54 was treated with 2-methyl-1H-imidazole to give the nitro intermediate 55, which was transformed to 67 via hydrogenation using Pd/C and subsequent condensation with 32c.

Scheme 3. Synthesis of Compounds 60-65 and 67.

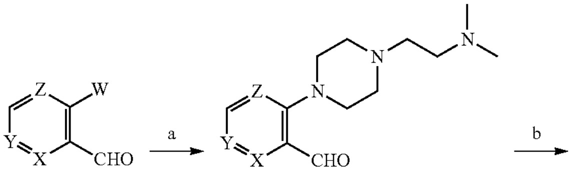

51a-d 53a-d 51a (W = Cl), 53a, 60: X = Z = CH, Y = N 51b (W = Cl), 53b, 61: X = Z = N, Y = CH

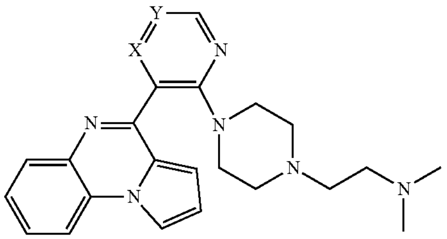

60-63

51c (W = Cl), 53c, 62: X = CH, Y = CCl, Z = N 51d (W = F), 53d, 63: X = Y = Z = CH

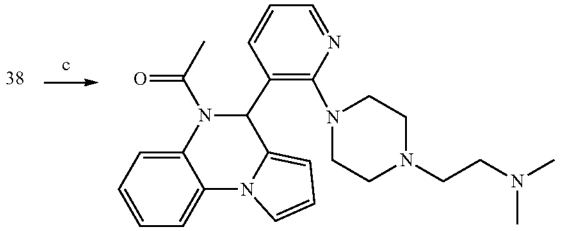

64

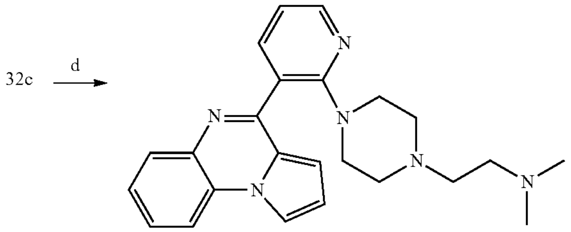

65

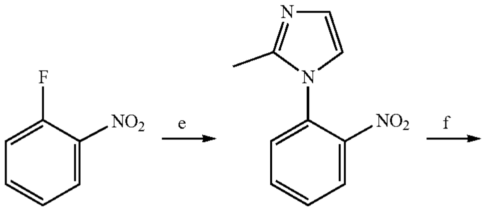

54 55

-continued

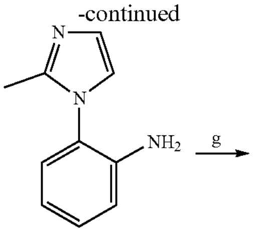

56

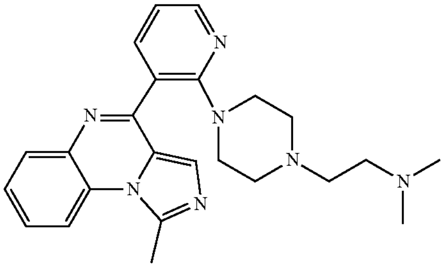

67

Reagents and conditions: (a) 1-(2-dimethylaminoethyl)piperazine (52), toluene (for 53a, c), 110° C., 4 h; or 52, $K_2CO_3$, dioxane (for 53b), reflux, 4 h; or 52, $K_2CO_3$, DMF (for 53d), reflux, 5 h. (b) 10, EtOH, AcOH, 50° C., 3 h. (c) acetyl chloride, $Et_3N$, $CH_2Cl_2$, RT, 30 min. (d) 10, EtOH, AcOH, 70° C., overnight. (e) 2-methyl-1H-imidazole, $K_2CO_3$, $CH_3CN$, reflux, 24 h. (f) Pd/C, $H_2$, EtOH, RT, 4 h. (g) 32c, EtOH, AcOH, 50° C., 3 h.

Compounds 66 and 68-76 were prepared according to the general synthesis outlined in Scheme 4. Treatment of commercially available 2-aminophenols 57a-e with 2,5-dimethoxytetrahydrofuran provided the intermediates 59a-e. The intermediates 59f and 59g were synthesized by hydrolysis of 57e and subsequent condensations with $NH_4Cl$ or 2-aminoethylmethylsulfone. Condensations of 59a-g with 32c produced compounds 66, 68-71, 73, and 74, respectively. Reduction of 71 using $LiAlH_4$ yielded compound 72. Formylation of 66 followed by reduction using $NaBH_4$ afforded compound 75. Compound 76 was synthesized by the reaction of 66 with S-(trifluoromethyl)dibenzothiophenium triflate.

Scheme 4. Synthesis of Compound 66 and 68-76.

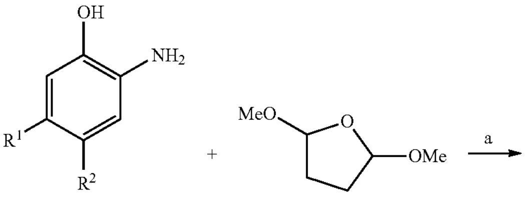

57a-d 58

57a, 59a, 67: $R^1$ = H, $R^2$ = H 57b, 59b, 68: $R^1$ = H, $R^2$ = Me 57c, 59c, 69: $R^1$ = H, $R^2$ = OMe 57d, 59d, 70: $R^1$ = H, $R^2$ = F

-continued

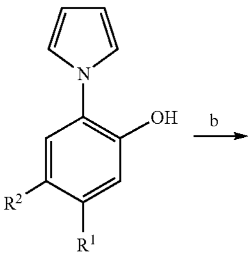

59a-g

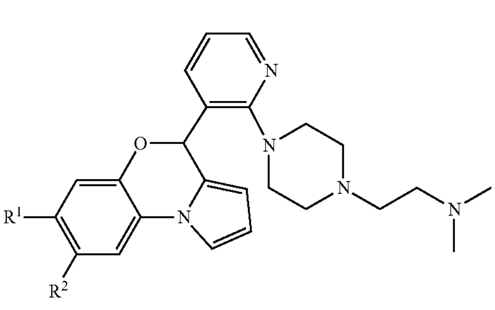

66, 68-74 c
72: $R^1 = CH_2OH$, $R^2 = H$
d
57e, 59e, 71: $R^1 = CO_2Me$, $R^2 = H$
d
59f, 73: $R^1 = CONH_2$, $R^2 = H$ 59g, 74: $R^1$ =

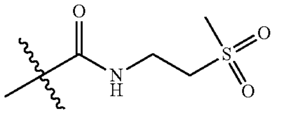

$R^2 = H$

-continued

66

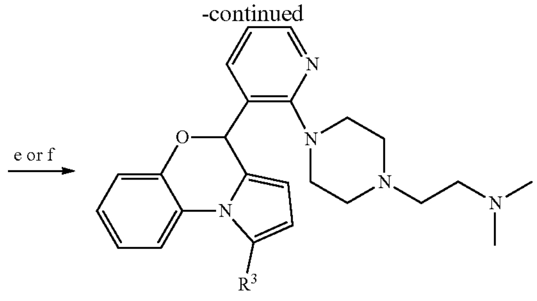

75, 76

75: $R^3 = CH_2OH$

76: $R^3 = CF_3$

Reagents and conditions: (a) AcOH, 110° C., 15 min. (b) 32c, TFA, $CHCl_3$, 60° C., 24 h. (c) $LiAlH_4$, THF, 0° C. to RT, 2 h. (d) (1) LiOH, EtOH, $H_2O$, RT to 50° C., 4 h; (2) $NH_4Cl$ (for 59f) or 2-aminoethylmethylsulfone hydrochloride (for 59g), HATU, $Et_3N$, DMF, RT, overnight. (e) (1) $POCl_3$, DMF, 0° C. to 50° C., overnight; (2) $NaBH_4$, $CH_3OH$, 0 to RT, 1 h. (f) S-(trifluoromethyl)dibenzothiophenium triflate, $K_2CO_3$, DMF, 80° C., 48 h.

2.2. In Vitro Evaluation of Sirt6 Deacetylation Activation

All newly synthesized compounds were first screened by FLUOR DE LYS (FDL) assay at 100 μM [33], and the fold-changes of Sirt6-dependent peptide deacetylation activity were quantified, using the lead compound UBCS039 as the reference control for comparison. The active compounds screened out (activation fold >2) were further evaluated for their activation effects on Sirt6 at 30 μM. Previous studies showed that the 3-pyridyl group of UBCS039 was critical to maintaining its activating activity on Sirt6 and shifting the pyridine nitrogen from the meta to ortho position led to a significant decrease in Sirt6 activation [28]. Starting from the lead compound UBCS039, attempts were made to introduce additional functional groups and side chains at the 2-position of the 3-pyridyl moiety to form potential important interactions between the compound and the Sirt6 protein. As shown in Table 1, inserting 2-Cl (14), 2-dimethylamino (15), 2-(azetidin-1-yl) moieties (16-17), and 2-(pyrrolidin-1-yl) (18) impacted the potency of Sirt6 deacetylation significantly to a small extent, displaying activation folds of 1.04~ 1.47 at 100 μM, compared to UBCS039 (1.12-fold at 100 μM in our assay). Surprisingly, compounds with heterocycles bearing terminal —$NHCH_3$— group (19-21) displayed dramatically enhanced Sirt6 deacetylation activities by more than 4-fold at 100 μM and 2-fold at 30 μM. Among them, 21 with 2-(4-methylpiperazin-1-yl) potently activated Sirt6 deacetylation by 4.62- and 2.44-fold at 100 μM and 30 μM, respectively. Further replacing its terminal methyl with acetyl (22) or methylsulfonyl (23) resulted in a slight decrease in potency with activation folds of 2.74 and 3.63 at 100 μM, respectively. Compound 24 with morpholinyl did not activate Sirt6, while compounds with terminal —$CF_2$— (25), —$SO_2$— (26), and —CHOH— (27) exhibited decreased activating effects of ~2-fold at 100 μM, in comparison with compound 21. Substituting the terminal methyl (21) with pyridin-2-yl (28) also led to a significant loss in activation potency. Interestingly, compound 29 with 4-(pyrrolidin-1-yl)piperidin-1-yl moiety showed obvious Sirt6 deacetylation activity with 3.44-fold at 100 μM. The short side chain of 2-aminoethoxy (30) was not tolerated at the 2-position of the 3-pyridyl moiety.

TABLE 1

Effect of Compounds 14-30 on Sirt6-dependent Peptide Deacetylation Activation[a]

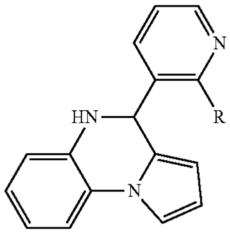

| Entry | R | Activation Fold[a] 100 μM | 30 μM | Entry | R | Activation Fold 100 μM | 30 μM |
|---|---|---|---|---|---|---|---|
| UBCS039 | H | 1.12 ± 0.08 | NT[b] | 22 | 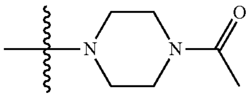 [SMILES: *N1CCN(C(C)=O)CC1] | 2.74 ± 0.10 | 1.60 ± 0.01 |
| 14 | 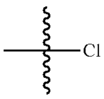 | 1.04 ± 0.02 | NT | 23 | 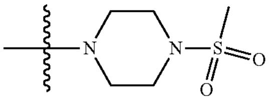 [SMILES: *N1CCN(S(C)(=O)=O)CC1] | 3.63 ± 0.10 | 2.03 ± 0.02 |
| 15 | 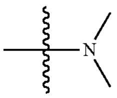 [SMILES: *N(C)C] | 1.08 ± 0.09 | NT | 24 | 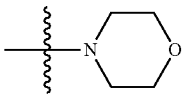 [SMILES: *N1CCOCC1] | 1.00 ± 0.07 | NT |
| 16 | 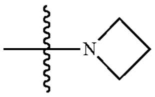 | 1.38 ± 0.11 | NT | 25 | 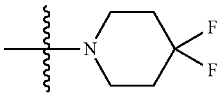 [SMILES: *N1CCC(F)(F)CC1] | 1.54 ± 0.03 | NT |
| 17 | 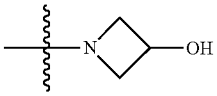 [SMILES: *N1CC(O)C1] | 1.47 ± 0.10 | NT | 26 | 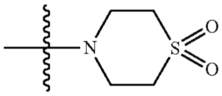 [SMILES: *N1CCS(=O)(=O)CC1] | 2.24 ± 0.09 | 1.32 ± 0.01 |
| 18 | 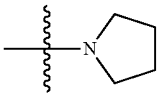 | 1.22 ± 0.03 | NT | 27 | 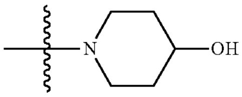 [SMILES: *N1CCC(O)CC1] | 2.38 ± 0.15 | 1.29 ± 0.05 |
| 19 | 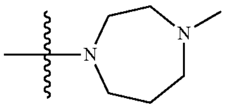 [SMILES: *N1CCCN(C)CC1] | 4.23 ± 0.06 | 2.18 ± 0.02 | 28 | 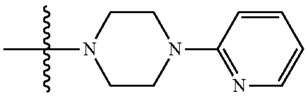 [SMILES: *N1CCN(c2ccccn2)CC1] | 1.82 ± 0.11 | NT |
| 20 | 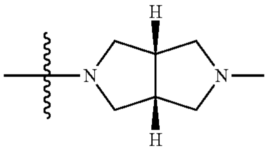 [SMILES: *N1C[C@@H]2CN(C)C[C@@H]2C1] | 4.24 ± 0.04 | 2.00 ± 0.11 | 29 | 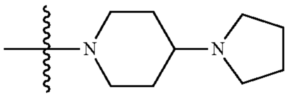 [SMILES: *N1CCC(N2CCCC2)CC1] | 3.44 ± 0.07 | 1.89 ± 0.01 |
| 21 | 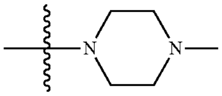 | 4.62 ± 0.12 | 2.44 ± 0.04 | 30 | 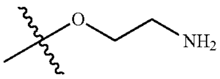 [SMILES: *OCCN] | 0.89 ± 0.11 | NT |

[a]Activation folds on Sirt6 activity of compounds at 100 μM and 30 μM were determined in an assay using a Sirt6 fluorometric activity kit. The results represent mean ± SD from at least two independent experiments.

Activation folds on Sirt6 activity of compounds at 100 μM and 30 μM were determined in an assay using a Sirt6 fluorometric activity kit. The results represent mean SD from at least two independent experiments.

Through the above initial SAR investigation, compound 21 with the 4-methylpiperazin-1-yl moiety was found to be the most potent compound to activate Sirt6. To further explore the effect of different side chains linked to the terminal nitrogen of piperazinyl moiety, compounds 35-50 were designed, synthesized, and pharmacologically evaluated (Table 2). The alkyl side chains bearing terminal hydroxyl (35), ether (36 and 37), dimethylamino (38), and dimethylcarbamoyl (39) were all well tolerated, presenting significantly improved activating effects (5.02~7.38-fold at 100 μM and 2.92~3.83-fold at 30 μM). In contrast to compound 21, compound 40 with cyanomethyl maintained the same level of potency, while its reduced amide analog 41 exhibited slightly decreased Sirt6 deacetylation activity. The substituted acyl groups (42 and 43) were unfavorable for the activating effects. Excitingly, the carbamide analog 44 bearing a 3-hydroxyazetidine moiety also showed potent activity in activating Sirt6 deacetylation (5.26-fold at 100 μM and 2.67-fold at 30 μM). Introducing additional heterocycles with a two-carbon linker yielded compounds 45-50. Notably, all these compounds displayed excellent activating activity on Sirt6, with activation folds of 5.38-6.30 and 2.81~4.80 at 100 μM and 30 μM, respectively.

TABLE 2

Effect of Compounds 35-50 on Sirt6-dependent Peptide Deacetylation Activation[a]

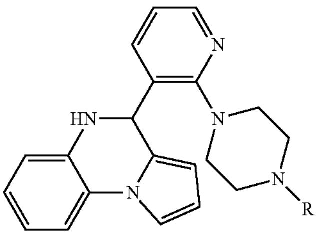

| Entry | R | Activation Fold[a] 100 μM | 30 μM | Entry | R | Activation Fold 100 μM | 30 μM |
|---|---|---|---|---|---|---|---|
| 35 | 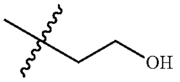 [SMILES: *CCO] | 5.72 ± 0.69 | 2.92 ± 0.06 | 43 | 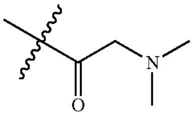 [SMILES: *C(=O)CN(C)C] | 3.78 ± 0.15 | 2.31 ± 0.07 |
| 36 | 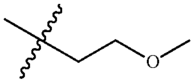 [SMILES: *CCOC] | 6.06 ± 0.13 | 3.17 ± 0.21 | 44 | 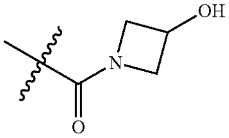 [SMILES: *C(=O)N1CC(O)C1] | 5.26 ± 0.13 | 2.67 ± 0.19 |
| 37 | 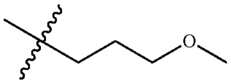 [SMILES: *CCCOC] | 5.02 ± 0.25 | 3.13 ± 0.14 | 45 | 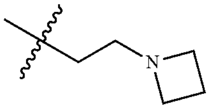 [SMILES: *CCN1CCC1] | 5.85 ± 0.01 | 2.81 ± 0.01 |
| 38 | 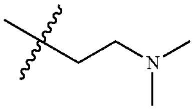 [SMILES: *CCN(C)C] | 7.38 ± 0.6 | 3.83 ± 0.46 | 46 | 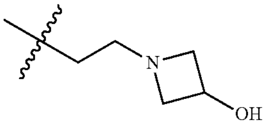 [SMILES: *CCN1CC(O)C1] | 6.30 ± 0.25 | 3.30 ± 0.11 |
| 39 | 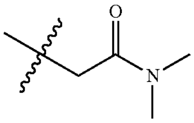 [SMILES: *CC(=O)N(C)C] | 6.60 ± 0.22 | 3.21 ± 0.06 | 47 | 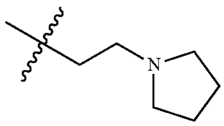 [SMILES: *CCN1CCCC1] | 5.38 ± 0.29 | 4.80 ± 0.19 |
| 40 | 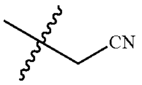 [SMILES: *CC#N] | 4.74 ± 0.26 | 2.37 ± 0.04 | 48 | 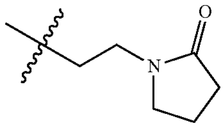 [SMILES: *CCN1CCCC1=O] | 5.64 ± 0.43 | 3.48 ± 0.02 |
| 41 | 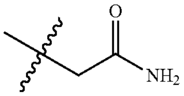 [SMILES: *CC(N)=O] | 3.43 ± 0.48 | 1.73 ± 0.12 | 49 | 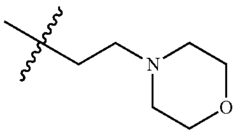 [SMILES: *CCN1CCOCC1] | 5.99 ± 0.21 | 3.02 ± 0.04 |
| 42 | 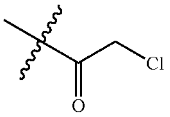 [SMILES: *C(=O)CCl] | 2.84 ± 0.28 | 1.93 ± 0.02 | 50 | 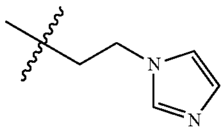 [SMILES: *CCn1ccnc1] | 6.29 ± 0.02 | 3.34 ± 0.19 |

[a]Activation folds on Sirt6 activity of compounds at 100 μM and 30 μM were determined in an assay using a Sirt6 fluorometric activity kit. The results represent mean ± SD from at least two independent experiments.

Next, other positions of the pyridyl moiety and the tricyclic ring were explored while retaining the side chain of 4-(2-(dimethylamino)ethyl)piperazin-1-yl of compound 38 which displayed an excellent activating effect on Sirt6. As listed in Table 3, moving the nitrogen from the ortho to para position of the side chain (60) or inserting an additional nitrogen (61) or 5-Cl (62) on the pyridine ring led to a complete loss in activating Sirt6 deacetylation. Intriguingly, in contrast to compound 38, the substitution of the pyridine ring with the benzene ring (63) only resulted in a slight decrease in potency, exhibiting the activation fold of 5.43 and 2.62 at 100 μM and 30 μM, respectively. Either acetylating the —NH— group of the tricyclic ring (64) or dehydrogenating the quinoxaline ring (65) was unfavorable, and not active up to 100 μM. Interestingly, replacing the —NH— group of the quinoxaline ring with an oxygen atom (66) slightly diminished the activating effect (4.23-fold at 100 μM and 2.67-fold at 30 μM). The ring-opened derivative 67 did not activate Sirt6.

TABLE 3

Effect of Compounds 60-67 on Sirt6-dependent Peptide Deacetylation Activation[a]

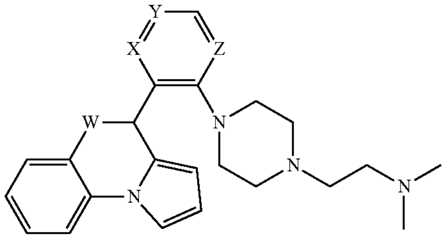

60-64, 66

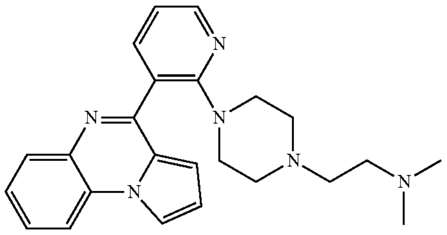

65

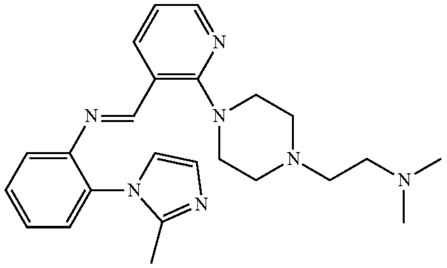

67

| Entry | W | X | Y | Z | Activation Fold[a] 100 μM | 30 μM |
|---|---|---|---|---|---|---|
| 60 | NH | CH | N | CH | 1.07 ± 0.18 | NT[b] |
| 61 | NH | N | CH | N | 0.97 ± 0.05 | NT |
| 62 | NH | CH | CCl | N | 0.98 ± 0.01 | NT |
| 63 | NH | CH | CH | CH | 5.43 ± 0.21 | 2.62 ± 0.34 |
| 64 | $NCOCH_3$ | CH | CH | N | 0.94 ± 0.03 | NT |
| 65 | | | | | 0.99 ± 0.01 | NT |
| 66 | O | CH | CH | N | 4.23 ± 0.22 | 2.67 ± 0.01 |
| 67 | | | | | 0.92 ± 0.03 | NT |

TABLE 3-continued

Effect of Compounds 60-67 on Sirt6-dependent Peptide Deacetylation Activation[a]

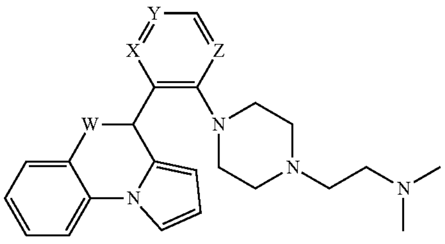

60-64, 66

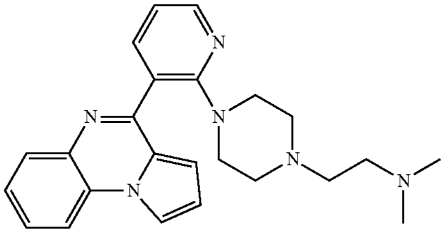

65

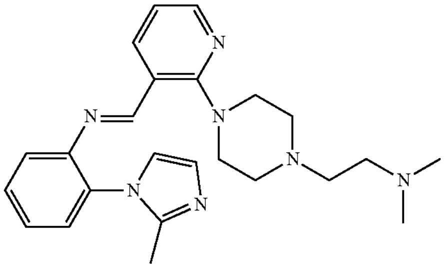 [SMILES: CN(C)CCN1CCN(c2ncccc2-c2nc3ccccc3n3cccc23)CC1]

67

| Entry | W | X | Y | Z | Activation Fold[a] 100 μM | 30 μM |
|---|---|---|---|---|---|---|

[a]Activation folds on Sirt6 activity of compounds at 100 μM and 30 μM were determined in an assay using a Sirt6 fluorometric activity kit.

[b]NT: not tested. The results represent mean ± SD from at least two independent experiments.

To facilitate a quick investigation of the effect of substituents on other positions of the tricyclic system, the tricyclic ring of derivative 66 of 4H-benzo[b]pyrrolo[1,2-d][1,4]oxazine was kept intact to prepare and evaluate compounds 68-76 (Table 4). As compared with compound 66, insertion of 8-$CH_3$ (68), 8-$OCH_3$ (69), 7-$COOCH_3$ (71), or 1-Br (76) on the tricyclic ring maintained the same level of potency with activation folds of 4.20-5.65 and 2.69-4.51 at 100 μM and 30 μM, respectively. Compounds with 8-F (70) and 7-$CH_2OH$ (72) showed a decrease in activating Sirt6 deacetylation (2.53-fold and 2.69-fold at 100 μM, respectively) while the substituents 7-$CONH_2$ (73), 7-CONH$(CH_2)_2SO_2CH_3$ (74), and 1-$CH_2OH$ (75) resulted in a dramatic loss of potency. These results suggested that the hydrophobic groups such as methyl and trifluoromethyl on the tricyclic ring are beneficial for the activating effect on Sirt6, while the hydrophilic substituents such as hydroxyl and sulfonyl are unfavorable.

TABLE 4

Effect of Compounds 68-76 on Sirt6-dependent Peptide Deacetylation Activation[a]

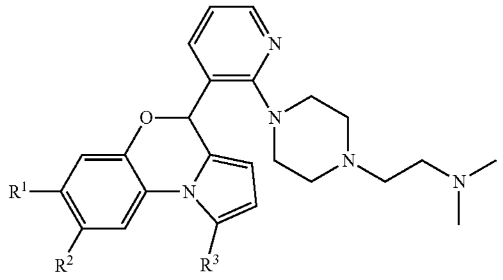

| Entry | $R^1$ | $R^2$ | $R^3$ | Activation Fold[a] | |
| --- | --- | --- | --- | --- | --- |
| | | | | 100 μM | 30 μM |
| 68 | H | $CH_3$ | H | 4.56 ± 0.04 | 2.99 ± 0.05 |
| 69 | H | $OCH_3$ | H | 5.65 ± 0.22 | 4.51 ± 0.06 |
| 70 | H | F | H | 2.53 ± 0.05 | 1.84 ± 0.04 |
| 71 | $COOCH_3$ | H | H | 4.82 ± 0.14 | 4.16 ± 0.18 |
| 72 | $CH_2OH$ | H | H | 2.69 ± 0.03 | 1.59 ± 0.03 |
| 73 | $CONH_2$ | H | H | 0.83 ± 0.01 | NT[b] |
| 74 | 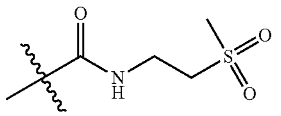 [SMILES: *C(=O)NCCS(C)(=O)=O] | H | H | 0.96 ± 0.02 | NT |
| 75 | H | H | $CH_2OH$ | 1.16 ± 0.06 | NT |
| 76 | H | H | $CF_3$ | 4.20 ± 0.06 | 2.69 ± 0.02 |

[a]Activation folds on Sirt6 activity of compounds at 100 μM and 30 μM were determined in an assay using a Sirt6 fluorometric activity kit.
[b]NT: not tested. The results represent mean + SD from at least two independent experiments.

2.3. Time-Dependent Sirt6 Activation of Selected Compounds

Six potent and representative compounds (35, 36, 38, 46, 47, and 50), were selected to evaluate their activating effects on Sirt6 deacetylation at different time points, and compared their activities with that of lead compound UBCS039. As shown in FIG. 2, these selected compounds exhibited a declining trend in promoting Sirt6 activity from 15 min to 125 min at concentrations of both 100 μM and 30 μM, which is a typical phenomenon of enzyme reaction when the substrate is consumed over time. The maximum activating effects were observed at 15 min for these compounds, displaying ~5-8-fold and ~3-5-fold activation at 100 μM and 30 μM, respectively, which is much higher than the activity of UBCS039.

2.4. Evaluation of Selected Compounds on Sirtl and Sirt3 Deacetylation

To detect whether the activating effect on Sirt6 deacetylation of this class of derivatives is selective, effects on Sirtl and Sirt3 deacetylation were measured. As expected, compounds 35, 36, and 38 specifically promoted Sirt6 activity (FIG. 3A), but showed no significant effects on Sirtl and Sirt3 deacetylation (FIGS. 3B and 3C), in agreement with the reported selectivity of the lead compound UBCS039 [28].

2.5. Docking Analysis of Compound 38 with Sirt6 Protein

A docking study of compound 38 with Sirt6/ADP ribose structure (PDB ID: 5MF6) demonstrated that the core of 38 binds to Sirt6 at the hydrophobic pocket formed by F64/82/86, 161, P62, and M136, the binding site where UBCS039 binds at, in a slightly different conformation (FIGS. 4A and 4B). The tricyclic moiety of compound 38 is anchored at the hydrophobic pocket through hydrophobic interaction with F64/82/86, 161, and VI 15, while the pyridine ring interacts with M136 through hydrophobic interaction, consistent with previous SAR results that the hydrophobic substituents on the tricyclic ring are beneficial and introducing the benzene ring instead of the pyridine ring is well tolerated. The additional piperazinyl moiety of the side chain extended to the exit of the acyl channel, into a site formed by L186, D187, W188, M157, and W71. The protonated nitrogen of the dimethylamino group on the side chain formed π cation interactions with W188 (FIG. 4A), further stabilizing compound 38 into this extended binding pocket.

2.6. Evaluation of Selected Compounds on the Deacetylation of H3K9 in Nucleosomes Next, effects of selected compounds were explored for Sirt6-dependent deacetylation of complete nucleosomes extracted from human embryonic kidney (HEK) 293T cells, as nucleosomes represent more physiologically relevant substrates. As shown in FIG. 5A, compounds 35, 36, 38, 46, and 50 significantly decreased the acetylation of H3K9 in the nucleosome test, while no effect was observed for compound 47, likely due to poor aqueous solubility. More importantly, no obvious toxicity on retinal precursor cells (R28) was observed for these compounds at 30 μM, and even at 100 μM for compounds 35 and 36 (FIGS. 5B and 5C), indicating their great safety advantages.

2.7. Evaluation of Compounds 35 and 36 in Cancer Cells

Considering the strong activating effects on the deacetylation of H3K9 in nucleosomes as well as the low toxicity on R28 cells, compounds 35 and 36 were further selected to evaluate their effects on Sirt6 deacetylation in cancer cells. Briefly, cancer cells H1299 and PLC/PRF/5 with compounds 35 or 36 at the indicated concentrations for 24 hours, then calculated the ratio of acetylated H3K9 to total histone H3. Compound 36 significantly activated Sirt6 to deacetylate H3K9 at 30 μM in both H1299 and PLC/PRF/5 cells, while no obvious influence was observed for compound 35 (FIGS. 6A and 6B). When Sirt6 was knockdown by siRNA, the decrease of acetylated H3K9 by compound 36 was abolished in both H1299 and PLC/PRF/5 cells (FIGS. 6C and 6D), suggesting that the activity of compound 36 depends on Sirt6. As Sirt6 acts as a tumor suppressor in some cancer types, such as non-small cell lung carcinoma and hepatoma,[5, 34-37] Effects of compounds 35 and 36 were further evaluated for the clonogenicity of H1299 and PLC/PRF/5 cells in a colony formation. As shown in FIGS. 6E and 6F, about half of colony formation of H1299 and PLC/PRF/5 cells was blocked by 36 at 30 μM, but only a slight inhibitory effect was observed for 35.

2.8. Anti-Inflammatory Activities of Selected Compounds

Figure 7H:
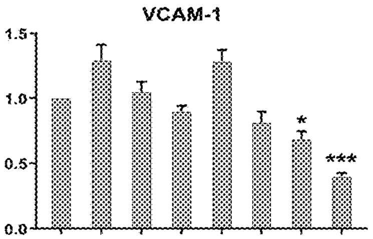
Figure 7I:
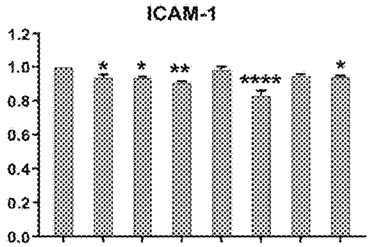

Sirt6 plays a pivotal role in regulating inflammatory diseases [38-40]. It was reported that Sirt6 interacts with the NF-κB RelA subunit and modulates NF-κB-dependent gene expression via its deacetylation of H3K9 at NF-κB target gene promoters [41]. Here, NF-κB targeted inflammatory genes (IL-1β, IL-6, MCP-1, TNFα, iNOS, CXCL10, VCAM-1 and VCAM-1) were chosen to assess the anti-inflammatory effects of this class of derivatives. BV2, a type of immortalized murine microglial cells which are widely used to determine the mechanisms of microglial activation [42], were pretreated with 30 μM compounds for 30 minutes followed by the treatment of 100 ng/mL LPS for 6 hours. The expressions of inflammatory genes, including IL-1β, IL-6, MCP-1, TNFα, iNOS, CXCL10, VCAM-1, and ICAM-1 were significantly induced by LPS treatment (FIG. 7A). Intriguingly, all selected compounds (35, 36, 38, 46, 47, and 50), as well as the lead compound UBCS039, strongly inhibited LPS-induced expression of IL-1β, IL-6, MCP-1, and TNFα, and especially, compounds 46, 47, and 50 almost reversed LPS-induced IL-1β, IL-6, and MCP-1 response (FIGS. 7B-7E). In addition, compounds 46, 47, and 50 significantly repressed LPS-induced iNOS and CXCL10 expression (FIGS. 7F and 7G), whereas 46 and 47 could also obviously inhibit VCAM-1 induction (FIG. 7H). However, selected compounds 35, 38, 47, and 50 only exhibited a slight inhibition against ICAM-1 induction (FIG. 7I). This data highlight the use of class of Sirt6 activators as potentanti-inflammatory agents.

2.9. Anti-SARS-CoV-2 Activities of Selected Compounds

SARS-CoV-2 is an enveloped and positive-sense single-stranded RNA virus that is responsible for the ongoing global pandemic of debilitating respiratory illness COVID-19 [43-45]. Four potent Sirt6 activators (35, 36, 38, and 46) along with the lead compound UBCS039 were selected for evaluating their potentials against SARS-CoV-2. Interestingly, as shown in FIGS. 8A and 8C, these compounds showed micromolar potency in inhibiting SARS-CoV-2 infection, and compound 38, the most potent one, displayed an $EC_{50}$ value of 9.3 μM. In addition, none of these compounds exhibited significant cytotoxicity at the highest tested concentration of 50 μM (FIG. 8B). These data confirms the therapeutic application of Sirt6 activators as SARS-CoV-2 inhibitors. However, their exact mechanism in inhibiting SARS-CoV-2 remains to be elucidated.

Non-Limiting Embodiments

A non-limiting list of embodiments encompassed by the invention is provided below.

In a first embodiment, the invention encompasses a compound according to Formula (I):

Formula (I)

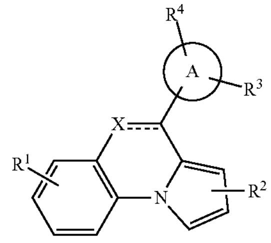

or a pharmaceutically acceptable salt, tautomer, or isotopologue thereof, wherein:

- ---- represents a single or double bond;
- X is $NR^5$ or N or O or C;
- $R^5$ is chosen from hydrogen, alkyl, cycloalkyl, alkoxyalkyl, alkylcarbonyl, or alkylsulfonyl;
- A is a five to ten membered ring e.g., chosen from aryl, heteroaryl, or fused heteroaryl;
- $R^1$, $R^2$, $R^4$ are independently chosen from hydrogen, alkyl, cycloalkyl, haloalkyl, haloalkoxy, alkoxy, halo, cyano, carboxy, alkoxycarbonyl-$R^8$, alkylcarbonyl-$R^8$, aminocarbonyl, alkylaminocarbonyl-$R^8$, alkoxyalkyl, aminoalkyl, aminoalkoxy, hydroxyl, and hydroxyalkyl;
- $R^3$ is a four to eight membered heterocycle, substituted with one or more $R^6$ substituents;
- $R^6$ is chosen from hydrogen, hydroxyl, halo, alkyl-$R^7$, alkoxy, cycloalkyl, carbonyl-$R^7$, alkylcarbonyl-$R^7$, alkylsulfonyl, heteroaryl, and heterocyclyl; wherein $R^7$ is chosen from hydrogen, hydroxyl, halo, alkoxy, amino, cyano, alkylamino, dialkylamino, aminocarbonyl, alkylaminocarbonyl, dialkylaminocarbonyl, heterocyclyl, or heteroaryl; wherein $R^8$ is chosen from hydrogen, halo, hydroxyl, cycloalkyl, alkoxy, and alklysulfonyl.

In some embodiments, the invention encompasses a compound of Formula (I), wherein X is $NR^5$ or N or O;

In some embodiments, the invention encompasses a compound of Formula (I), wherein $R^5$ is hydrogen, or alkylcarbonyl;

In some embodiments, the invention encompasses a compound of Formula (I), wherein $R^2$ is hydrogen, $CF_3$, or $CH_2OH$.

In some embodiments, the invention encompasses a compound of Formula (I), wherein A is aryl, pyrazinyl, or pyridyl;

In some embodiments, the invention encompasses a compound of Formula (I), wherein $R^4$ is hydrogen or halo.

In some embodiments, the invention encompasses a compound of Formula (I), wherein the heterocycle in $R^3$ is chosen from piperazine, morpholine, piperidine, pyrrolidine, and azetidine.

In some embodiments, the invention encompasses a compound of Formula (I), wherein $R^6$ is chosen from hydrogen, acetyl, methane sulfonyl, halo, pyridyl, methyl, hydroxyl, hydroxyalkyl, N,N-dimethylaminoalkyl, alkoxyalkyl, $CH_2C(O)N(Me)_2$, pyrrolidon-1-yl, urea, cyanoalkyl, chloromethylacetyl, and 2-(imidazol-1-yl)-ethyl, 2-(morpholin-4-yl)-ethyl.

In some embodiments, the invention encompasses a compound according to Formula (Ia), wherein:

Formula (Ia)

($I_a$)

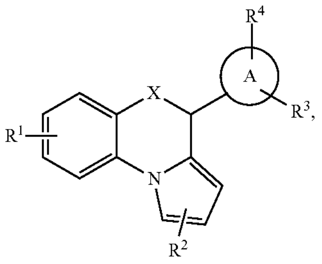

X = $NR^5$, O or a pharmaceutically acceptable salt, tautomer, or isotopologue thereof, wherein:

X is $NR^5$ or O; and wherein A, $R^1$, $R^2$, $R^3$, $R^4$ and $R^5$ are as defined for Formula (I).

In some embodiments, the invention encompasses a compound according to Formula (Ib), wherein:

Formula (Ib)

($I_b$)

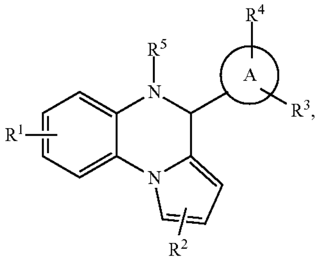

or a pharmaceutically acceptable salt, tautomer, or isotopologue thereof, wherein:

A, $R^1$, $R^2$, $R^3$, $R^4$ and $R^5$ are as defined for Formula (I).

In some embodiments, the invention encompasses a compound according to Formula (Ic), wherein:

Formula ($I_c$)

($I_c$)

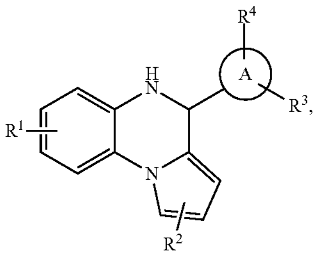

or a pharmaceutically acceptable salt, tautomer, or isotopologue thereof, wherein:

A, $R^1$, $R^2$, $R^3$, and $R^4$ are as defined for Formula (I).

In some embodiments, the invention encompasses a compound according to Formula (Id), wherein:

Formula ($I_d$)

($I_d$)

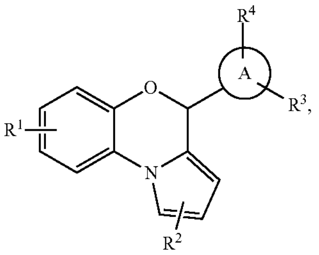

or a pharmaceutically acceptable salt, tautomer, or isotopologue thereof, wherein:

A, $R^1$, $R^2$, $R^3$, and $R^4$ are as defined for Formula (I).

In some embodiments, the invention encompasses a compound according to Formula (Ie), wherein:

Formula ($I_e$)

($I_e$)

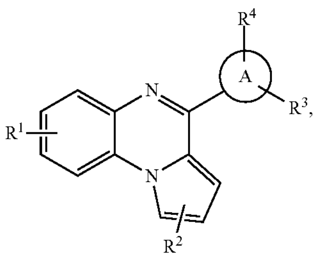

or a pharmaceutically acceptable salt, tautomer, or isotopologue thereof, wherein:

A, $R^1$, $R^2$, $R^3$, and $R^4$ are as defined for Formula (I).

In some embodiments, the invention encompasses a compound according to Formula (II), wherein:

Formula (II)

(II)

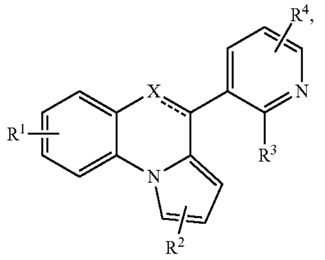

or a pharmaceutically acceptable salt, tautomer, or isotopologue thereof, wherein:

X, $R^1$, $R^2$, $R^3$, and $R^4$ are as defined for Formula (I).

In some embodiments, the invention encompasses a compound according to Formula (IIa), wherein:

Formula (IIa)

($II_a$)

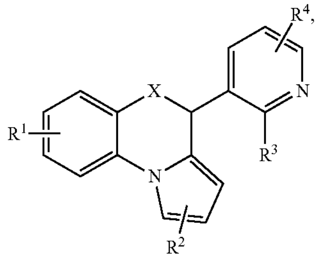

X = $NR^5$, O or a pharmaceutically acceptable salt, tautomer, or isotopologue thereof, wherein:

X is $NR^5$; and $R^1$, $R^2$, $R^3$, $R^4$ and $R^5$ are as defined for Formula (I).

In some embodiments, the invention encompasses a compound according to Formula (IIb), wherein:

Formula (IIb)

($II_b$)

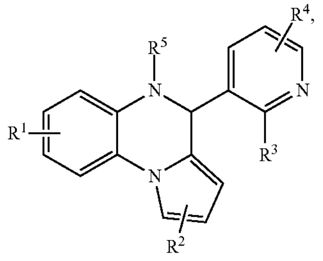

or a pharmaceutically acceptable salt, tautomer, or isotopologue thereof, wherein:

$R^1$, $R^2$, $R^3$, $R^4$ and $R^5$ are as defined for Formula (I).

In some embodiments, the invention encompasses a compound according to Formula (IIc), wherein:

Formula (IIc)

($II_c$)

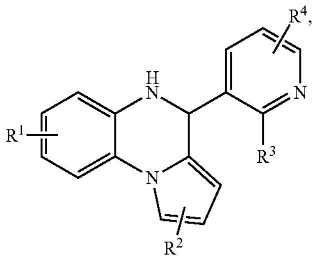

or a pharmaceutically acceptable salt, tautomer, or isotopologue thereof, wherein:

$R^1$, $R^2$, $R^3$, and $R^4$ are as defined for Formula (I).

In some embodiments, the invention encompasses a compound according to Formula (IId), wherein:

Formula (IId)

($II_d$)

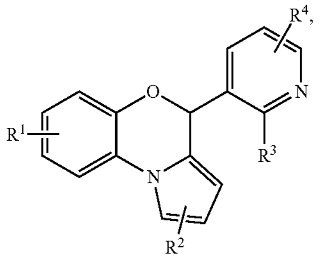

or a pharmaceutically acceptable salt, tautomer, or isotopologue thereof, wherein:

$R^1$, $R^2$, $R^3$, and $R^4$ are as defined for Formula (I).

In some embodiments, the invention encompasses a compound according to Formula (IIe), wherein:

Formula (IIe)

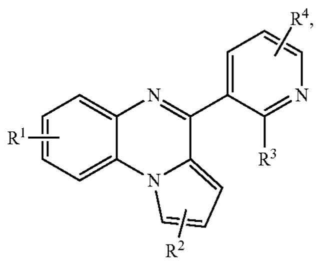

($II_e$)

or a pharmaceutically acceptable salt, tautomer, or isotopologue thereof, wherein:

$R^1$, $R^2$, $R^3$, and $R^4$ are as defined for Formula (I).

In some embodiments, the invention encompasses a compound according to Formula (III), wherein:

Formula (III)

(III)

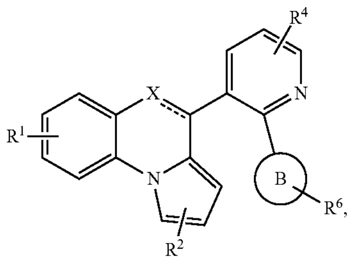

or a pharmaceutically acceptable salt, tautomer, or isotopologue thereof, wherein:

B is a four to eight membered heterocycle, substituted with one or more $R^6$ substituents; and X, $R^1$, $R^2$, $R^4$, and $R^6$ are as defined for Formula (I).

In some embodiments, the invention encompasses a compound according to Formula (IIIa), wherein:

Formula (IIIa)

(III)

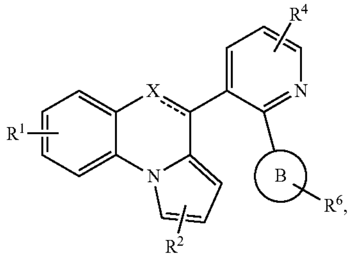

or a pharmaceutically acceptable salt, tautomer, or isotopologue thereof, wherein:

B is a four to eight membered heterocycle, substituted with one or more $R^6$ substituents; and X, $R^1$, $R^2$, $R^4$, and $R^6$ are as defined for Formula (I).

In some embodiments, the invention encompasses a compound according to Formula (IV), wherein:

Formula (IV)

(IV)

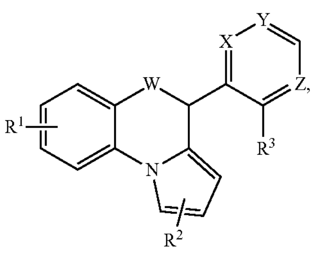

W = NH, O, $NR^5$ (Scheme III)

or a pharmaceutically acceptable salt, tautomer, or isotopologue thereof, wherein:

W is NH, O, or $NR^5$;

X is N or CH;

Y is N, CH, or C-halogen;

Z is N or CH;

wherein at least one of X, Y, and Z is CH; and $R^1$, $R^2$, $R^3$ and $R^5$ are as defined for Formula (I).

In some embodiments, the invention encompasses a compound according to Formula (V), wherein:

Formula (V)

(V)

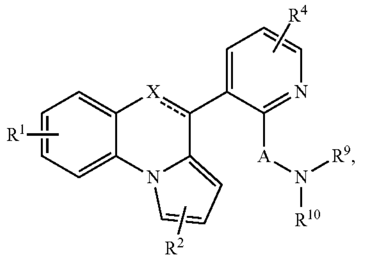

A = bond; $-O(CH_2)_n-$, $-(CH_2)_m-$ $R^9$, $R^{10}$: H, acyl, alkyl or a pharmaceutically acceptable salt, tautomer, or isotopologue thereof, wherein:

X, $R^1$, $R^2$, and $R^4$ are as defined for Formula (I);

A is a bond, $-O(CH_2)_n-$, or $-(CH_2)_m$, wherein n and m are independently 1 to 8; and $R^9$ and $R^{10}$ are independently H or C1-C8 alkyl.

In some embodiments, the invention encompasses a compound according to Formula (VI), wherein:

Formula (VI)

(VI)

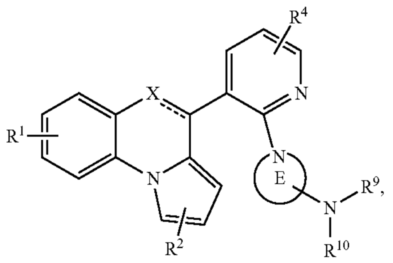

or a pharmaceutically acceptable salt, tautomer, or isotopologue thereof, wherein:

X, $R^1$, $R^2$, and $R^4$ are as defined for Formula (I);

E is a four to 8 membered heterocyclic ring; and $R^9$ and $R^{10}$ are independently H or C1-C8 alkyl.

In some embodiments, the invention encompasses a compound (cpd) chosen from any of the following:
| Cpd No. | Structure |
|---|---|
| 21 | 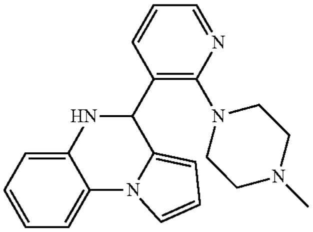 [SMILES: CN1CCN(c2ncccc2C2Nc3ccccc3-n3cccc32)CC1] |
| 30 | 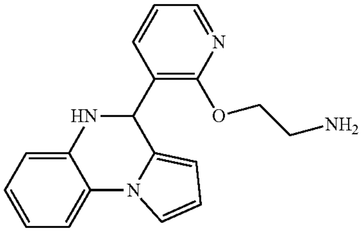 [SMILES: NCCOc1ncccc1C1Nc2ccccc2-n2cccc21] |
| 22 | 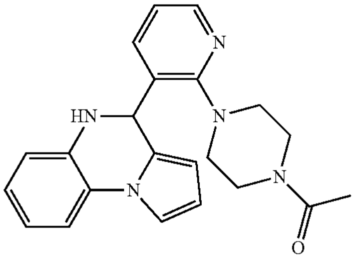 [SMILES: CC(=O)N1CCN(c2ncccc2C2Nc3ccccc3-n3cccc32)CC1] |
| 23 | 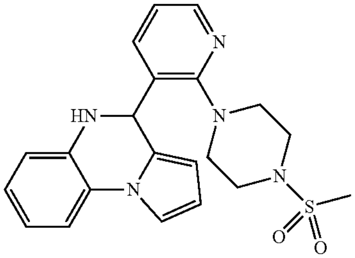 [SMILES: CS(=O)(=O)N1CCN(c2ncccc2C2Nc3ccccc3-n3cccc32)CC1] |
| 24 | 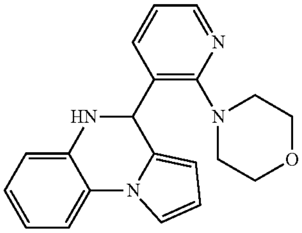 [SMILES: c1ccc2c(c1)NC(c1cccnc1N1CCOCC1)c1cccn1-2] |
| 25 | 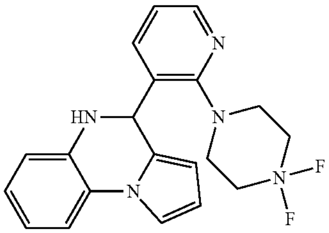 |

-continued
| Cpd No. | Structure |
|---|---|
| 18 | 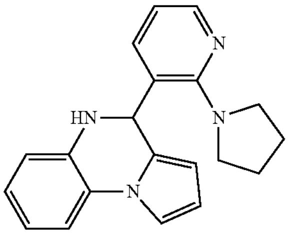 [SMILES: c1ccc2c(c1)NC(c1cccnc1N1CCCC1)c1cccn1-2] |
| 28 | 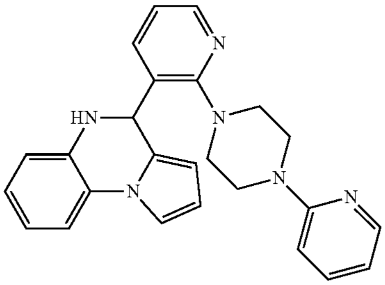 [SMILES: c1ccc(N2CCN(c3ncccc3C3Nc4ccccc4-n4cccc43)CC2)nc1] |
| 29 | 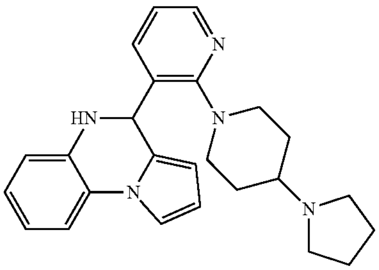 [SMILES: c1ccc2c(c1)NC(c1cccnc1N1CCC(N3CCCC3)CC1)c1cccn1-2] |
| 16 | 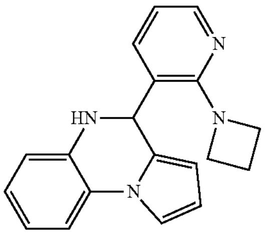 [SMILES: c1ccc2c(c1)NC(c1cccnc1N1CCC1)c1cccn1-2] |
| 19 | 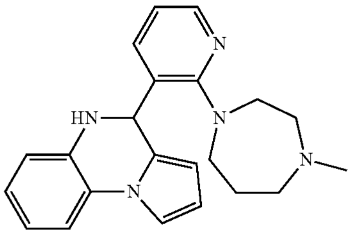 [SMILES: CN1CCCN(c2ncccc2C2Nc3ccccc3-n3cccc32)CC1] |
| 26 | 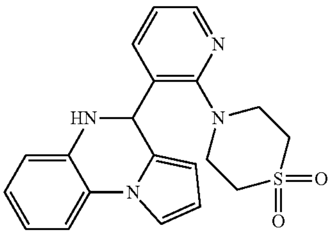 [SMILES: O=S1(=O)CCN(c2ncccc2C2Nc3ccccc3-n3cccc32)CC1] |

-continued
| Cpd No. | Structure |
| --- | --- |
| 20 | 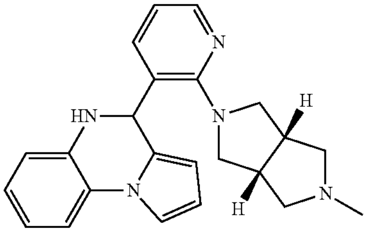 [SMILES: CN1C[C@@H]2CN(c3ncccc3C3Nc4ccccc4-n4cccc43)C[C@@H]2C1] |
| 27 | 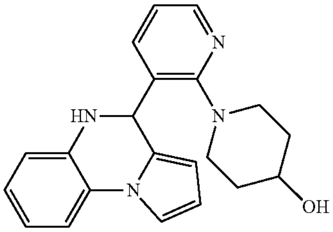 [SMILES: OC1CCN(c2ncccc2C2Nc3ccccc3-n3cccc32)CC1] |
| 17 | 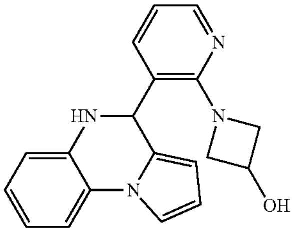 [SMILES: OC1CN(c2ncccc2C2Nc3ccccc3-n3cccc32)C1] |
| 35 | 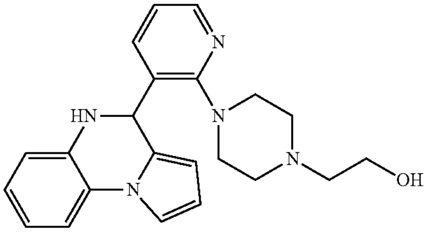 [SMILES: OCCN1CCN(c2ncccc2C2Nc3ccccc3-n3cccc32)CC1] |
| 38 | 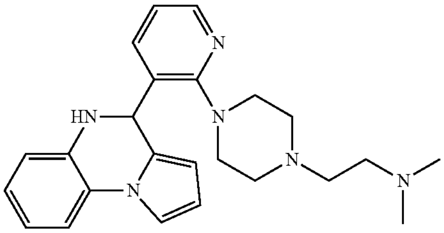 [SMILES: CN(C)CCN1CCN(c2ncccc2C2Nc3ccccc3-n3cccc32)CC1] |
| 36 | 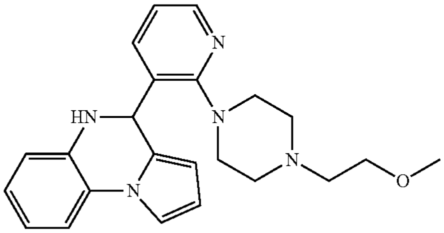 [SMILES: COCCN1CCN(c2ncccc2C2Nc3ccccc3-n3cccc32)CC1] |

-continued
| Cpd No. | Structure |
|---|---|
| 65 | 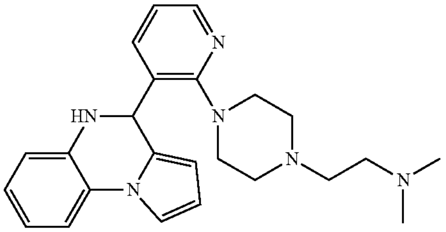 [SMILES: CN(C)CCN1CCN(c2ncccc2C2Nc3ccccc3-n3cccc32)CC1] |
| 37 | 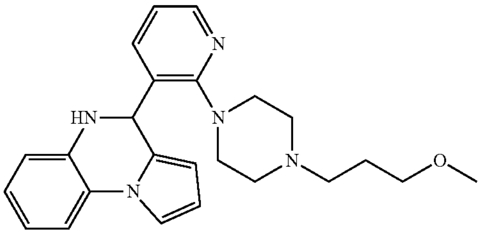 [SMILES: COCCCN1CCN(c2ncccc2C2Nc3ccccc3-n3cccc32)CC1] |
| 39 | 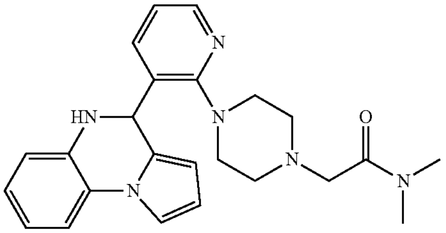 [SMILES: CN(C)C(=O)CN1CCN(c2ncccc2C2Nc3ccccc3-n3cccc32)CC1] |
| 48 | 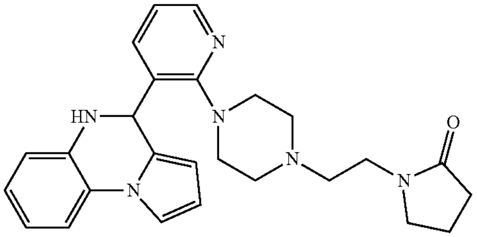 [SMILES: O=C1CCCN1CCN1CCN(c2ncccc2C2Nc3ccccc3-n3cccc32)CC1] |
| 44 | 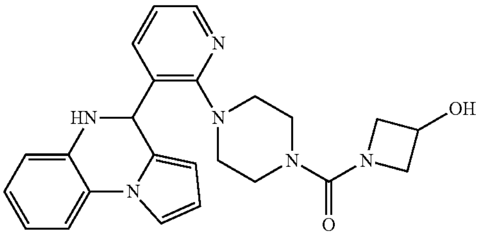 [SMILES: O=C(N1CCN(c2ncccc2C2Nc3ccccc3-n3cccc32)CC1)N1CC(O)C1] |
| 40 | 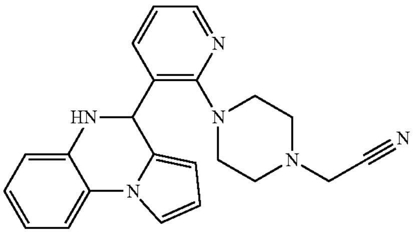 [SMILES: N#CCN1CCN(c2ncccc2C2Nc3ccccc3-n3cccc32)CC1] |

-continued
| Cpd No. | Structure |
| --- | --- |
| 41 | 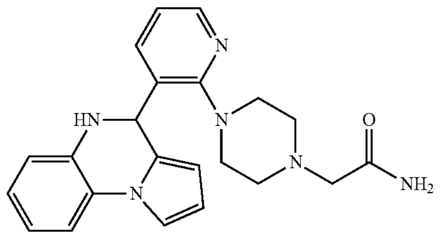 [SMILES: NC(=O)CN1CCN(c2ncccc2C2Nc3ccccc3-n3cccc32)CC1] |
| 42 | 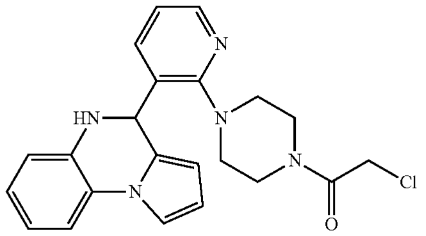 [SMILES: O=C(CCl)N1CCN(c2ncccc2C2Nc3ccccc3-n3cccc32)CC1] |
| 43 | 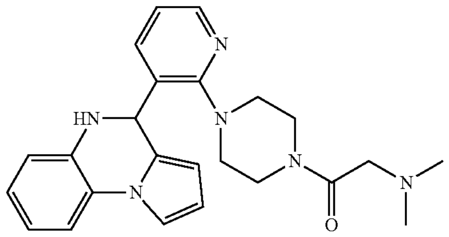 [SMILES: CN(C)CC(=O)N1CCN(c2ncccc2C2Nc3ccccc3-n3cccc32)CC1] |
| 45 | 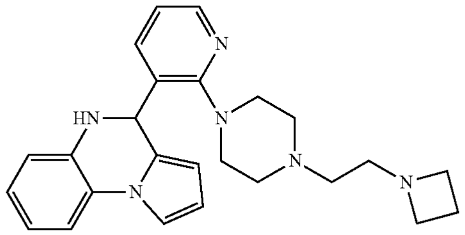 [SMILES: c1ccc2c(c1)NC(c1cccnc1N1CCN(CCN3CCC3)CC1)c1cccn1-2] |
| 46 | 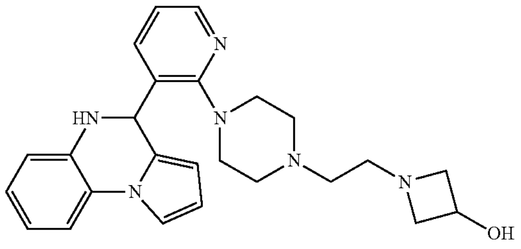 [SMILES: OC1CN(CCN2CCN(c3ncccc3C3Nc4ccccc4-n4cccc43)CC2)C1] |
| 50 | 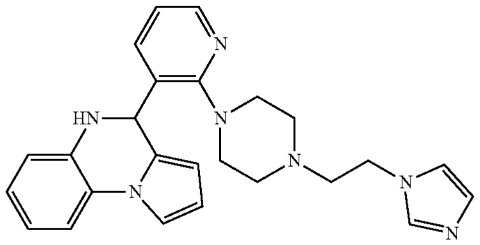 [SMILES: c1ccc2c(c1)NC(c1cccnc1N1CCN(CCn3ccnc3)CC1)c1cccn1-2] |

-continued
| Cpd No. | Structure |
|---|---|
| 47 | 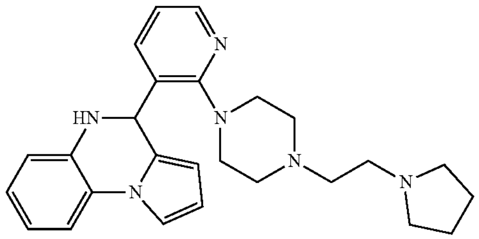 [SMILES: c1ccc2c(c1)NC(c1cccnc1N1CCN(CCN3CCCC3)CC1)c1cccn1-2] |
| 49 | 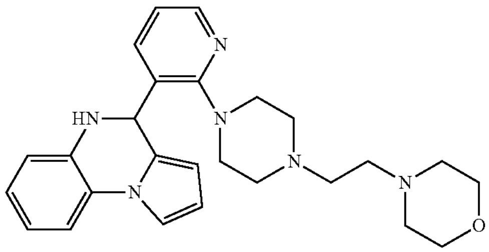 [SMILES: c1ccc2c(c1)NC(c1cccnc1N1CCN(CCN3CCOCC3)CC1)c1cccn1-2] |
| 64 | 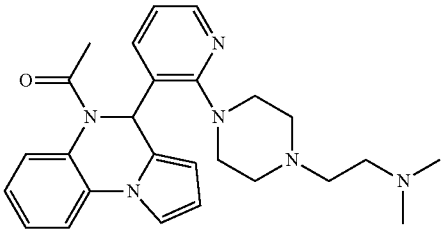 [SMILES: CC(=O)N1c2ccccc2-n2cccc2C1c1cccnc1N1CCN(CCN(C)C)CC1] |
| 60 | 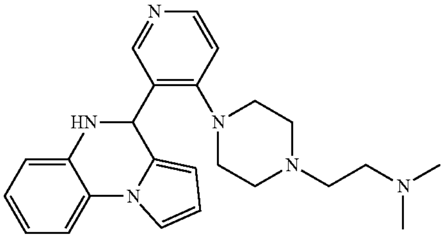 [SMILES: CN(C)CCN1CCN(c2ccncc2C2Nc3ccccc3-n3cccc32)CC1] |
| 62 | 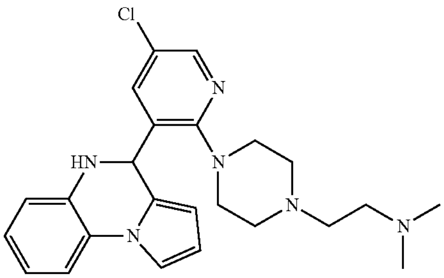 [SMILES: CN(C)CCN1CCN(c2ncc(Cl)cc2C2Nc3ccccc3-n3cccc32)CC1] |
| 61 | 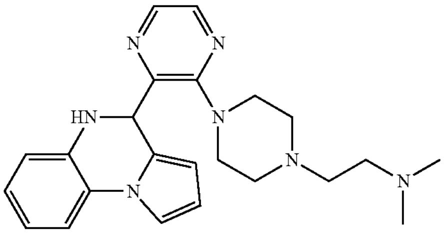 [SMILES: CN(C)CCN1CCN(c2nccnc2C2Nc3ccccc3-n3cccc32)CC1] |

-continued
| Cpd No. | Structure |
|---|---|
| 66 | 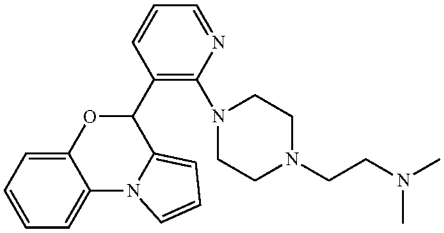 |
| 68 | 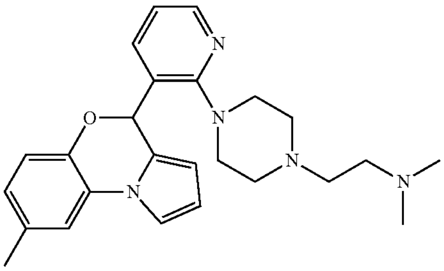 [SMILES: Cc1ccc2c(c1)-n1cccc1C(c1cccnc1N1CCN(CCN(C)C)CC1)O2] |
| 70 | 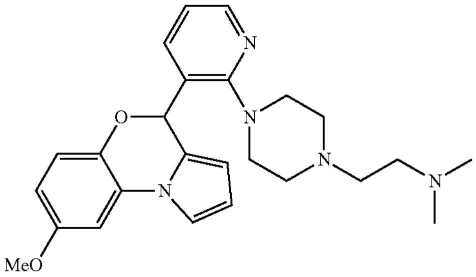 [SMILES: COc1ccc2c(c1)-n1cccc1C(c1cccnc1N1CCN(CCN(C)C)CC1)O2] |
| 69 | 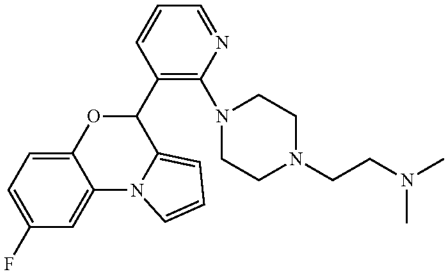 [SMILES: CN(C)CCN1CCN(c2ncccc2C2Oc3ccc(F)cc3-n3cccc32)CC1] |
| 73 | 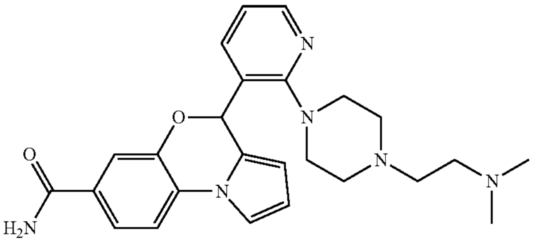 [SMILES: CN(C)CCN1CCN(c2ncccc2C2Oc3cc(C(N)=O)ccc3-n3cccc32)CC1] |
| 71 | 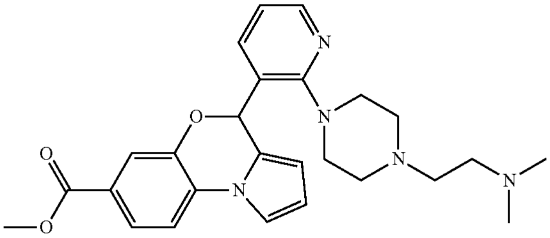 |

-continued
| Cpd No. | Structure |
| --- | --- |
| 72 | 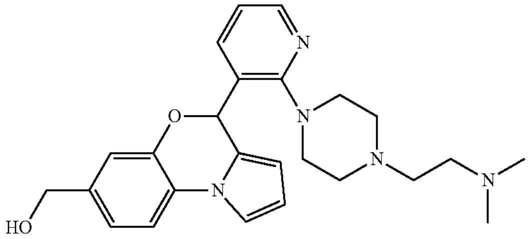 [SMILES: CN(C)CCN1CCN(c2ncccc2C2Oc3cc(CO)ccc3-n3cccc32)CC1] |
| 74 | 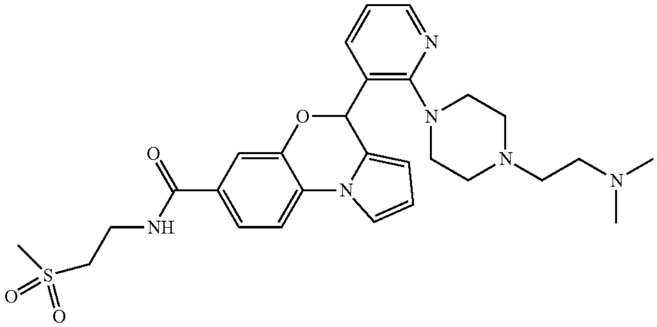 [SMILES: CN(C)CCN1CCN(c2ncccc2C2Oc3cc(C(=O)NCCS(C)(=O)=O)ccc3-n3cccc32)CC1] |
| 76 | 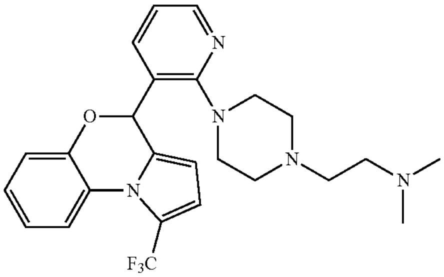 [SMILES: CN(C)CCN1CCN(c2ncccc2C2Oc3ccccc3-n3c2ccc3C(F)(F)F)CC1] |
| 75 | 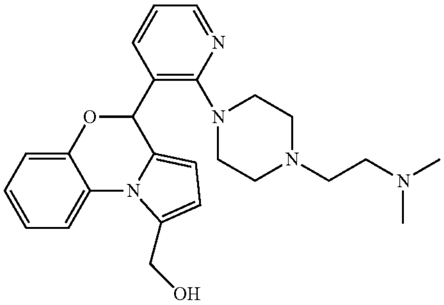 [SMILES: CN(C)CCN1CCN(c2ncccc2C2Oc3ccccc3-n3c(CO)ccc32)CC1] |

In some embodiments, the invention encompasses a compound chosen from:

Compound 35

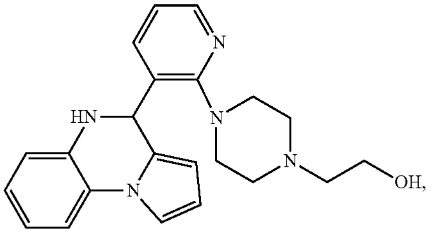

Compound 36

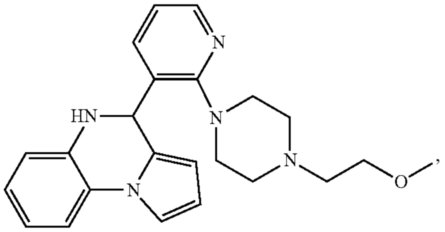

Compound 38

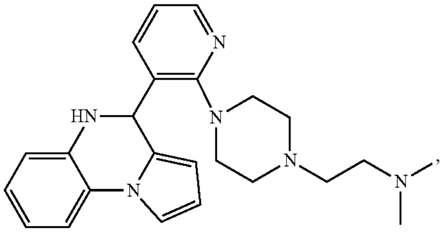

Compound 46

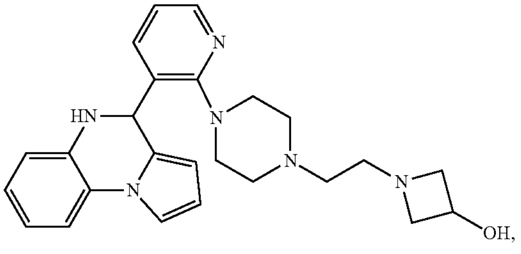

Compound 47

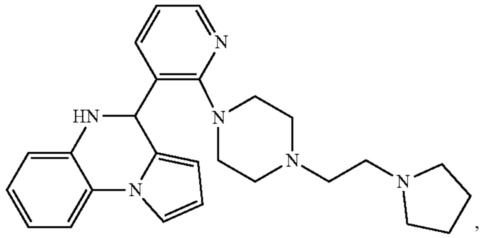

, or

-continued

Compound 50

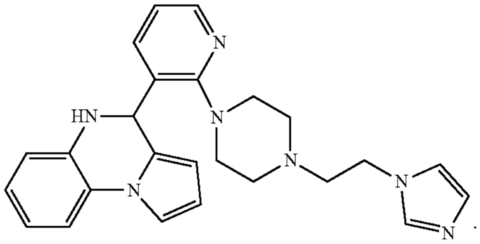

In some embodiments, the invention encompasses a method of treating a disease in a patient comprising administering to the patient a therapeutically effective amount of a compound of any of Formulas (I), (Ia), (Ib), (Ic), (Id), (Ie), (II), (IIa), (IIb), (IIc), (IId), (IIe), (III), (IIIa), (IV), (V), (VI) or a pharmaceutically acceptable salt thereof.

In some embodiments, the invention encompasses said method of treating a disease, wherein treating the disease comprises inhibiting colony formation of cancer cells.

In some embodiments, the invention encompasses said method of treating a disease, wherein treating the disease comprises repressing LPS-induced proinflammatory cytokine/chemokine production.

In some embodiments, the invention encompasses said method of treating a disease, wherein treating the disease comprises suppressing SARS-CoV-2 infection.

In some embodiments, the invention encompasses said method of treating a disease, wherein the disease is chosen from any of cancers, diseases involving inflammation, neurodegeneration, infectious diseases and/or other human conditions.

In some embodiments, the invention encompasses said method of treating a disease, wherein the disease is a cancer chosen from hepatocellular carcinoma, colon cancer, lung cancer, breast cancer, glioma cancer, bone cancer, or skin cancer.

In some embodiments, the invention encompasses said method of treating a disease, wherein the disease is chosen from Alzheimer's disease, dengue virus, autoimmune encephalitis, hepatitis virus, nonalcoholic steatosis (NASH), osteoarthritis, Parkinson's disease, rheumatoid arthritis, retinopathies, corneal diseases, type 2 diabetes mellitus, cardiac hypertrophy, myocardial fibrosis, heart failure, atherosclerosis, myocardial infarction, coronary heart disease, or renal injury.

In some embodiments, the invention encompasses said method of treating a disease, comprising administering another therapeutic agent in combination with any of the compounds of Formulas (I), (Ia), (Ib), (Ic), (Id), (Ie), (II), (IIa), (IIb), (IIc), (IId), (IIe), (III), (IIIa), (IV), (V), or (VI).

In some embodiments, the invention encompasses said method of treating a disease, wherein the compound is chosen from:

Compound 35

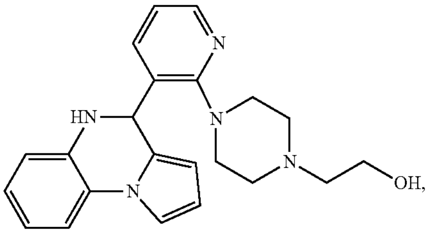

-continued

Compound 36

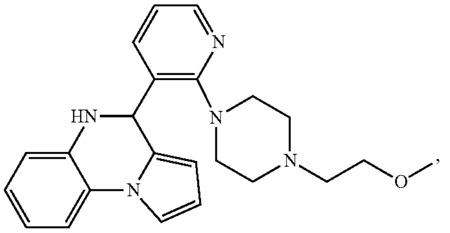

Compound 38

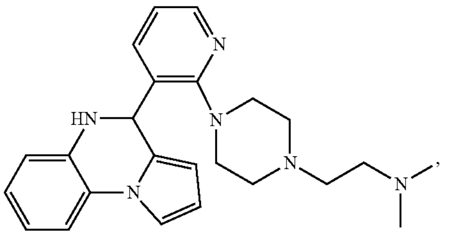

Compound 46

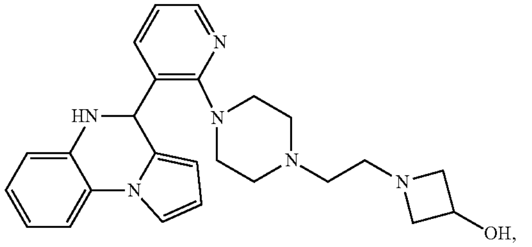

Compound 47

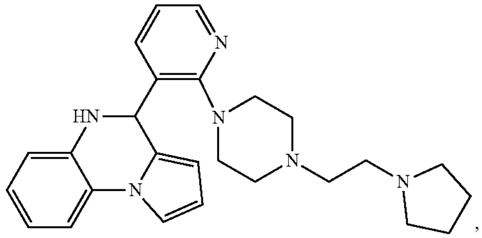

, or

Compound 50

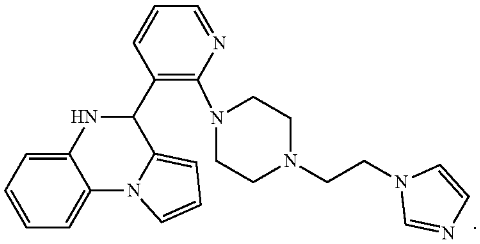

.

In some embodiments, the invention encompasses a method of preparing a compound according to Formula I wherein X=N or $NR^5$ and A=heteroaryl (such as pyridine), said method comprising a synthesis selected from Scheme 1 to Scheme 3.

In some embodiments, the invention encompasses a method of preparing a compound according to Formula I wherein X=O and A=heteroaryl (such as pyridine), said method comprising a synthesis according to Scheme 4.

4.0 EXAMPLES

The following examples are provided solely to illustrate the present invention and are not intended to limit the scope of the invention, described herein.

4.1. Chemistry

All commercially available starting materials and solvents were reagent grade and used without further purification. Reactions were performed under a nitrogen atmosphere in dry glassware with magnetic stirring. Preparative column chromatography was performed using silica gel 60, particle size 0.063-0.200 mm (70-230 mesh, flash). Analytical TLC was carried out employing silica gel 60 F254 plates (Merck, Darmstadt). Visualization of the developed chromatograms was performed with detection by UV (254 nm). NMR spectra were recorded on a Brucker-300 ($^1H$, 300 MHz; $^{13}C$, 75 MHz; $^{19}F$, 282 MHz) spectrometer. $^1H$ and $^{13}C$ NMR spectra were recorded with TMS as an internal reference. Chemical shifts were expressed in ppm, and J values were given in Hz. High-resolution mass spectra (HRMS) were obtained from Thermo Fisher LTQ Orbitrap Elite mass spectrometer. Parameters include the following: Nano ESI spray voltage was 1.8 kV; Capillary temperature was 275° C. and the resolution was 60,000; Ionization was achieved by positive mode. Melting points were measured on a Thermo Scientific Electrothermal Digital Melting Point Apparatus and uncorrected. Purities of final compounds were established by analytical HPLC, which was carried out on a Shimadzu HPLC system (model: CBM-20A LC-20AD SPD-20A UV/VIS). HPLC analysis conditions: Waters μBondapak C18 (300×3.9 mm); flow rate 0.5 mL/min; UV detection at 270 and 254 nm; linear gradient from 10% acetonitrile in water to 100% acetonitrile in water in 20 min followed by 30 min of the last-named solvent (0.1% TFA was added into both acetonitrile and water). All biologically evaluated compounds are >95% pure.

4-(2-Chloropyridin-3-yl)-4,5-dihydropyrrolo[1,2-a]quinoxaline (14)

To a solution of 2-chloronicotinaldehyde (25 mg, 0.16 mmol) and 2-(1H-pyrrol-1-yl)aniline (22 mg, 0.16 mmol) in EtOH (5 mL) was added 3 drops of AcOH. The reaction mixture was stirred at 50° C. for 3 h, and then evaporated in vacuo and purified by silica gel column chromatography ($CH_2Cl_2$/MeOH) to give compound 14 as a pale-yellow foam (29 mg, 69%). $^1H$ NMR (300 MHz, $CDCl_3$) δ 8.31 (dd, J=4.8, 2.1 Hz, 1H), 7.44 (dd, J=7.7, 1.9 Hz, 1H), 7.38 (dd, J=7.9, 1.4 Hz, 1H), 7.29-7.28 (m, 1H), 7.15 (dd, J=7.8, 4.8 Hz, 1H), 6.98 (td, J=7.5, 1.5 Hz, 1H), 6.88 (td, J=7.8, 1.5 Hz, 1H), 6.74 (dd, J=7.8, 1.5 Hz, 1H), 6.36 (t, J=3.3 Hz, 1H), 6.07 (s, 1H), 5.92-5.91 (m, 1H), 4.56 (s, 1H). $^{13}C$ NMR (75 MHz, $CDCl_3$) δ 149.6, 148.9, 148.8, 138.1, 138.0, 136.4, 134.4, 126.1, 125.2, 125.0, 123.1, 123.0, 119.8, 115.9, 114.8, 114.6, 110.6, 110.5, 106.4, 106.1, 51.7, 51.6. HRMS (ESI) calcd for $C_{16}H_{13}ClN_3$, 282.0798 $[M+H]^+$; found, 282.0788.

3-(4,5-Dihydropyrrolo[1,2-a]quinoxalin-4-yl)-N,N-dimethylpyridin-2-amine (15)

To a solution of 2-chloronicotinaldehyde (141 mg, 1.0 mmol) in toluene (5 mL) was added dimethylamine hydrochloride (162 mg, 2.0 mmol) and $K_2CO_3$ (276 mg, 2.0 mmol). The reaction mixture was stirred at 110° C. overnight, and then evaporated in vacuo and purified by silica gel column chromatography ($CH_2Cl_2$/EtOAc) to give 2-(dimethylamino)nicotinaldehyde (11a) as yellow oil (130 mg, 86%). $^1$H NMR (300 MHz, $CDCl_3$) δ 9.92 (s, 1H), 8.27 (dd, J=4.6, 2.0 Hz, 1H), 7.90 (dd, J=7.6, 2.0 Hz, 1H), 6.74 (dd, J=7.6, 4.7 Hz, 1H), 3.09 (s, 6H).

To a solution of 11a (40 mg, 0.27 mmol) and 2-(1H-pyrrol-1-yl)aniline (48 mg, 0.3 mmol) in EtOH (5 mL) was added 3 drops of AcOH. The reaction mixture was stirred at 50° C. for 3 h, and then evaporated in vacuo and purified by silica gel column chromatography ($CH_2Cl_2$/MeOH) to give compound 15 as a pale-yellow foam (43 mg, 74%). $^1$H NMR (300 MHz, $CDCl_3$) δ 8.28 (dd, J=4.8, 2.1 Hz, 1H), 7.64 (dd, J=7.5, 1.8 Hz, 1H), 7.36 (dd, J=7.8, 1.5 Hz, 1H), 7.25 (dd, J=3.0, 1.5 Hz, 1H), 6.98-6.83 (m, 3H), 6.69 (dd, J=7.8, 1.5 Hz, 1H), 6.33 (t, J=3.3 Hz, 1H), 5.89 (s, 1H), 5.80 (dd, J=3.5, 1.5 Hz, 1H), 4.60 (s, 1H), 2.90 (s, 6H). $^{13}$C NMR (75 MHz, $CDCl_3$) δ 162.3, 147.3, 138.8, 136.5, 128.9, 128.4, 125.8, 124.7, 119.6, 118.5, 115.7, 114.9, 114.8, 110.0, 106.2, 50.8, 43.5. HRMS (ESI) calcd for $C_{18}H_{19}N_4$, 291.1610 $[M+H]^+$; found, 291.1599.

4-(2-(Azetidin-1-yl)pyridin-3-yl)-4,5-dihydropyrrolo[1,2-a]quinoxaline (16)

Compound 16 was prepared by following a procedure similar to that used to prepare compound 15, starting from 2-chloronicotinaldehyde, azetidine hydrochloride, and 2-(1H-pyrrol-1-yl)aniline. The title compound (21 mg, 35%) was obtained as a pale-yellow foam. $^1$H NMR (300 MHz, $CDCl_3$) δ 8.17 (dd, J=4.8, 1.8 Hz, 1H), 7.42 (dd, J=7.5, 1.8 Hz, 1H), 7.34 (dd, J=7.8, 1.5 Hz, 1H), 7.24 (dd, J=3.0, 1.5 Hz, 1H), 6.96 (td, J=7.5, 1.5 Hz, 1H), 6.85 (td, J=7.5, 1.5 Hz, 1H), 6.74-6.65 (m, 2H), 6.33 (t, J=3.3 Hz, 1H), 5.84 (ddd, J=3.6, 1.5, 0.9 Hz, 1H), 4.44 (s, 1H), 4.28 (q, J=7.5 Hz, 2H), 4.07 (q, J=7.5 Hz, 2H), 2.34 (p, J=7.5 Hz, 2H). $^{13}$C NMR (75 MHz, $CDCl_3$) δ 158.9, 147.3, 137.6, 135.8, 128.6, 125.5, 124.7, 122.5, 119.5, 115.9, 114.9, 114.7, 114.6, 110.1, 106.4, 52.9, 50.5, 17.2. HRMS (ESI) calcd for $C_{19}H_{19}N_4$, 303.1610 $[M+H]^+$; found, 303.1598.

1-(3-(4,5-Dihydropyrrolo[1,2-a]quinoxalin-4-yl)pyridin-2-yl)azetidin-3-ol (17)

Compound 17 was prepared by following a procedure similar to that used to prepare compound 15, starting from 2-chloronicotinaldehyde, 3-hydroxyazetidine hydrochloride, and 2-(1H-pyrrol-1-yl)aniline. The title compound (19 mg, 30%) was obtained as a white foam. $^1$H NMR (300 MHz, $CDCl_3$) δ 8.15 (dd, J=4.8, 1.8 Hz, 1H), 7.47 (dd, J=7.5, 1.8 Hz, 1H), 7.34 (dd, J=7.8, 1.5 Hz, 1H), 7.23 (dd, J=3.0, 1.5 Hz, 1H), 6.96 (td, J=7.6, 1.5 Hz, 1H), 6.86 (td, J=7.8, 1.5 Hz, 1H), 6.73-6.69 (m, 2H), 6.31 (t, J=3.3 Hz, 1H), 5.79 (dd, J=3.3, 1.5 Hz, 1H), 5.60 (s, 1H), 4.69 (tt, J=6.5, 4.8 Hz, 1H), 4.50-4.40 (m, 2H), 4.27 (dd, J=8.7, 6.5 Hz, 1H), 4.09 (dd, J=8.7, 4.8 Hz, 1H), 3.89 (ddd, J=8.7, 4.5, 1.2 Hz, 1H), 2.63 (s, 1H). $^{13}$C NMR (75 MHz, $CDCl_3$) δ 158.5, 147.2, 138.0, 135.8, 128.5, 125.5, 124.8, 122.8, 119.7, 115.9, 115.4, 114.8, 114.6, 110.2, 106.5, 62.7, 62.5, 62.0, 50.7. HRMS (ESI) calcd for $C_{19}H_{19}N_4O$, 319.1559 $[M+H]^+$; found, 319.1545.

4-(2-(Pyrrolidin-1-yl)pyridin-3-yl)-4,5-dihydropyrrolo[1,2-a]quinoxaline (18)

To a solution of 2-chloronicotinaldehyde (141 mg, 1.0 mmol) in toluene (5 mL) was added pyrrolidine (261 mg, 3.0 mmol). The reaction mixture was stirred at 110° C. overnight, and then evaporated in vacuo and purified by silica gel column chromatography ($CH_2Cl_2$/EtOAc) to give 2-(pyrrolidin-1-yl)nicotinaldehyde (11d) as yellow oil (75 mg, 42%). $^1$H NMR (300 MHz, $CDCl_3$) δ 9.98 (s, 1H), 8.29 (dd, J=4.6, 2.0 Hz, 1H), 7.91 (dd, J=7.7, 2.0 Hz, 1H), 6.67 (dd, J=7.6, 4.6 Hz, 1H), 3.56-3.47 (m, 4H), 2.01-1.90 (m, 4H).

Compound 18 was prepared by following a procedure similar to that used to prepare compound 15, starting from 11d and 2-(1H-pyrrol-1-yl)aniline. The title compound (18 mg, 29%) was obtained as a pale-yellow foam. $^1$H NMR (300 MHz, $CDCl_3$) δ 8.19 (dd, J=4.8, 1.8 Hz, 1H), 7.66 (dd, J=7.5, 1.8 Hz, 1H), 7.35 (dd, J=7.8, 1.5 Hz, 1H), 7.24 (dd, J=3.0, 1.5 Hz, 1H), 6.96 (td, J=7.5, 1.5 Hz, 1H), 6.85 (td, J=7.5, 1.5 Hz, 1H), 6.77-6.70 (m, 2H), 6.33 (t, J=3.2 Hz, 1H), 5.84-5.81 (m, 2H), 4.19 (s, 1H), 3.73-3.64 (m, 2H), 3.45-3.38 (m, 2H), 2.03-1.86 (m, 4H). $^{13}$C NMR (75 MHz, $CDCl_3$) δ 158.6, 146.9, 138.8, 136.5, 129.7, 125.8, 124.7, 123.7, 119.6, 115.7, 115.3, 114.8, 114.7, 110.0, 106.6, 51.1, 50.9, 25.6. HRMS (ESI) calcd for $C_{20}H_{21}N_4$, 317.1766 $[M+H]^+$; found, 317.1753.

4-(2-(4-Methyl-1,4-diazepan-1-yl)pyridin-3-yl)-4,5-dihydropyrrolo[1,2-a]quinoxaline (19)

To a solution of 2-chloronicotinaldehyde (141 mg, 1.0 mmol) and 1-methylhomopiperazine (228 mg, 2.0 mmol) in DMF (5 mL) was added $K_2CO_3$ (414 mg, 3.0 mmol) and 18-crown-6 (132 mg, 0.5 mmol). The reaction mixture was stirred at 100° C. overnight. Then the mixture was diluted with EtOAc, washed with $H_2O$, dried over $Na_2SO_4$, and concentrated. The residue was purified by silica gel column chromatography ($CH_2Cl_2$/EtOAc) to give 2-(4-methyl-1,4-diazepan-1-yl)nicotinaldehyde (lie) as yellow oil (90 mg, 41%). $^1$H NMR (300 MHz, $CDCl_3$) δ 9.90 (s, 1H), 8.29-8.23 (m, 1H), 7.94-7.86 (m, 1H), 6.75-6.68 (m, 1H), 3.82-3.72 (m, 2H), 3.60 (t, J=5.9 Hz, 2H), 2.79-2.71 (m, 2H), 2.58-2.50 (m, 2H), 2.33 (s, 3H), 2.05-1.96 (m, 2H).

Compound 19 was prepared by following a procedure similar to that used to prepare compound 15, starting from lie and 2-(1H-pyrrol-1-yl)aniline. The title compound (27 mg, 37%) was obtained as a pale-yellow foam. $^1$H NMR (300 MHz, $CDCl_3$) δ 8.22 (dd, J=4.8, 1.8 Hz, 1H), 7.52 (dd, J=7.5, 2.1 Hz, 1H), 7.35 (dd, J=7.8, 1.5 Hz, 1H), 7.25 (dd, J=3.0, 1.5 Hz, 1H), 6.96 (td, J=7.5, 1.5 Hz, 1H), 6.88-6.82 (m, 2H), 6.71 (dd, J=7.8, 1.5 Hz, 1H), 6.33 (t, J=3.3 Hz, 1H), 5.83-5.81 (m, 2H), 4.83 (s, 1H), 3.71-3.57 (m, 3H), 3.50-3.42 (m, 1H), 2.95-2.73 (m, 4H), 2.46 (s, 3H), 2.14-1.96 (m, 2H). $^{13}$C NMR (75 MHz, $CDCl_3$) δ 162.1, 147.1, 138.8, 136.2, 128.4, 127.9, 125.7, 124.7, 119.4, 118.1, 115.7, 114.8, 114.8, 110.1, 106.2, 58.6, 57.3, 53.4, 52.6, 50.9, 46.8, 28.0. HRMS (ESI) calcd for $C_{22}H_{26}N_5$, 360.2188 $[M+H]^+$; found, 360.2178.

4-(2-((3aR,6aS)-5-Methylhexahydropyrrolo[3,4-c]pyrrol-2(1H)-yl)pyridin-3-yl)-4,5-dihydropyrrolo[1,2-a]quinoxaline (20)

Compound 20 was prepared by following a procedure similar to that used to prepare compound 18, starting from 2-chloronicotinaldehyde, cis-2-methylhexahydropyrrolo[3,4-c]pyrrole, and 2-(1H-pyrrol-1-yl)aniline. The title compound (21 mg, 28%) was obtained as colorless oil. $^1$H NMR (300 MHz, $CDCl_3$) δ 8.21 (dd, J=4.8, 1.8 Hz, 1H), 7.42 (dd, J=7.5, 1.8 Hz, 1H), 7.33 (dd, J=7.8, 1.5 Hz, 1H), 7.25 (dd, J=3.0, 1.5 Hz, 1H), 6.95 (td, J=7.5, 1.5 Hz, 1H), 6.88-6.80 (m, 2H), 6.72 (dd, J=7.8, 1.5 Hz, 1H), 6.34 (t, J=3.3 Hz, 1H), 5.87-5.85 (m, 2H), 3.65 (dd, J=10.5, 5.7 Hz, 1H), 3.53 (d, J=10.2 Hz, 1H), 3.18-3.10 (m, 2H), 2.99-2.90 (m, 4H), 2.70-2.65 (m, 1H), 2.62-2.57 (m, 1H), 2.44 (s, 3H). $^{13}$C NMR (75 MHz, $CDCl_3$) δ 158.1, 147.2, 138.1, 136.2, 128.2, 127.9, 125.5, 124.8, 119.2, 118.2, 115.7, 114.7, 114.7, 110.0, 106.4, 62.5, 62.4, 57.1, 56.3, 51.2, 42.2, 41.2, 41.2. HRMS (ESI) calcd for $C_{23}H_{26}N_5$, 372.2188 $[M+H]^+$; found, 372.2175.

4-(2-(4-Methylpiperazin-1-yl)pyridin-3-yl)-4,5-dihydropyrrolo[1,2-a]quinoxaline (21)

Compound 21 was prepared by following a procedure similar to that used to prepare compound 18, starting from 2-chloronicotinaldehyde, 1-methylpiperazine, and 2-(1H-pyrrol-1-yl)aniline. The title compound (128 mg, 53%) was obtained as colorless oil. $^1$H NMR (300 MHz, $CDCl_3$) δ 8.27 (dd, J=4.8, 2.0 Hz, 1H), 7.61 (dd, J=7.7, 2.1 Hz, 1H), 7.33 (d, J=6.2 Hz, 1H), 7.22 (d, J=2.7 Hz, 1H), 6.99-6.90 (m, 2H), 6.89-6.80 (m, 1H), 6.70 (d, J=6.9 Hz, 1H), 6.29 (t, J=3.2 Hz, 1H), 5.80 (s, 1H), 5.73 (d, J=4.1 Hz, 1H), 3.43-3.31 (m, 2H), 3.18-3.07 (m, 2H), 2.68-2.46 (m, 4H), 2.33 (s, 3H). $^{13}$C NMR (75 MHz, $CDCl_3$) δ 161.5, 147.7, 138.9, 136.5, 129.3, 128.8, 125.8, 124.8, 119.6, 119.3, 115.7, 115.0, 114.9, 110.2, 106.3, 55.5, 51.6, 50.6, 46.2. HRMS (ESI) calcd for $C_{21}H_{24}N_5$, 346.2032 $[M+H]^+$; found, 346.2026.

1-(4-(3-(4,5-Dihydropyrrolo[1,2-a]quinoxalin-4-yl)pyridin-2-yl)piperazin-1-yl)ethan-1-one (22)

Compound 21 was prepared by following a procedure similar to that used to prepare compound 18, starting from 2-chloronicotinaldehyde, 1-acetylpiperazine, and 2-(1H-pyrrol-1-yl)aniline. The title compound (34 mg, 46%) was obtained as a yellow foam. $^1$H NMR (300 MHz, $CDCl_3$) δ 8.31 (dd, J=4.8, 1.8 Hz, 1H), 7.78 (dd, J=7.5, 1.8 Hz, 1H), 7.37 (dd, J=7.8, 1.2 Hz, 1H), 7.24 (dd, J=3.3, 1.5 Hz, 1H), 7.05-6.95 (m, 2H), 6.88 (td, J=7.8, 1.2 Hz, 1H), 6.73 (dd, J=7.8, 1.5 Hz, 1H), 6.29 (t, J=3.3 Hz, 1H), 5.85 (s, 1H), 5.67 (dd, J=3.3, 1.5 Hz, 1H), 4.46 (s, 1H), 3.81-3.49 (m, 4H), 3.36-3.22 (m, 2H), 3.13-3.01 (m, 2H), 2.11 (s, 3H). $^{13}$C NMR (75 MHz, $CDCl_3$) δ 169.1, 161.0, 147.8, 139.2, 136.3, 129.5, 128.8, 125.7, 124.8, 119.9, 119.7, 115.6, 115.0, 114.9, 110.1, 106.1, 51.7, 51.6, 50.4, 46.4, 41.5, 21.4. HRMS (ESI) calcd for $C_{22}H_{24}N_5O$, 374.1981 $[M+H]^+$; found, 374.1973.

4-(2-(4-(Methylsulfonyl)piperazin-1-yl)pyridin-3-yl)-4,5-dihydropyrrolo[1,2-a]quinoxaline (23)

Compound 23 was prepared by following a procedure similar to that used to prepare compound 18, starting from 2-chloronicotinaldehyde, 1-methylsulfonyl-piperazine, and 2-(1H-pyrrol-1-yl)aniline. The title compound (61 mg, 74%) was obtained as a pale-yellow foam. $^1$H NMR (300 MHz, $CDCl_3$) δ 8.35 (dd, J=4.8, 1.8 Hz, 1H), 7.83 (dd, J=7.5, 1.8 Hz, 1H), 7.39 (dd, J=7.8, 1.5 Hz, 1H), 7.24 (dd, J=3.0, 1.5 Hz, 1H), 7.07 (dd, J=7.5, 4.8 Hz, 1H), 7.01 (td, J=7.5, 1.5 Hz, 1H), 6.91 (td, J=7.8, 1.5 Hz, 1H), 6.75 (dd, J=7.8, 1.5 Hz, 1H), 6.31-6.29 (m, 1H), 5.82 (s, 1H), 5.66-5.64 (m, 1H), 4.29 (s, 1H), 3.46-3.18 (m, 8H), 2.81 (s, 3H). $^{13}$C NMR (75 MHz, $CDCl_3$) δ 160.9, 147.9, 139.3, 136.4, 129.2, 128.8, 125.8, 124.8, 120.1, 119.8, 115.5, 115.0, 115.0, 110.2, 106.1, 51.2, 50.5, 45.9, 34.4. HRMS (ESI) calcd for $C_{21}H_{24}N_5O_2S$, 410.1651 $[M+H]^+$; found, 410.1635.

4-(3-(4,5-Dihydropyrrolo[1,2-a]quinoxalin-4-yl)pyridin-2-yl)morpholine (24)

Compound 24 was prepared by following a procedure similar to that used to prepare compound 18, starting from 2-chloronicotinaldehyde, morpholine, and 2-(1H-pyrrol-1-yl)aniline. The title compound (45 mg, 69%) was obtained as a pale-yellow foam. $^1$H NMR (300 MHz, $CDCl_3$) δ 8.34 (dd, J=4.8, 1.8 Hz, 1H), 7.76 (dd, J=7.5, 1.8 Hz, 1H), 7.38 (dd, J=7.8, 1.4 Hz, 1H), 7.25 (dd, J=3.0, 1.5 Hz, 1H), 7.04-6.97 (m, 2H), 6.89 (td, J=7.5, 1.5 Hz, 1H), 6.74 (dd, J=7.7, 1.5 Hz, 1H), 6.30 (t, J=3.3 Hz, 1H), 5.85 (s, 1H), 5.71-5.69 (m, 1H), 4.47 (s, 1H), 3.93-3.76 (m, 4H), 3.40-3.32 (m, 2H), 3.13-3.05 (m, 2H). $^{13}$C NMR (75 MHz, $CDCl_3$) δ 161.3, 147.8, 139.1, 136.4, 129.3, 128.9, 125.8, 124.8, 119.7, 119.6, 115.6, 115.0, 114.9, 110.1, 106.2, 67.1, 52.1, 50.4. HRMS (ESI) calcd for $C_{20}H_{21}N_4O$, 333.1715 $[M+H]^+$; found, 333.1705.

4-(2-(4,4-Difluoropiperidin-1-yl)pyridin-3-yl)-4,5-dihydropyrrolo[1,2-a]quinoxaline (25)

Compound 25 was prepared by following a procedure similar to that used to prepare compound 15, starting from 2-chloronicotinaldehyde, 4,4-difluoropiperidine hydrochloride, and 2-(1H-pyrrol-1-yl)aniline. The title compound (21 mg, 29%) was obtained as a pale-yellow foam. $^1$H NMR (300 MHz, $CDCl_3$) δ 8.32 (dd, J=4.8, 1.8 Hz, 1H), 7.77 (dd, J=7.5, 1.8 Hz, 1H), 7.38 (dd, J=7.8, 1.5 Hz, 1H), 7.25 (dd, J=3.0, 1.5 Hz, 1H), 7.05-6.97 (m, 2H), 6.90 (td, J=7.8, 1.5 Hz, 1H), 6.74 (dd, J=7.8, 1.5 Hz, 1H), 6.31 (t, J=3.3 Hz, 1H), 5.82 (s, 1H), 5.70-5.68 (m, 1H), 4.35 (s, 1H), 3.49-3.40 (m, 2H), 3.31-3.22 (m, 2H), 2.30-1.97 (m, 4H). $^{13}$C NMR (75 MHz, $CDCl_3$) δ 160.9, 147.8, 147.6, 139.2, 139.0, 136.3, 129.1, 128.8, 125.8, 125.0, 124.8, 121.8, 119.8, 119.7, 118.6, 115.6, 115.1, 115.0, 114.9, 110.2, 110.0, 106.1, 105.9, 50.7, 50.5, 48.8, 34.2 (t, J=23 Hz). HRMS (ESI) calcd for $C_{21}H_{21}F2N_4$, 367.1734 $[M+H]^+$; found, 367.1724.

4-(3-(4,5-Dihydropyrrolo[1,2-a]quinoxalin-4-yl)pyridin-2-yl)thiomorpholine 1,1-dioxide (26)

To a solution of 2-chloronicotinaldehyde (141 mg, 1.0 mmol) and thiomorpholine 1,1-dioxide (135 mg, 1.0 mmol) in DMF (5 mL) was added $K_2CO_3$ (276 mg, 2.0 mmol). The reaction mixture was stirred at 100° C. overnight. Then the mixture was diluted with EtOAc, washed with $H_2O$, dried over $Na_2SO_4$, and concentrated. The residue was purified by silica gel column chromatography ($CH_2Cl_2$/EtOAc) to give 2-(1,1-dioxidothiomorpholino)nicotinaldehyde (111) as a white solid (57 mg, 23%). $^1$H NMR (300 MHz, $CDCl_3$) δ 9.98 (s, 1H), 8.39 (dd, J=4.8, 2.0 Hz, 1H), 8.04 (dd, J=7.6, 2.0 Hz, 1H), 7.06 (dd, J=7.6, 4.7 Hz, 1H), 4.02-3.92 (m, 4H), 3.27-3.20 (m, 4H).

Compound 26 was prepared by following a procedure similar to that used to prepare compound 15, starting from 111 and 2-(1H-pyrrol-1-yl)aniline. The title compound (46 mg, 61%) was obtained as a white solid. $^1$H NMR (300 MHz, $CDCl_3$) δ 8.32 (dd, J=4.8, 1.8 Hz, 1H), 7.90 (dd, J=7.8, 1.8 Hz, 1H), 7.39 (dd, J=7.8, 1.5 Hz, 1H), 7.25 (dd, J=3.0, 1.5 Hz, 1H), 7.11 (dd, J=7.8, 4.8 Hz, 1H), 7.02 (td, J=7.5, 1.5 Hz, 1H), 6.92 (td, J=7.8, 1.5 Hz, 1H), 6.76 (dd, J=7.8, 1.5 Hz, 1H), 6.29 (t, J=3.3 Hz, 1H), 5.76 (s, 1H), 5.57 (dd, J=3.0, 1.5 Hz, 1H), 4.15 (s, 1H), 3.89-3.69 (m, 4H), 3.37-3.28 (m, 2H), 3.10-3.01 (m, 2H). $^{13}$C NMR (75 MHz, $CDCl_3$) δ 159.7, 147.8, 139.8, 136.2, 128.7, 125.7, 125.0, 120.4, 120.1, 115.6, 115.3, 115.0, 110.2, 105.7, 51.1, 50.9, 50.0. HRMS (ESI) calcd for $C_{20}H_{21}N_4O_2S$, 381.1385 $[M+H]^+$; found, 381.1371.

1-(3-(4,5-Dihydropyrrolo[1,2-a]quinoxalin-4-yl)pyridin-2-yl)piperidin-4-ol (27)

Compound 27 was prepared by following a procedure similar to that used to prepare compound 18, starting from 2-chloronicotinaldehyde, 4-hydroxypiperidine, and 2-(1H-pyrrol-1-yl)aniline. The title compound (37 mg, 53%) was obtained as colorless oil. $^1$H NMR (300 MHz, $CDCl_3$) δ 8.28 (dd, J=4.8, 1.8 Hz, 1H), 7.59 (dd, J=7.5, 1.8 Hz, 1H), 7.36 (dd, J=7.8, 1.5 Hz, 1H), 7.25 (dd, J=3.0, 1.5 Hz, 1H), 7.00-6.94 (m, 2H), 6.86 (td, J=7.8, 1.5 Hz, 1H), 6.71 (dd, J=7.8, 1.5 Hz, 1H), 6.32 (t, J=3.2 Hz, 1H), 5.85 (s, 1H), 5.77 (dd, J=3.0, 1.5 Hz, 1H), 4.71 (s, 1H), 3.87 (tt, J=9.0, 4.2 Hz, 1H), 3.53-3.45 (m, 1H), 3.39-3.31 (m, 1H), 3.18 (ddd, J=12.8, 10.2, 3.0 Hz, 1H), 2.90 (ddd, J=12.8, 10.2, 3.0 Hz, 1H), 2.13-1.95 (m, 2H), 1.85-1.63 (m, 3H). $^{13}$C NMR (75 MHz, $CDCl_3$) δ 161.75, 147.54, 138.68, 136.20, 129.84, 128.44, 125.68, 124.78, 119.57, 119.44, 115.64, 114.86, 114.82, 110.08, 106.11, 67.92, 50.57, 48.79, 34.96, 34.89. HRMS (ESI) calcd for $C_{21}H_{23}N_4O$, 347.1872 $[M+H]^+$; found, 347.1864.

4-(2-(4-(Pyridin-2-yl)piperazin-1-yl)pyridin-3-yl)-4,5-dihydropyrrolo[1,2-a]quinoxaline (28)

Compound 28 was prepared by following a procedure similar to that used to prepare compound 18, starting from 2-chloronicotinaldehyde, 1-(2-pyridyl)piperazine, and 2-(1H-pyrrol-1-yl)aniline. The title compound (39 mg, 47%) was obtained as a pale-yellow foam. $^1$H NMR (300 MHz, $CDCl_3$) δ 8.33 (dd, J=4.8, 1.8 Hz, 1H), 8.21 (dd, J=5.0, 2.1 Hz, 1H), 7.73 (dd, J=7.5, 1.8 Hz, 1H), 7.50 (ddd, J=9.0, 7.1, 2.1 Hz, 1H), 7.37 (dd, J=7.8, 1.5 Hz, 1H), 7.25 (dd, J=3.0, 1.5 Hz, 1H), 7.03-6.95 (m, 2H), 6.88 (td, J=7.8, 1.5 Hz, 1H), 6.74-6.63 (m, 3H), 6.33 (t, J=3.3 Hz, 1H), 5.92 (s, 1H), 5.76 (dt, J=3.3, 1.2 Hz, 1H), 4.60 (s, 1H), 3.79-3.72 (m, 2H), 3.65-3.57 (m, 2H), 3.51-3.43 (m, 2H), 3.29-3.21 (m, 2H). $^{13}$C NMR (75 MHz, $CDCl_3$) δ 161.3, 159.6, 147.9, 147.7, 139.0, 137.5, 136.3, 129.4, 128.7, 125.7, 124.8, 119.7, 119.6, 115.6, 115.0, 114.9, 113.6, 110.1, 107.4, 106.2, 51.4, 50.5, 45.7. HRMS (ESI) calcd for $C_{25}H_{25}N_6$, 409.2141 $[M+H]^+$; found, 409.2126.

4-(2-(4-(Pyrrolidin-1-yl)piperidin-1-yl)pyridin-3-yl)-4,5-dihydropyrrolo[1,2-a]quinoxaline (29)

Compound 29 was prepared by following a procedure similar to that used to prepare compound 18, starting from 2-chloronicotinaldehyde, 4-(1-pyrrolidinyl)piperidine, and 2-(1H-pyrrol-1-yl)aniline. The title compound (28 mg, 36%) was obtained as a pale-yellow foam. $^1$H NMR (300 MHz, $CDCl_3$) δ 8.26 (dd, J=4.8, 1.8 Hz, 1H), 7.48 (dd, J=7.5, 1.8 Hz, 1H), 7.33 (dd, J=7.8, 1.5 Hz, 1H), 7.24 (dd, J=3.0, 1.5 Hz, 1H), 6.97-6.89 (m, 2H), 6.85 (dd, J=7.8, 1.5 Hz, 1H), 6.67 (dd, J=7.8, 1.5 Hz, 1H), 6.33 (t, J=3.3 Hz, 1H), 5.84-5.82 (m, 2H), 4.89 (s, 1H), 3.55-3.38 (m, 2H), 3.16 (td, J=12.3, 2.4 Hz, 1H), 2.83 (td, J=12.3, 2.4 Hz, 1H), 2.65-2.61 (m, 4H), 2.24-2.11 (m, 2H), 2.03-1.97 (m, 1H), 1.86-1.67 (m, 6H). $^{13}$C NMR (75 MHz, $CDCl_3$) δ 161.8, 147.5, 138.3, 136.2, 129.9, 128.2, 125.6, 124.8, 119.4, 119.2, 115.6, 114.8, 114.7, 110.0, 106.0, 61.6, 52.7, 51.5, 50.7, 49.1, 32.3, 32.1, 23.3. HRMS (ESI) calcd for $C_{25}H_{30}N_5$, 400.2501 $[M+H]^+$; found, 400.2488.

2-((3-(Pyrrolo[1,2-a]quinoxalin-4-yl)pyridin-2-yl)oxy)ethan-1-amine (30)

To a solution of 2-fluoronicotinaldehyde (500 mg, 4.0 mmol) and N-Boc-ethanolamine (1287 mg, 8.0 mmol) in DMF (10 mL) was added $Na_2CO_3$ (847 mg, 8.0 mmol). The reaction mixture was stirred at 110° C. for 6 h, and then water (50 mL) was added. The mixture was extracted with EtOAc (3×60 mL), washed with water (3×20 mL), dried over $Na_2SO_4$, filtered, concentrated in vacuo and purified by silica gel column chromatography (Hex/EtOAc) to give tert-butyl (2-((3-formylpyridin-2-yl)oxy)ethyl)carbamate (13) as pale-yellow liquid (460 mg, 43%). $^1$H NMR (300 MHz, $CDCl_3$) δ 10.37 (d, J=1.0 Hz, 1H), 8.34 (dd, J=4.9, 2.1 Hz, 1H), 8.11 (dd, J=7.5, 2.1 Hz, 1H), 7.02 (ddd, J=7.4, 4.9, 0.9 Hz, 1H), 4.96 (s, 1H), 4.53 (t, J=5.3 Hz, 2H), 3.59 (q, J=5.6 Hz, 2H), 1.43 (s, 9H).

To a solution of 13 (282 mg, 1.05 mmol) and 2-(1H-pyrrol-1-yl)aniline (158 mg, 1.0 mmol) in EtOH (5 mL) was added 6 drops of AcOH. The reaction mixture was stirred at 50° C. for 8 h, and then evaporated in vacuo and purified by silica gel column chromatography ($CH_2Cl_2$/EtOAc) to give the crude intermediate. The intermediate was dissolved in $CH_2Cl_2$ (5 mL), and TFA (1.14 g, 10 mmol) was slowly added. The resulting mixture was stirred at RT overnight and then treated with saturated $NaHCO_3$ (10 mL). The mixture was extracted with $CH_2Cl_2$ (3×30 mL), dried over $Na_2SO_4$, filtered, concentrated, and purified by silica gel column chromatography ($CH_2Cl_2$/MeOH) to give compound 30 as a pale-yellow foam (101 mg, 33% in two steps). $^1$H NMR (300 MHz, $CDCl_3$) δ 7.99 (dd, J=5.1, 1.8 Hz, 1H), 7.32 (dd, J=7.8, 1.5 Hz, 1H), 7.24 (dd, J=3.0, 1.5 Hz, 1H), 7.09 (dd, J=7.2, 1.8 Hz, 1H), 6.89 (td, J=7.5, 1.5 Hz, 1H), 6.81-6.67 (m, 3H), 6.34 (t, J=3.0 Hz, 1H), 5.94-5.92 (m, 2H), 4.53-4.40 (m, 2H), 3.17-3.12 (m, 2H), 2.12 (s, 2H). $^{13}$C NMR (75 MHz, $CDCl_3$) δ 160.6, 145.8, 136.7, 135.2, 126.5, 125.2, 125.1, 124.7, 119.0, 117.2, 115.7, 114.5, 114.3, 110.2, 105.8, 67.8, 49.4, 41.2. HRMS (ESI) calcd for $C_{18}H_{19}N_4O$, 307.1559 $[M+H]^+$; found, 307.1549.

2-(4-(3-(4,5-Dihydropyrrolo[1,2-a]quinoxalin-4-yl)pyridin-2-yl)piperazin-1-yl)ethan-1-ol (35)

To a solution of 2-chloronicotinaldehyde (141 mg, 1.0 mmol) in toluene (5 mL) was added 2-(piperazin-1-yl)ethan-1-ol (195 mg, 1.5 mmol). The reaction mixture was heated to reflux and stirred for 5 h, and then evaporated in vacuo and purified by silica gel column chromatography ($CH_2Cl_2$/MeOH) to give 2-(4-(2-hydroxyethyl)piperazin-1-yl)nicotinaldehyde (32a) as a yellow solid (53 mg, 23%). $^1$H NMR (300 MHz, $CDCl_3$) δ 9.99 (s, 1H), 8.37 (dd, J=4.8, 2.1 Hz, 1H), 7.99 (dd, J=7.5, 2.1 Hz, 1H), 6.95 (dd, J=7.5, 4.8 Hz, 1H), 3.81-3.77 (m, 2H), 3.61 (t, J=4.8 Hz, 4H), 2.92 (t, J=4.8 Hz, 4H), 2.85-2.79 (m, 2H).

To a solution of 32a (53 mg, 0.23 mmol) and 2-(1H-pyrrol-1-yl)aniline (45 mg, 0.28 mmol) in EtOH (2 mL) was added 1 drops of AcOH. The reaction mixture was stirred at 50° C. for 3 h, and then evaporated in vacuo and purified by silica gel column chromatography ($CH_2Cl_2$/MeOH) to give compound 18 as yellow solid (30 mg, 35%). $^1$H NMR (300 MHz, $CDCl_3$) δ 8.31 (dd, J=4.8, 1.8 Hz, 1H), 7.67 (dd, J=7.5, 1.8 Hz, 1H), 7.37 (dd, J=7.8, 1.5 Hz, 1H), 7.25 (dd, J=3.0, 1.5 Hz, 1H), 7.01-6.95 (m, 2H), 6.88 (td, J=7.8, 1.5 Hz, 1H), 6.72 (dd, J=7.8, 1.5 Hz, 1H), 6.31 (t, J=3.3 Hz, 1H), 5.84 (s, 1H), 5.74 (dt, J=3.4, 1.2 Hz, 1H), 4.58 (s, 1H), 3.67-3.63 (m, 2H), 3.42-3.35 (m, 2H), 3.17-3.10 (m, 2H), 2.78-2.58 (m, 7H). $^{13}$C NMR (75 MHz, $CDCl_3$) δ 161.3, 147.7, 138.9, 136.3, 129.4, 128.7, 125.7, 124.8, 119.6, 119.4, 115.6, 114.9, 114.9, 110.1, 106.2, 59.3, 57.7, 53.1, 51.6, 50.5. HRMS (ESI) calcd for $C_{22}H_{26}N_5O$, 376.2137 $[M+H]^+$; found, 376.2123.

4-(2-(4-(2-Methoxyethyl)piperazin-1-yl)pyridin-3-yl)-4,5-dihydropyrrolo[1,2-a]quinoxaline (36)

Compound 36 was prepared by following a procedure similar to that used to prepare compound 35, starting from 2-chloronicotinaldehyde, 1-(2-methoxyethyl)piperazine, and 2-(1H-pyrrol-1-yl)aniline. The title compound (50 mg, 65%) was obtained as a pale-yellow foam. $^1$H NMR (300 MHz, $CDCl_3$) δ 8.29 (dd, J=4.8, 1.8 Hz, 1H), 7.66 (dd, J=7.5, 1.8 Hz, 1H), 7.36 (dd, J=7.8, 1.5 Hz, 1H), 7.23 (dd, J=3.0, 1.5 Hz, 1H), 6.99-6.93 (m, 2H), 6.86 (td, J=7.8, 1.5 Hz, 1H), 6.71 (dd, J=7.8, 1.5 Hz, 1H), 6.30 (t, J=3.3 Hz, 1H), 5.82 (s, 1H), 5.74 (ddd, J=3.5, 1.5, 0.9 Hz, 1H), 4.60 (s, 1H), 3.55 (t, J=5.7 Hz, 2H), 3.44-3.35 (m, 5H), 3.19-3.12 (m, 2H), 2.74-2.59 (m, 6H). $^{13}$C NMR (75 MHz, $CDCl_3$) δ 161.41, 147.61, 138.83, 136.44, 129.02, 128.82, 125.75, 124.74, 119.56, 119.06, 115.61, 114.89, 114.84, 110.06, 106.18, 70.22, 58.93, 57.97, 53.84, 51.43, 50.51. HRMS (ESI) calcd for $C_{23}H_{28}N_5O$, 390.2294 $[M+H]^+$; found, 390.2281.

4-(2-(4-(3-Methoxypropyl)piperazin-1-yl)pyridin-3-yl)-4,5-dihydropyrrolo[1,2-a]quinoxaline (37)

To a solution of 2-chloronicotinaldehyde (282 mg, 2.0 mmol) in DMF (10 mL) was added piperazine (860 mg, 10.0 mmol). The reaction mixture was stirred at 90° C. overnight, Then the mixture was diluted with EtOAc, washed with $H_2O$, dried over $Na_2SO_4$, and concentrated. The residue was purified by silica gel column chromatography ($CH_2Cl_2$/MeOH) to give 2-(piperazin-1-yl)nicotinaldehyde (31) as a yellow solid.

To a solution of 31 (90 mg, 0.5 mmol) in 5 mL of $CH_3CN$ was added 1-bromo-3-methoxypropane (76 mg, 0.5 mmol) and $K_2CO_3$ (106 mg, 1.0 mmol) The reaction mixture was stirred at 50° C. for 3 h, and then evaporated in vacuo and purified by silica gel column chromatography ($CH_2Cl_2$/MeOH) to give 2-(4-(3-methoxypropyl)piperazin-1-yl)nicotinaldehyde (32d) as a yellow solid (70 mg, 53%).

To a solution of 32d (53 mg, 0.2 mmol) and 2-(1H-pyrrol-1-yl)aniline (32 mg, 0.2 mmol) in EtOH (2 mL) was added 1 drops of AcOH. The reaction mixture was stirred at 50° C. for 3 h, and then evaporated in vacuo and purified by silica gel column chromatography ($CH_2Cl_2$/MeOH) to give compound 37 as yellow solid (45 mg, 56%). $^1$H NMR (300 MHz, $CDCl_3$) δ 8.30 (dd, J=4.8, 1.8 Hz, 1H), 7.68 (dd, J=7.5, 1.8 Hz, 1H), 7.36 (dd, J=7.8, 1.5 Hz, 1H), 7.24 (dd, J=3.0, 1.5 Hz, 1H), 7.00-6.95 (m, 2H), 6.87 (td, J=7.8, 1.5 Hz, 1H), 6.72 (dd, J=7.8, 1.5 Hz, 1H), 6.30 (t, J=3.3 Hz, 1H), 5.81 (s, 1H), 5.72 (dt, J=3.3, 1.2 Hz, 1H), 3.46-3.39 (m, 4H), 3.34 (s, 3H), 3.22-3.14 (m, 2H), 2.77-2.66 (m, 4H), 2.57 (dd, J=9.0, 6.3 Hz, 2H), 1.89-1.79 (m, 2H). $^{13}$C NMR (75 MHz, $CDCl_3$) δ 161.2, 147.6, 138.9, 136.3, 129.1, 128.7, 125.7, 124.8, 119.6, 119.3, 115.6, 114.9, 114.9, 110.1, 106.2, 70.9, 58.6, 55.2, 52.9, 51.0, 50.5, 26.3. HRMS (ESI) calcd for $C_{24}H_{30}N_5O$, 404.2450 $[M+H]^+$; found, 404.2437.

2-(4-(3-(4,5-Dihydropyrrolo[1,2-a]quinoxalin-4-yl)pyridin-2-yl)piperazin-1-yl)-N,N-dimethylethan-1-amine (38)

Compound 38 was prepared by following a procedure similar to that used to prepare compound 35, starting from 2-chloronicotinaldehyde, 1-(2-dimethylaminoethyl)piperazine, and 2-(1H-pyrrol-1-yl)aniline. The title compound (39 mg, 49%) was obtained as a pale-yellow foam. $^1$H NMR (300 MHz, $CDCl_3$) δ 8.29 (dd, J=4.8, 1.8 Hz, 1H), 7.65 (dd, J=7.5, 1.8 Hz, 1H), 7.36 (dd, J=7.8, 1.5 Hz, 1H), 7.23 (dd, J=3.0, 1.5 Hz, 1H), 7.00-6.91 (m, 2H), 6.86 (td, J=7.5, 1.5 Hz, 1H), 6.72 (dd, J=7.8, 1.5 Hz, 1H), 6.30 (t, J=3.3 Hz, 1H), 5.82 (s, 1H), 5.74 (dt, J=3.3, 1.2 Hz, 1H), 4.60 (s, 1H), 3.42-3.35 (m, 2H), 3.17-3.10 (m, 2H), 2.73-2.47 (m, 8H), 2.29 (s, 6H). $^{13}$C NMR (75 MHz, $CDCl_3$) δ 161.4, 147.6, 138.8, 136.4, 129.1, 128.8, 125.7, 124.7, 119.6, 119.1, 115.6, 114.9, 114.8, 110.0, 106.2, 56.8, 56.6, 53.9, 51.5, 50.5, 45.9. HRMS (ESI) calcd for $C_{24}H_{31}N_6$, 403.2610 $[M+H]^+$; found, 403.2599.

2-(4-(3-(4,5-Dihydropyrrolo[1,2-a]quinoxalin-4-yl)pyridin-2-yl)piperazin-1-yl)-N,N-dimethylacetamide (39)

Compound 39 was prepared by following a procedure similar to that used to prepare compound 37, starting from compound 31, 2-chloro-N,N-dimethylacetamide, and 2-(1H-pyrrol-1-yl)aniline. The title compound (37 mg, 44%) was obtained as a pale-yellow solid. $^1$H NMR (300 MHz, $CDCl_3$) δ 8.29 (dd, J=4.8, 1.8 Hz, 1H), 7.64 (dd, J=7.5, 1.8 Hz, 1H), 7.35 (dd, J=7.8, 1.5 Hz, 1H), 7.23 (dd, J=3.0, 1.5 Hz, 1H), 6.99-6.94 (m, 2H), 6.86 (td, J=7.8, 1.5 Hz, 1H), 6.72 (dd, J=7.8, 1.5 Hz, 1H), 6.29 (t, J=3.3 Hz, 1H), 5.82 (s, 1H), 5.73 (ddd, J=3.6, 1.5, 0.9 Hz, 1H), 4.61 (s, 1H), 3.42-3.35 (m, 2H), 3.24 (s, 2H), 3.18-3.11 (m, 5H), 2.95 (s, 3H), 2.79-2.61 (m, 4H). $^{13}$C NMR (75 MHz, $CDCl_3$) δ 169.4, 161.4, 147.6, 138.8, 136.3, 129.4, 128.6, 125.7, 124.8, 119.6, 119.3, 115.6, 114.9, 114.8, 110.0, 106.1, 61.0, 53.4, 51.5, 50.5, 37.2, 35.6. HRMS (ESI) calcd for $C_{24}H_{29}N_6O$, 417.2403 $[M+H]^+$; found, 417.2391.

2-(4-(3-(4,5-Dihydropyrrolo[1,2-a]quinoxalin-4-yl)pyridin-2-yl)piperazin-1-yl)acetonitrile (40)

Compound 40 was prepared by following a procedure similar to that used to prepare compound 37, starting from compound 31, bromoacetonitrile, and 2-(1H-pyrrol-1-yl)aniline. The title compound (58 mg, 78%) was obtained as a pale-yellow solid. $^1$H NMR (300 MHz, $CDCl_3$) δ 8.32 (dd, J=4.8, 1.8 Hz, 1H), 7.77 (dd, J=7.5, 1.8 Hz, 1H), 7.37 (d, J=7.8 Hz, 1H), 7.24 (dd, J=3.0, 1.5 Hz, 1H), 7.04-6.97 (m, 2H), 6.89 (td, J=7.5, 1.5 Hz, 1H), 6.75 (dd, J=7.8, 1.5 Hz, 1H), 6.29 (t, J=3.3 Hz, 1H), 5.82 (s, 1H), 5.68 (d, J=3.3 Hz, 1H), 4.40 (s, 1H), 3.58 (s, 2H), 3.45-3.37 (m, 2H), 3.21-3.14 (m, 2H), 2.84-2.66 (m, 4H). $^{13}$C NMR (75 MHz, $CDCl_3$) δ 161.1, 147.7, 139.2, 136.4, 129.3, 128.9, 125.7, 124.9, 119.7, 119.6, 115.7, 115.0, 114.9, 114.7, 110.0, 106.1, 51.9, 51.2, 50.4, 46.0. HRMS (ESI) calcd for $C_{22}H_{23}N_6$, 378.1984 $[M+H]^+$; found, 371.1972.

2-(4-(3-(4,5-Dihydropyrrolo[1,2-a]quinoxalin-4-yl)pyridin-2-yl)piperazin-1-yl)acetamide (41)

To a solution of compound 40 (39 mg, 0.1 mmol) in 2 mL of t-BuOH was added KOH (23 mg, 0.4 mmol). The reaction mixture was stirred at 110° C. for 1 h. The reaction was evaporated in vacuo and purified by silica gel column chromatography ($CH_2Cl_2$/MeOH) to give compound 41 as yellow solid (15 mg, 39%). $^1$H NMR (300 MHz, $CDCl_3$) δ 8.32 (dd, J=4.8, 1.8 Hz, 1H), 7.70 (dd, J=7.5, 1.8 Hz, 1H), 7.37 (dd, J=7.8, 1.5 Hz, 1H), 7.24 (dd, J=3.0, 1.5 Hz, 1H), 7.08-6.96 (m, 3H), 6.88 (td, J=7.8, 1.5 Hz, 1H), 6.73 (dd, J=7.8, 1.5 Hz, 1H), 6.30 (t, J=3.3 Hz, 1H), 5.84 (s, 1H), 5.71 (d, J=3.6 Hz, 1H), 5.58 (s, 1H), 4.49 (s, 1H), 3.42-3.35 (m, 2H), 3.17-3.09 (m, 4H), 2.82-2.65 (m, 4H). $^{13}$C NMR (75 MHz, $CDCl_3$) δ 173.0, 161.3, 147.7, 139.0, 136.3, 129.7, 128.6, 125.7, 124.8, 119.7, 119.7, 115.6, 115.0, 114.9, 110.1, 106.1, 61.4, 53.8, 51.7, 50.4. HRMS (ESI) calcd for $C_{22}H_{25}N_6O$, 389.2090 $[M+H]^+$; found, 389.2075.

2-Chloro-1-(4-(3-(4,5-dihydropyrrolo[1,2-a]quinoxalin-4-yl)pyridin-2-yl)piperazin-1-yl)ethan-1-one (42)

To a solution of 2-(piperazin-1-yl)nicotinaldehyde (38 mg, 0.2 mmol) in 2 mL of $CH_2Cl_2$ was added 2-chloroacetyl chloride (34 mg, 0.3 mmol) and $K_2CO_3$ (55 mg, 0.4 mmol) at 0° C. The reaction mixture was stirred at 0° C. for 1 h, and then evaporated in vacuo and purified by silica gel column chromatography ($CH_2Cl_2$/MeOH) to give 2-(4-(2-chloroacetyl)piperazin-1-yl)nicotinaldehyde (32g) as yellow oil. $^1$H NMR (300 MHz, $CDCl_3$) δ 10.02 (s, 1H), 8.40 (dd, J=4.8, 2.1 Hz, 1H), 8.02 (dd, J=7.5, 2.1 Hz, 1H), 7.00 (dd, J=7.5, 4.8 Hz, 1H), 4.12 (s, 2H), 3.83-3.71 (m, 4H), 3.56-3.45 (m, 4H).

Compound 42 was prepared by following a procedure similar to that used to prepare compound 37, starting from compound 32g and 2-(1H-pyrrol-1-yl)aniline. The title compound (41 mg, 51%) was obtained as a pale-yellow foam. $^1$H NMR (300 MHz, $CDCl_3$) δ 8.33 (dd, J=4.8, 1.8 Hz, 1H), 7.81 (dd, J=7.5, 1.8 Hz, 1H), 7.38 (dd, J=7.8, 1.5 Hz, 1H), 7.24 (dd, J=3.0, 1.5 Hz, 1H), 7.07-6.975 (m, 2H), 6.89 (td, J=7.8, 1.5 Hz, 1H), 6.74 (dd, J=7.8, 1.5 Hz, 1H), 6.30 (t, J=3.3 Hz, 1H), 5.85 (s, 1H), 5.66 (dt, J=3.3, 1.2 Hz, 1H), 4.38 (s, 1H), 4.08 (s, 2H), 3.84-3.54 (m, 4H), 3.42-3.27 (m, 2H), 3.19-3.06 (m, 2H). $^{13}$C NMR (75 MHz, $CDCl_3$) δ 165.1, 160.9, 147.9, 139.3, 136.3, 129.4, 128.8, 125.7, 124.9, 120.1, 119.8, 115.6, 115.0, 114.9, 110.2, 106.1, 51.6, 51.4, 50.4, 46.4, 42.2, 40.9. HRMS (ESI) calcd for $C_{22}H_{23}ClN_5O$, 408.1591 $[M+H]^+$; found, 408.1576.

1-(4-(3-(4,5-Dihydropyrrolo[1,2-a]quinoxalin-4-yl)pyridin-2-yl)piperazin-1-yl)-2-(dimethylamino)ethan-1-one (43)

To a solution of compound 42 (41 mg, 0.1 mmol) in 2 mL of DMF was added dimethylamine (0.15 mL, 0.2 mmol, 2 M in THF) and $K_2CO_3$ (41 mg, 0.3 mmol). The reaction mixture was stirred at 50° C. for 4 h, and then evaporated in vacuo and purified by silica gel column chromatography ($CH_2Cl_2$/MeOH) to give compound 43 as a pale-yellow foam (20 mg, 48%). $^1$H NMR (300 MHz, $CDCl_3$) δ 8.32 (dd, J=4.8, 1.8 Hz, 1H), 7.77 (dd, J=7.56, 1.8 Hz, 1H), 7.38 (dd, J=7.8, 1.5 Hz, 1H), 7.25 (dd, J=3.0, 1.5 Hz, 1H), 7.05-6.96 (m, 2H), 6.89 (td, J=7.8, 1.5 Hz, 1H), 6.74 (dd, J=7.8, 1.5 Hz, 1H), 6.31 (t, J=3.3 Hz, 1H), 5.86 (s, 1H), 5.69 (dt, J=3.6, 1.2 Hz, 1H), 4.42 (s, 1H), 3.86-3.63 (m, 4H), 3.37-3.25 (m, 2H), 3.14-3.05 (m, 4H), 2.29 (s, 6H). $^{13}$C NMR (75 MHz, $CDCl_3$) δ 168.6, 161.1, 147.8, 139.1, 136.3, 129.4, 128.8, 125.7, 124.8, 119.9, 119.8, 115.6, 115.0, 114.9, 110.1, 106.1, 62.7, 52.2, 51.6, 50.4, 45.7, 45.5, 41.9. HRMS (ESI) calcd for $C_{24}H_{29}N_6O$, 417.2403 $[M+H]^+$; found, 417.2391.

(4-(3-(4,5-Dihydropyrrolo[1,2-a]quinoxalin-4-yl)pyridin-2-yl)piperazin-1-yl)(3-hydroxyazetidin-1-yl)methanone (44)

To a solution of 2-(piperazin-1-yl)nicotinaldehyde (31) (191 mg, 1.0 mmol) in 2 mL of $CH_2Cl_2$ was added 4-nitrophenyl carbonochloridate (201 mg, 1.0 mmol) and $Et_3N$ (202 mg, 2.0 mmol) at 0° C. The reaction mixture was stirred at RT overnight, and then evaporated in vacuo to give the intermediate 4-nitrophenyl 4-(3-formylpyridin-2-yl)piperazine-1-carboxylate as a yellow solid (160 mg, 45%). $^1$H NMR (300 MHz, $CDCl_3$) δ 10.07 (s, 1H), 8.44 (dd, J=4.8, 2.1 Hz, 1H), 8.28 (d, J=9.0 Hz, 2H), 8.06 (dd, J=7.5, 2.1 Hz, 1H), 7.35 (d, J=9.0 Hz, 2H), 7.03 (dd, J=7.5, 4.8 Hz, 1H), 3.92-3.79 (m, 4H), 3.58-3.55 (m, 4H).

To a solution of this intermediate (71 mg, 0.2 mmol) in 5 mL of $CH_3CN$ was added 3-hydroxyazetidine hydrochloride (66 mg, 0.6 mmol) and $K_2CO_3$ (83 mg, 0.6 mmol). The reaction mixture was stirred at 60° C. overnight, and then evaporated in vacuo and purified by silica gel column chromatography ($CH_2Cl_2$/MeOH) to give 2-(4-(3-hydroxyazetidine-1-carbonyl)piperazin-1-yl)nicotinaldehyde (32h) as yellow oil (15 mg, 26%). $^1$H NMR (300 MHz, $CDCl_3$) δ 10.01 (s, 1H), 8.38 (dd, J=4.8, 2.1 Hz, 1H), 8.01 (dd, J=7.5, 2.1 Hz, 1H), 6.96 (dd, J=7.5, 4.8 Hz, 1H), 4.64-4.60 (m, 1H), 4.24 (dd, J=9.1, 6.9 Hz, 2H), 3.93-3.88 (m, 2H), 3.55-3.43 (m, 9H).

Compound 44 was prepared by following a procedure similar to that used to prepare compound 37, starting from compound 32h and 2-(1H-pyrrol-1-yl)aniline. The title compound (16 mg, 74%) was obtained as a pale-yellow solid. $^1$H NMR (300 MHz, $CDCl_3$) δ 8.29 (dd, J=4.8, 1.8 Hz, 1H), 7.74 (dd, J=7.5, 1.8 Hz, 1H), 7.36 (dd, J=7.8, 1.5 Hz, 1H), 7.24 (dd, J=3.0, 1.5 Hz, 1H), 7.04-6.95 (m, 2H), 6.88 (td, J=7.5, 1.5 Hz, 1H), 6.73 (dd, J=7.8, 1.5 Hz, 1H), 6.29 (t, J=3.3 Hz, 1H), 5.84 (s, 1H), 5.68 (d, J=3.6 Hz, 1H), 4.61-4.48 (m, 2H), 4.23-4.18 (m, 2H), 3.90-3.85 (m, 2H), 3.57-3.36 (m, 4H), 3.31-3.23 (m, 2H), 3.08-3.01 (m, 2H). $^{13}$C NMR (75 MHz, $CDCl_3$) δ 162.4, 161.1, 147.7, 139.2, 136.3, 129.6, 128.7, 125.7, 124.8, 119.9, 119.7, 115.6, 115.0, 114.9, 110.1, 106.1, 61.8, 61.0, 51.6, 50.4, 44.8. HRMS (ESI) calcd for $C_{24}H_{27}N_6O_2$, 431.2195 $[M+H]^+$; found, 431.2184.

4-(2-(4-(2-(Azetidin-1-yl)ethyl)piperazin-1-yl)pyridin-3-yl)-4,5-dihydropyrrolo[1,2-a]quinoxaline (45)

To a solution of 2-(4-(2-hydroxyethyl)piperazin-1-yl)nicotinaldehyde (32a) (1.31 g, 5.57 mmol) in 60 mL of $CH_2Cl_2$ was added $SOCl_2$ (796 mg, 6.69 mmol). The reaction mixture was stirred at 50° C. for 2 h, and then evaporated in vacuo and purified by silica gel column chromatography ($CH_2Cl_2$/EtOAc) to give 2-(4-(2-chloroethyl)piperazin-1-yl)nicotinaldehyde (33) as a yellow oil (560 mg, 40%). $^1$H NMR (300 MHz, $CDCl_3$) δ 10.02 (s, 1H), 8.38 (dd, J=4.8, 2.1 Hz, 1H), 7.99 (dd, J=7.5, 2.1 Hz, 1H), 6.92 (dd, J=7.5, 4.8 Hz, 1H), 3.63 (t, J=6.9 Hz, 2H), 3.53-3.49 (m, 4H), 2.81 (t, J=6.9 Hz, 2H), 2.72-2.69 (m, 4H).

To a solution of compound 33 (51 mg, 0.2 mmol) in 2 mL of EtOH was added azetidine hydrochloride (56 mg, 0.6 mmol) and $Cs_2CO_3$ (196 mg, 0.6 mmol). The reaction mixture was stirred at 70° C. for 2 h, and then evaporated in vacuo and purified by silica gel column chromatography ($CH_2Cl_2$/MeOH) to give 2-(4-(2-(azetidin-1-yl)ethyl)piperazin-1-yl)nicotinaldehyde (34a) as yellow oil (41 mg, 74%). $^1$H NMR (300 MHz, $CDCl_3$) δ 10.01 (s, 1H), 8.37 (dd, J=4.8, 2.1 Hz, 1H), 7.98 (dd, J=7.5, 2.1 Hz, 1H), 6.90 (dd, J=7.5, 4.8 Hz, 1H), 3.73-3.70 (m, 4H), 3.51-3.48 (m, 4H), 2.70-2.49 (m, 10H).

To a solution of 34a (41 mg, 0.15 mmol) and 2-(1H-pyrrol-1-yl)aniline (36 mg, 0.23 mmol) in EtOH (4 mL) was added 2 drops of AcOH. The reaction mixture was stirred at 50° C. for 3 h, and then evaporated in vacuo and purified by silica gel column chromatography ($CH_2Cl_2$/MeOH) to give compound 45 as a pale-yellow foam (40 mg, 64%). $^1$H NMR (300 MHz, $CDCl_3$) δ 8.30 (dt, J=4.8, 1.5 Hz, 1H), 7.66 (dt, J=7.5, 1.5 Hz, 1H), 7.36 (d, J=7.8 Hz, 1H), 7.24 (dt, J=3.0, 1.5 Hz, 1H), 7.00-6.95 (m, 2H), 6.90-6.84 (m, 1H), 6.72 (dd, J=7.8, 1.5 Hz, 1H), 6.31 (td, J=3.3, 1.2 Hz, 1H), 5.82 (s, 1H), 5.74 (d, J=3.3 Hz, 1H), 4.59 (s, 1H), 3.72 (t, J=4.8 Hz, 4H), 3.41-3.34 (m, 2H), 3.20-3.16-3.09 (m, 2H), 2.74-2.49 (m, 10H). $^{13}$C NMR (75 MHz, $CDCl_3$) δ 161.4, 147.6, 138.8, 136.4, 129.2, 128.7, 125.7, 124.7, 119.6, 119.2, 115.6, 114.9, 114.8, 110.1, 106.2, 67.0, 56.3, 55.7, 54.2, 53.9, 51.6, 50.5. HRMS (ESI) calcd for $C_{25}H_{31}N_6$, 415.2610 [M+H]$^+$; found, 415.2598.

1-(2-(4-(3-(4,5-Dihydropyrrolo[1,2-a]quinoxalin-4-yl)pyridin-2-yl)piperazin-1-yl)ethyl)azetidin-3-ol (46)

Compound 46 was prepared by following a procedure similar to that used to prepare compound 45, starting from compound 33, 3-hydroxyazetidine hydrochloride, and 2-(1H-pyrrol-1-yl)aniline. The title compound (11 mg, 20%) was obtained as a pale-yellow foam. $^1$H NMR (300 MHz, $CDCl_3$) δ 8.29 (dd, J=4.8, 1.8 Hz, 1H), 7.65 (dd, J=7.5, 1.8 Hz, 1H), 7.36 (dd, J=7.8, 1.5 Hz, 1H), 7.24 (dd, J=3.0, 1.5 Hz, 1H), 7.00-6.94 (m, 2H), 6.87 (td, J=7.8, 1.5 Hz, 1H), 6.72 (dd, J=7.8, 1.5 Hz, 1H), 6.30 (t, J=3.3 Hz, 1H), 5.81 (s, 1H), 5.73 (dd, J=3.0, 1.8 Hz, 1H), 4.59 (s, 1H), 4.47 (p, J=5.7 Hz, 1H), 3.75 (td, J=6.3, 1.8 Hz, 2H), 3.52-3.49 (m, 1H), 3.40-3.33 (m, 2H), 3.15-3.04 (m, 4H), 2.72-2.58 (m, 6H), 2.48-2.44 (m, 2H). $^{13}$C NMR (75 MHz, $CDCl_3$) δ 161.3, 147.6, 138.8, 136.3, 129.3, 128.7, 125.7, 124.7, 119.6, 119.3, 115.6, 114.9, 114.8, 110.1, 106.2, 64.7, 62.7, 56.3, 56.3, 53.7, 51.5, 50.5. HRMS (ESI) calcd for $C_{25}H_{31}N_6O$, 431.2559 [M+H]$^+$; found, 431.2546.

4-(2-(4-(2-(Pyrrolidin-1-yl)ethyl)piperazin-1-yl)pyridin-3-yl)-4,5-dihydropyrrolo[1,2-a]quinoxaline (47)

Compound 47 was prepared by following a procedure similar to that used to prepare compound 45, starting from compound 33, pyrrolidine, and 2-(1H-pyrrol-1-yl)aniline. The title compound (47 mg, 54%) was obtained as a pale-yellow foam. $^1$H NMR (300 MHz, $CDCl_3$) δ 8.29 (dd, J=4.8, 1.8 Hz, 1H), 7.65 (dd, J=7.5, 1.8 Hz, 1H), 7.36 (dd, J=7.5, 1.2 Hz, 1H), 7.24 (dd, J=3.0, 1.5 Hz, 1H), 7.00-6.93 (m, 2H), 6.87 (td, J=7.8, 1.5 Hz, 1H), 6.72 (dd, J=7.8, 1.5 Hz, 1H), 6.30 (t, J=3.3 Hz, 1H), 5.82 (s, 1H), 5.75-5.74 (m, 1H), 4.60 (s, 1H), 3.42-3.35 (m, 2H), 3.17-3.09 (m, 2H), 2.75-2.53 (m, 12H), 1.83-1.74 (m, 4H). $^{13}$C NMR (75 MHz, $CDCl_3$) δ 161.42, 147.62, 138.80, 136.38, 129.16, 128.74, 125.73, 124.74, 119.56, 119.13, 115.61, 114.88, 114.83, 110.05, 106.18, 57.71, 54.65, 53.87, 53.69, 51.56, 50.49, 23.40. HRMS (ESI) calcd for $C_{26}H_{33}N_6$, 429.2767 [M+H]$^+$; found, 429.2755.

1-(2-(4-(3-(4,5-Dihydropyrrolo[1,2-a]quinoxalin-4-yl)pyridin-2-yl)piperazin-1-yl)ethyl)pyrrolidin-2-one (48)

To a solution of 2-(piperazin-1-yl)nicotinaldehyde (31) (77 mg, 0.4 mmol) in 5 mL of toluene was added 1-(2-chloroethyl)pyrrolidin-2-one (89 mg, 0.6 mmol) and $Et_3N$ (81 mg, 0.8 mmol). The reaction mixture was heated to reflux and stirred at 50° C. for 3 h, and then evaporated in vacuo and purified by silica gel column chromatography ($CH_2Cl_2$/MeOH) to give 2-(4-(2-(2-oxopyrrolidin-1-yl)ethyl)piperazin-1-yl)nicotinaldehyde (32i) as yellow oil (45 mg, 37%). $^1$H NMR (300 MHz, $CDCl_3$) δ 10.01 (s, 1H), 8.36 (dd, J=4.8, 2.1 Hz, 1H), 7.98 (dd, J=7.5, 2.1 Hz, 1H), 6.90 (dd, J=7.5, 4.8 Hz, 1H), 3.49-3.42 (m, 8H), 2.66-2.63 (m, 4H), 2.57 (t, J=6.6 Hz, 2H), 2.37 (t, J=8.1 Hz, 2H), 2.02 (tt, J=8.1, 6.6 Hz, 2H).

Compound 48 was prepared by following a procedure similar to that used to prepare compound 37, starting from compound 32i and 2-(1H-pyrrol-1-yl)aniline. The title compound (45 mg, 68%) was obtained as a pale-yellow foam. $^1$H NMR (300 MHz, $CDCl_3$) δ 8.29 (dd, J=4.8, 1.8 Hz, 1H), 7.64 (dd, J=7.5, 1.8 Hz, 1H), 7.35 (dd, J=7.8, 1.5 Hz, 1H), 7.23 (dd, J=3.0, 1.5 Hz, 1H), 6.99-6.93 (m, 2H), 6.86 (td, J=7.8, 1.5 Hz, 1H), 6.72 (dd, J=7.8, 1.5 Hz, 1H), 6.30 (t, J=3.3 Hz, 1H), 5.82 (s, 1H), 5.73 (dt, J=3.6, 1.2 Hz, 1H), 4.62 (s, 1H), 3.50-3.31 (m, 6H), 3.13-3.06 (m, 2H), 2.73-2.55 (m, 6H), 2.38 (t, J=8.1 Hz, 2H), 2.06-1.96 (m, 2H). $^{13}$C NMR (75 MHz, $CDCl_3$) δ 175.0, 161.4, 147.6, 138.8, 136.3, 129.5, 128.6, 125.7, 124.8, 119.6, 119.4, 115.6, 114.9, 114.8, 110.1, 106.2, 55.6, 53.3, 51.6, 50.4, 47.8, 39.6, 30.9, 18.0. HRMS (ESI) calcd for $C_{26}H_{31}N_6O$, 443.2559 [M+H]$^+$; found, 443.2549.

4-(2-(4-(3-(4,5-Dihydropyrrolo[1,2-a]quinoxalin-4-yl)pyridin-2-yl)piperazin-1-yl)ethyl)morpholine (49)

Compound 49 was prepared by following a procedure similar to that used to prepare compound 45, starting from compound 33, morpholine, and 2-(1H-pyrrol-1-yl)aniline. The title compound (30 mg, 54%) was obtained as a pale-yellow foam. $^1$H NMR (300 MHz, $CDCl_3$) δ 8.29 (dd, J=4.8, 1.8 Hz, 1H), 7.66 (dd, J=7.5, 1.8 Hz, 1H), 7.36 (dd, J=7.8, 1.5 Hz, 1H), 7.24 (dd, J=3.0, 1.5 Hz, 1H), 7.00-6.94 (m, 2H), 6.86 (td, J=7.5, 1.5 Hz, 1H), 6.71 (dd, J=7.8, 1.5 Hz, 1H), 6.30 (t, J=3.3 Hz, 1H), 5.82 (s, 1H), 5.74-5.72 (m, 1H), 4.60 (d, J=1.6 Hz, 1H), 3.72-3.70 (m, 4H), 3.41-3.34 (m, 2H), 3.16-3.08 (m, 2H), 2.74-2.49 (m, 12H). $^{13}$C NMR (75 MHz, $CDCl_3$) δ 161.4, 147.6, 138.9, 136.4, 129.2, 128.8, 125.7, 124.7, 119.6, 119.2, 115.6, 114.9, 114.8, 110.1, 106.2, 67.0, 56.3, 55.7, 54.2, 53.9, 51.6, 50.5. HRMS (ESI) calcd for $C_{26}H_{33}N_6O$, 445.2716 [M+H]$^+$; found, 445.2703.

4-(2-(4-(2-(1H-Imidazol-1-yl)ethyl)piperazin-1-yl)pyridin-3-yl)-4,5-dihydropyrrolo[1,2-a]quinoxaline (50)

1H-imidazole (41 mg, 0.6 mmol) was dissolved in 5 mL of toluene, NaOH (12 mg, 0.6 mmol) and TBAB (65 mg, 0.2 mmol) were added. The mixture was stirred for 15 min followed by adding 2-(4-(2-chloroethyl)piperazin-1-yl)nicotinaldehyde 33 (51 mg, 0.2 mmol). The reaction mixture was stirred 110° C. for 6 h, and then evaporated in vacuo and purified by silica gel column chromatography ($CH_2Cl_2$/MeOH) to give 2-(4-(2-(1H-imidazol-1-yl)ethyl)piperazin-1-yl)nicotinaldehyde (34e) as yellow oil (40 mg, 70%). $^1$H NMR (300 MHz, $CDCl_3$) δ 9.96 (s, 1H), 8.33 (dd, J=4.8, 2.0 Hz, 1H), 7.94 (dd, J=7.6, 2.0 Hz, 1H), 7.56 (s, 1H), 7.09-6.92 (m, 2H), 6.88 (dd, J=7.5, 4.8 Hz, 1H), 4.05 (t, J=6.4 Hz, 2H), 3.51-3.39 (m, 4H), 2.73 (t, J=6.4 Hz, 2H), 2.66-2.55 (m, 4H).

Compound 50 was prepared by following a procedure similar to that used to prepare compound 45, starting from compound 34e and 2-(1H-pyrrol-1-yl)aniline. The title compound (21 mg, 25%) was obtained as a pale-yellow foam. $^1$H NMR (300 MHz, $CDCl_3$) δ 8.31 (dd, J=4.8, 1.8 Hz, 1H), 7.68 (dd, J=7.5, 1.8 Hz, 1H), 7.55 (s, 1H), 7.37 (dd, J=7.8, 1.2 Hz, 1H), 7.24 (dd, J=3.0, 1.5 Hz, 1H), 7.06 (s, 1H), 7.01-6.96 (m, 3H), 6.91-6.85 (m, 1H), 6.73 (dd, J=7.8, 1.5 Hz, 1H), 6.31 (t, J=3.3 Hz, 1H), 5.82 (s, 1H), 5.74-5.72 (m, 1H), 4.55 (s, 1H), 4.07 (t, J=6.3 Hz, 2H), 3.40-3.34 (m, 2H), 3.15-3.10 (m, 2H), 2.79-2.57 (m, 6H). $^{13}$C NMR (75 MHz, $CDCl_3$) δ 161.3, 147.7, 138.9, 137.3, 136.3, 129.3, 129.3, 128.7, 125.7, 124.8, 119.6, 119.5, 119.3, 115.6, 114.9, 114.9, 110.1, 106.2, 58.7, 53.5, 51.6, 50.4, 44.7. HRMS (ESI) calcd for $C_{25}H_{28}N_7$, 426.2406 [M+H]$^+$; found, 426.2400.

2-(4-(3-(4,5-Dihydropyrrolo[1,2-a]quinoxalin-4-yl) pyridin-4-yl)piperazin-1-yl)-N,N-dimethylethan-1-amine (60)

To a solution of 4-chloronicotinaldehyde (70 mg, 0.5 mmol) and N,N-dimethyl-2-(piperazin-1-yl)ethan-1-amine (118 mg, 0.75 mmol) in 5 mL of toluene was stirred at 110° C. for 4 h. The reaction mixture was evaporated in vacuo and purified by silica gel column chromatography ($CH_2Cl_2$/MeOH) to give the intermediate 4-(4-(2-(dimethylamino) ethyl)piperazin-1-yl)nicotinaldehyde (51a) as pale yellow oil (53 mg, 20%). $^1H$ NMR (300 MHz, $CDCl_3$) δ 9.99 (s, 1H), 8.70 (s, 1H), 8.40 (d, J=6.0 Hz, 1H), 6.79 (d, J=6.0 Hz, 1H), 3.34-3.26 (m, 4H), 2.72-2.63 (m, 4H), 2.58-2.53 (m, 2H), 2.49-2.44 (m, 2H), 2.25 (s, 6H).

To a solution of compound 51a (53 mg, 0.2 mmol) and 2-(1H-pyrrol-1-yl)aniline (47 mg, 0.3 mmol) in EtOH (5 mL) was added 1 drops of AcOH. The reaction mixture was stirred at 50° C. for 3 h, and then evaporated in vacuo and purified by silica gel column chromatography ($CH_2Cl_2$/MeOH) to give compound 36 as a pale-yellow foam (53 mg, 67%). $^1H$ NMR (300 MHz, $CDCl_3$) δ 8.59 (s, 1H), 8.44 (d, J=5.4 Hz, 1H), 7.37 (dd, J=7.8, 1.5 Hz, 1H), 7.23 (dd, J=3.0, 1.5 Hz, 1H), 7.01-6.85 (m, 3H), 6.74 (dd, J=7.8, 1.5 Hz, 1H), 6.29 (t, J=3.3 Hz, 1H), 5.84 (s, 1H), 5.69 (dt, J=3.5, 1.2 Hz, 1H), 4.41 (s, 1H), 3.30-3.23 (m, 2H), 3.01-2.94 (m, 2H), 2.65-2.51 (m, 6H), 2.46-2.41 (m, 2H), 2.25 (s, 6H). $^{13}C$ NMR (75 MHz, $CDCl_3$) δ 158.0, 152.4, 150.2, 136.5, 129.8, 128.7, 125.8, 124.7, 119.7, 115.5, 115.0, 114.9, 113.5, 110.1, 106.2, 56.9, 56.5, 53.6, 52.4, 49.1, 45.9. HRMS (ESI) calcd for $C_{24}H_{31}N_6$, 403.2610 $[M+H]^+$; found, 403.2599.

2-(4-(3-(4,5-Dihydropyrrolo[1,2-a]quinoxalin-4-yl) pyrazin-2-yl)piperazin-1-yl)-N,N-dimethylethan-1-amine (61)

Compound 61 was prepared by following a procedure similar to that used to prepare compound 60, starting from 3-chloro-2-pyrazinecarboxaldehyde, N,N-dimethyl-2-(piperazin-1-yl)ethan-1-amine, and 2-(1H-pyrrol-1-yl)aniline. The title compound (32 mg, 39%) was obtained as a pale-yellow foam. $^1H$ NMR (300 MHz, $CDCl_3$) δ 8.20 (q, J=2.4 Hz, 2H), 7.36 (dd, J=7.8, 1.5 Hz, 1H), 7.23 (dd, J=3.0, 1.5 Hz, 1H), 6.99-6.85 (m, 2H), 6.77 (dd, J=7.8, 1.5 Hz, 1H), 6.30 (t, J=3.3 Hz, 1H), 5.94 (d, J=2.1 Hz, 1H), 5.73 (dt, J=3.6, 1.2 Hz, 1H), 4.45 (s, 1H), 3.43-3.38 (m, 2H), 3.26-3.19 (m, 2H), 2.69-2.36 (m, 8H), 2.27 (s, 6H). $^{13}C$ NMR (75 MHz, $CDCl_3$) δ 157.2, 147.9, 141.2, 138.3, 135.7, 127.2, 126.3, 124.6, 119.9, 116.4, 114.8, 114.7, 110.3, 105.7, 56.9, 56.7, 53.5, 52.5, 50.8, 46.0. HRMS (ESI) calcd for $C_{23}H_{30}N_7$, 404.2563 $[M+H]^+$; found, 404.2544.

2-(4-(5-Chloro-3-(4,5-dihydropyrrolo[1,2-a]quinoxalin-4-yl)pyridin-2-yl)piperazin-1-yl)-N,N-dimethylethan-1-amine (62)

Compound 62 was prepared by following a procedure similar to that used to prepare compound 60, starting from 2,5-dichloronicotinaldehyde, N,N-dimethyl-2-(piperazin-1-yl)ethan-1-amine, and 2-(1H-pyrrol-1-yl)aniline. The title compound (32 mg, 37%) was obtained as a pale-yellow foam. $^1H$ NMR (300 MHz, $CDCl_3$) δ 8.22 (d, J=2.7 Hz, 1H), 7.66 (d, J=2.7 Hz, 1H), 7.37 (dd, J=7.8, 1.5 Hz, 1H), 7.24 (dd, J=3.0, 1.5 Hz, 1H), 6.98 (td, J=7.5, 1.5 Hz, 1H), 6.89 (td, J=7.8, 1.5 Hz, 1H), 6.73 (dd, J=7.8, 1.5 Hz, 1H), 6.31 (t, J=3.3 Hz, 1H), 5.77-5.74 (m, 2H), 4.57 (s, 1H), 3.40-3.33 (m, 2H), 3.15-3.08 (m, 2H), 2.71-2.44 (m, 8H), 2.27 (s, 6H). $^{13}C$ NMR (75 MHz, $CDCl_3$) δ 159.7, 146.2, 138.5, 136.1, 130.3, 128.0, 126.7, 125.7, 124.8, 119.8, 115.6, 115.1, 114.9, 110.2, 106.4, 56.9, 56.7, 53.7, 51.5, 50.4, 46.0. HRMS (ESI) calcd for $C_{24}H_{30}ClN_6$, 437.2220 $[M+H]^+$; found, 437.2209.

2-(4-(2-(4,5-Dihydropyrrolo[1,2-a]quinoxalin-4-yl) phenyl)piperazin-1-yl)-N,N-dimethylethan-1-amine (63)

Compound 63 was prepared by following a procedure similar to that used to prepare compound 60, starting from 2-fluorobenzaldehyde, N,N-dimethyl-2-(piperazin-1-yl) ethan-1-amine, and 2-(1H-pyrrol-1-yl)aniline. The title compound (44 mg, 55%) was obtained as a pale-yellow foam. $^1H$ NMR (300 MHz, $CDCl_3$) δ 7.36 (dd, J=7.8, 1.5 Hz, 1H), 7.28-7.21 (m, 4H), 7.06 (ddd, J=8.1, 6.9, 1.5 Hz, 1H), 6.94 (td, J=7.5, 1.5 Hz, 1H), 6.83 (td, J=7.5, 1.5 Hz, 1H), 6.67 (dd, J=7.8, 1.5 Hz, 1H), 6.32 (t, J=3.3 Hz, 1H), 6.06 (s, 1H), 5.76 (ddd, J=3.6, 1.5, 0.9 Hz, 1H), 4.80 (s, 1H), 3.24-3.17 (m, 2H), 2.96-2.89 (m, 2H), 2.67-2.46 (m, 8H), 2.29 (s, 6H). $^{13}C$ NMR (75 MHz, $CDCl_3$) δ 151.4, 137.1, 136.5, 129.6, 129.2, 128.8, 125.7, 124.8, 124.6, 120.5, 119.0, 115.4, 114.7, 114.4, 110.0, 105.8, 57.0, 56.7, 54.2, 53.5, 50.2, 46.0. HRMS (ESI) calcd for $C_{25}H_{32}N_5$, 402.2658 $[M+H]^+$; found, 402.2646.

1-(4-(2-(4-(2-(Dimethylamino)ethyl)piperazin-1-yl) pyridin-3-yl)pyrrolo[1,2-a]quinoxalin-5(4H)-yl) ethan-1-one (64)

To a solution of compound 38 (40 mg, 0.1 mmol) in 2 mL of $CH_2Cl_2$ was added acetyl chloride (12 mg, 0.15 mmol) and $Et_3N$ (21 mg, 0.2 mmol). The reaction mixture was stirred at RT for 30 min, and then evaporated in vacuo and purified by silica gel column chromatography ($CH_2Cl_2$/MeOH) to give compound 64 as a white foam (27 mg, 61%). $^1H$ NMR (300 MHz, $CD_3OD$) δ 8.07 (dd, J=4.5, 2.4 Hz, 1H), 7.63 (dd, J=8.1, 1.2 Hz, 1H), 7.53 (s, 1H), 7.44 (dd, J=3.0, 1.5 Hz, 1H), 7.34 (ddd, J=10.2, 7.5, 2.1 Hz, 2H), 7.13 (td, J=78, 1.2 Hz, 1H), 6.73-6.65 (m, 2H), 6.37 (t, J=3.3 Hz, 1H), 6.26 (dd, J=3.6, 1.5 Hz, 1H), 3.27-3.13 (m, 4H), 2.85-2.78 (m, 4H), 2.71-2.56 (m, 4H), 2.34 (s, 6H), 2.18 (s, 3H). $^{13}C$ NMR (75 MHz, $CD_3OD$) δ 170.5, 161.4, 147.1, 137.7, 131.6, 128.6, 128.5, 127.7, 127.5, 127.1, 124.0, 119.1, 115.9, 115.1, 110.5, 106.6, 55.8, 55.7, 53.4, 50.6, 44.5, 21.3. HRMS (ESI) calcd for $C_{26}H_{33}N_6O$, 445.2716 $[M+H]^+$; found, 445.2703.

N,N-Dimethyl-2-(4-(3-(pyrrolo[1,2-a]quinoxalin-4-yl)pyridin-2-yl)piperazin-1-yl)ethan-1-amine (65)

To a solution of 2-(4-(2-(dimethylamino)ethyl)piperazin-1-yl)nicotinaldehyde (32c) (53 mg, 0.2 mmol) and 2-(1H-pyrrol-1-yl)aniline (47 mg, 0.3 mmol) in EtOH (5 mL) was added 1 drop of AcOH. The reaction mixture was stirred at 70° C. overnight, and then evaporated in vacuo and purified by silica gel column chromatography ($CH_2Cl_2$/MeOH) to give compound 65 as a yellow solid (30 mg, 38%). $^1H$ NMR (300 MHz, $CDCl_3$) δ 8.36 (dd, J=4.8, 2.1 Hz, 1H), 8.08-7.98 (m, 2H), 7.93 (dd, J=8.1, 1.5 Hz, 1H), 7.82 (dd, J=7.5, 2.1 Hz, 1H), 7.61-7.48 (m, 2H), 6.94-6.84 (m, 2H), 6.78 (dd, J=4.2, 1.2 Hz, 1H), 3.32 (t, J=4.9 Hz, 4H), 2.46-2.09 (m, 15H). $^{13}C$ NMR (75 MHz, $CDCl_3$) δ 158.6, 154.5, 148.5, 140.1, 136.0, 130.1, 127.7, 127.1, 125.4, 124.7, 121.6, 114.8, 114.5, 113.9, 113.7, 109.1, 56.7, 53.4, 48.2, 45.8. HRMS (ESI) calcd for $C_{24}H_{29}N_6$, 401.2454 $[M+H]^+$; found, 401.2443.

2-(4-(3-(4H-Benzo[b]pyrrolo[1,2-d][1,4]oxazin-4-yl)pyridin-2-yl)piperazin-1-yl)-N,N-dimethylethan-1-amine (66)

To a solution of 2-aminophenol (500 mg, 4.6 mmol) in AcOH (7.5 mL) was added 2,5-dimethoxytetrahydrofuran (608 mg, 4.6 mmol) slowly. The mixture was stirred at 110° C. for 15 min, and then concentrated. 30 mL of $NaHCO_3$ (aq.) was added to the mixture. The resulting mixture was extracted with $CH_2Cl_2$ (3×50 mL), dried over $Na_2SO_4$, and concentrated. The residue was purified by silica gel column chromatography (Hex/EtOAc) to give 2-(1H-pyrrol-1-yl)phenol (59a) as brown oil (340 mg, 46%). $^1H$ NMR (300 MHz, $CDCl_3$) δ 7.30-7.20 (m, 2H), 7.06-6.93 (m, 2H), 6.85 (t, J=2.1 Hz, 2H), 6.39 (t, J=2.1 Hz, 2H), 5.28 (s, 1H).

To a solution of 2-(4-(2-(dimethylamino)ethyl)piperazin-1-yl)nicotinaldehyde (32c) (53 mg, 0.2 mmol) and compound 59a (32 mg, 0.2 mmol) in 2 mL of $CHCl_3$ was added TFA (23 mg, 0.2 mmol). The reaction mixture was stirred at 60° C. for 24 h, and then evaporated in vacuo and purified by silica gel column chromatography ($CH_2Cl_2$/MeOH) to give compound 66 as pale-yellow oil (37 mg, 46%). $^1H$ NMR (300 MHz, $CDCl_3$) δ 8.39 (dd, J=4.8, 1.8 Hz, 1H), 7.86 (dd, J=7.5, 1.8 Hz, 1H), 7.47-7.41 (m, 1H), 7.24 (dd, J=3.0, 1.5 Hz, 1H), 7.13-7.01 (m, 4H), 6.34-6.31 (m, 2H), 5.68 (dt, J=3.5, 1.2 Hz, 1H), 3.41-3.24 (m, 4H), 2.62-2.59 (m, 4H), 2.55-2.42 (m, 4H), 2.25 (s, 6H). $^{13}C$ NMR (75 MHz, $CDCl_3$) δ 161.9, 148.6, 146.5, 139.2, 127.7, 126.9, 125.1, 122.6, 118.4, 118.1, 115.4, 114.9, 110.7, 107.2, 107.2, 71.7, 56.9, 56.8, 53.7, 51.4, 46.0, 46.0. HRMS (ESI) calcd for $C_{24}H_{30}N_5O$, 404.2450 $[M+H]^+$; found, 404.2440.

(E Z)-N,N-Dimethyl-2-(4-(3-(((2-(2-methyl-1H-imidazol-1-yl)phenyl)imino)methyl)pyridin-2-yl)piperazin-1-yl)ethan-1-amine (67)

To a solution of 1-fluoro-2-nitrobenzene (423 mg, 3.0 mmol) and 2-methyl-1H-imidazole (246 mg, 3.0 mmol) in 20 mL of $CH_3CN$ was added $K_2CO_3$ (828 mg, 6.0 mmol). The reaction mixture was heated to reflux and stirred for 24 h, and then evaporated in vacuo and purified by silica gel column chromatography ($CH_2Cl_2$/hexane) to give 2-methyl-1-(2-nitrophenyl)-1H-imidazole (55) as pale-yellow oil (200 mg, 33%). $^1H$ NMR (300 MHz, $CDCl_3$) δ 8.07 (dd, J=8.1, 1.5 Hz, 1H), 7.77 (td, J=7.8, 1.5 Hz, 1H), 7.68 (td, J=7.8, 1.5 Hz, 1H), 7.45 (dd, J=7.8, 1.5 Hz, 1H), 7.08 (s, 1H), 6.93 (s, 1H), 2.24 (s, 3H).

To a solution of compound 55 (200 mg, 1.0 mmol) in 5 mL of EtOH was added 10% Pd/C (20 mg), the reaction mixture was stirred under hydrogen atmosphere for 4 h and then filtered and concentrated to afford 2-(2-methyl-1H-imidazol-1-yl)aniline (56) as pale-yellow oil (140 mg, 82%). $^1H$ NMR (300 MHz, $CDCl_3$) δ 7.25 (ddd, J=8.1, 7.5, 1.5 Hz, 1H), 7.09-7.05 (m, 2H), 6.93 (d, J=1.5 Hz, 1H), 6.86-6.78 (m, 2H), 3.61 (s, 2H), 2.25 (s, 3H).

To a solution of 2-(4-(2-(dimethylamino)ethyl)piperazin-1-yl)nicotinaldehyde (32c) (39 mg, 0.15 mmol) and compound 56 (39 mg, 0.23 mmol) in EtOH (4 mL) was added 2 drops of AcOH. The reaction mixture was stirred at 50° C. for 3 h, and then evaporated in vacuo and purified by silica gel column chromatography ($CH_2Cl_2$/MeOH) to give compound 67 as a pale-yellow foam (32 mg, 41%). $^1H$ NMR (300 MHz, $CDCl_3$) δ 8.48 (s, 1H), 8.31 (dd, J=4.8, 2.1 Hz, 1H), 7.96 (dd, J=7.5, 2.1 Hz, 1H), 7.53-7.47 (m, 1H), 7.34-7.31 (m, 2H), 7.12 (dt, J=7.8, 0.9 Hz, 1H), 7.00 (d, J=1.5 Hz, 1H), 6.93-6.89 (m, 2H), 3.32-3.29 (m, 4H), 2.66-2.50 (m, 8H), 2.32 (s, 6H), 2.25 (s, 3H). $^{13}C$ NMR (75 MHz, $CDCl_3$) δ 162.1, 159.1, 150.4, 148.3, 145.7, 137.5, 131.3, 129.9, 127.8, 127.4, 126.3, 121.4, 121.0, 119.2, 117.7, 56.7, 56.5, 53.6, 51.3, 45.8, 13.6. HRMS (ESI) calcd for $C_{24}H_{32}N_7$, 418.2719 $[M+H]^+$; found, 418.2707.

N,N-Dimethyl-2-(4-(3-(8-methyl-4H-benzo[b]pyrrolo[1,2-d][1,4]oxazin-4-yl)pyridin-2-yl)piperazin-1-yl)ethan-1-amine (68)

Compound 68 was prepared by following a procedure similar to that used to prepare compound 66, starting from 2-amino-p-cresol, 2,5-dimethoxytetrahydrofuran, and 2-(4-(2-(dimethylamino)ethyl)piperazin-1-yl)nicotinaldehyde (32c). The title compound (42 mg, 51%) was obtained as a pale-yellow foam. $^1H$ NMR (300 MHz, Chloroform-d) δ 8.39 (dd, J=4.8, 1.8 Hz, 1H), 7.85 (dd, J=7.5, 1.8 Hz, 1H), 7.25-7.21 (m, 2H), 7.03 (dd, J=7.5, 4.8 Hz, 1H), 6.94-6.88 (m, 2H), 6.32-6.29 (m, 2H), 5.68-5.66 (m, 1H), 3.40-3.23 (m, 4H), 2.62-2.43 (m, 8H), 2.40 (s, 3H), 2.26 (s, 6H). $^{13}C$ NMR (75 MHz, $CDCl_3$) δ 161.9, 148.6, 144.3, 139.2, 132.3, 127.8, 126.6, 125.6, 125.2, 118.4, 117.8, 115.4, 115.3, 110.5, 107.1, 71.7, 56.8, 56.7, 53.7, 51.4, 45.9, 21.0. HRMS (ESI) calcd for $C_{25}H_{32}N_5O$, 418.2607 $[M+H]^+$; found, 418.2597.

2-(4-(3-(8-Methoxy-4H-benzo[b]pyrrolo[1,2-d][1,4]oxazin-4-yl)pyridin-2-yl)piperazin-1-yl)-N,N-dimethylethan-1-amine (69)

Compound 69 was prepared by following a procedure similar to that used to prepare compound 66, starting from 2-amino-4-methoxyphenol, 2,5-dimethoxytetrahydrofuran, and 2-(4-(2-(dimethylamino)ethyl)piperazin-1-yl)nicotinaldehyde (32c). The title compound (55 mg, 64%) was obtained as a pale-yellow foam. $^1H$ NMR (300 MHz, Chloroform-d) δ 8.38 (dd, J=4.8, 1.8 Hz, 1H), 7.85 (dd, J=7.5, 1.8 Hz, 1H), 7.20 (dd, J=3.0, 1.5 Hz, 1H), 7.05-6.97 (m, 3H), 6.65 (dd, J=9.0, 2.7 Hz, 1H), 6.31 (t, J=3.0 Hz, 1H), 6.26 (s, 1H), 5.68 (dt, J=3.6, 1.2 Hz, 1H), 3.86 (s, 3H), 3.40-3.23 (m, 4H), 2.62-2.43 (m, 8H), 2.26 (s, 6H). $^{13}C$ NMR (75 MHz, $CDCl_3$) δ 161.9, 155.2, 148.6, 140.5, 139.2, 128.0, 127.4, 125.1, 118.5, 118.4, 115.4, 110.7, 109.6, 107.2, 101.5, 71.7, 56.8, 56.7, 55.9, 53.7, 51.4, 45.9. HRMS (ESI) calcd for $C_{25}H_{32}N_5O_2$, 434.2556 $[M+H]^+$; found, 434.2546.

2-(4-(3-(8-Fluoro-4H-benzo[b]pyrrolo[1,2-d][1,4]oxazin-4-yl)pyridin-2-yl)piperazin-1-yl)-N,N-dimethylethan-1-amine (70)

Compound 70 was prepared by following a procedure similar to that used to prepare compound 66, starting from 2-amino-4-fluorophenol, 2,5-dimethoxytetrahydrofuran, and 2-(4-(2-(dimethylamino)ethyl)piperazin-1-yl)nicotinaldehyde (32c). The title compound (26 mg, 30%) was obtained as a pale-yellow foam. $^1H$ NMR (300 MHz, Chloroform-d) δ 8.40 (dd, J=4.8, 1.8 Hz, 1H), 7.83 (dd, J=7.5, 1.8 Hz, 1H), 7.17-7.13 (m, 2H), 7.06-6.98 (m, 2H), 6.80 (td, J=8.7, 3.0 Hz, 1H), 6.34 (t, J=3.3 Hz, 1H), 6.29 (s, 1H), 5.70 (dt, J=3.6, 1.2 Hz, 1H), 3.40-3.22 (m, 4H), 2.63-2.43 (m, 8H), 2.26 (s, 6H). $^{13}C$ NMR (75 MHz, $CDCl_3$) δ 161.9, 159.7 (d, J=238.7 Hz), 148.7, 142.5 (d, J=2.7 Hz), 139.2, 127.7, 127.4 (d, J=10.8 Hz), 124.8, 118.9 (d, J=9.0 Hz), 118.5, 115.6, 111.3 (d, J=23.0 Hz), 111.2, 107.6, 102.6 (d, J=27.5 Hz), 71.8, 56.9, 56.7, 53.7, 51.4, 45.9. HRMS (ESI) calcd for $C_{24}H_{29}FN_5O$, 422.2356 $[M+H]^+$; found, 422.2344.

Methyl 4-(2-(4-(2-(dimethylamino)ethyl)piperazin-1-yl)pyridin-3-yl)-4H-benzo[b]pyrrolo[1,2-d][1,4]oxazine-7-carboxylate (71)

Methyl 3-hydroxy-4-(1H-pyrrol-1-yl)benzoate (59e) was synthesized as yellow oil (970 mg, 74%) by following a procedure similar to that used to prepare compound 59a, starting from methyl 4-amino-3-hydroxybenzoate and 2,5-dimethoxytetrahydrofuran. $^1$H NMR (300 MHz, $CDCl_3$) δ 7.79 (d, J=1.8 Hz, 1H), 7.66 (dd, J=8.3, 1.8 Hz, 1H), 7.31 (d, J=8.2 Hz, 1H), 6.99 (t, J=2.2 Hz, 2H), 6.41 (t, J=2.2 Hz, 2H), 6.11 (s, 1H), 3.94 (s, 3H).

The synthesis of compound 71 was conducted by following a procedure similar to that of compound 66, starting from compound 59e and 2-(4-(2-(dimethylamino)ethyl)piperazin-1-yl)nicotinaldehyde (32c). The title compound (38 mg, 42%) was obtained as a pale-yellow foam. $^1$H NMR (300 MHz, Chloroform-d) δ 8.40 (dd, J=4.8, 1.8 Hz, 1H), 7.83-7.78 (m, 2H), 7.73 (d, J=1.8 Hz, 1H), 7.47 (d, J=8.4 Hz, 1H), 7.26 (dd, J=3.0, 1.4 Hz, 1H), 7.03 (dd, J=7.5, 4.8 Hz, 1H), 6.37-6.35 (m, 2H), 5.73 (dt, J=3.6, 1.2 Hz, 1H), 3.92 (s, 3H), 3.42-3.22 (m, 4H), 2.63-2.43 (m, 8H), 2.26 (s, 6H). $^{13}$C NMR (75 MHz, $CDCl_3$) δ 166.2, 162.0, 148.8, 146.0, 139.2, 130.4, 127.7, 126.8, 124.8, 124.4, 119.6, 118.5, 115.8, 114.6, 111.7, 108.1, 71.9, 56.9, 56.7, 53.7, 52.2, 51.4, 45.9. HRMS (ESI) calcd for $C_{26}H_{32}N_5O_3$, 462.2505 $[M+H]^+$; found, 462.2496.

(4-(2-(4-(2-(Dimethylamino)ethyl)piperazin-1-yl)pyridin-3-yl)-4H-benzo[b]pyrrolo[1,2-d][1,4]oxazin-7-yl)methanol (72)

To a solution of compound 71 (46 mg, 0.1 mmol) in 2 mL of THF was added $LiAlH_4$ (8 mg, 0.2 mmol). The reaction mixture was stirred at RT for 2 h, and then quenched with ice water. The mixture was filtered, and then the solvent was evaporated in vacuo and purified by silica gel column chromatography ($CH_2Cl_2$/MeOH) to give compound 72 as pale-yellow oil (29 mg, 69%). $^1$H NMR (300 MHz, Chloroform-d) δ 8.39 (dd, J=4.8, 1.8 Hz, 1H), 7.83 (dd, J=7.5, 2.1 Hz, 1H), 7.42 (d, J=8.1 Hz, 1H), 7.23 (dd, J=3.0, 1.5 Hz, 1H), 7.12-7.08 (m, 2H), 7.03 (dd, J=7.5, 4.8 Hz, 1H), 6.33-6.31 (m, 2H), 5.68 (dt, J=3.5, 1.2 Hz, 1H), 3.40-3.24 (m, 4H), 2.60-2.43 (m, 8H), 2.25 (s, 6H). $^{13}$C NMR (75 MHz, $CDCl_3$) δ 161.9, 148.6, 146.5, 139.2, 138.4, 127.5, 126.2, 125.2, 121.1, 118.5, 116.7, 115.4, 114.9, 110.7, 107.2, 71.8, 64.7, 56.8, 56.7, 53.7, 51.4, 45.9. HRMS (ESI) calcd for $C_{25}H_{32}N_5O_2$, 434.2556 $[M+H]^+$; found, 434.2545.

4-(2-(4-(2-(Dimethylamino)ethyl)piperazin-1-yl)pyridin-3-yl)-4H-benzo[b]pyrrolo[1,2-d][1,4]oxazine-7-carboxamide (73)

To a solution of methyl 3-hydroxy-4-(1H-pyrrol-1-yl)benzoate (59e) (217 mg, 1.0 mmol) in 3 mL of EtOH was added LiOH monohydrate (210 mg, 5 mmol, in 3 mL of $H_2O$). The mixture was stirred at 50° C. for 4 h and then cooled to RT. The pH of the mixture was adjusted to ~7 with 1 M HCl (aq.). The mixture was extracted with EtOAc, dried over $Na_2SO_4$, and concentrated to give 3-hydroxy-4-(1H-pyrrol-1-yl)benzoic acid (195 mg, 96%) as a pale solid. To a solution of 3-hydroxy-4-(1H-pyrrol-1-yl)benzoic acid (102 mg, 0.5 mmol) and $NH_4Cl$ (133 mg, 2.5 mmol) in 5 mL of DMF was added HATU (210 mg, 0.55 mmol) and $Et_3N$ (101 mg, 1.0 mmol). The mixture was stirred at RT overnight. Then the mixture was diluted with EtOAc, washed with $H_2O$, dried over $Na_2SO_4$, and concentrated. The residue was purified by silica gel column chromatography to afford 3-hydroxy-4-(1H-pyrrol-1-yl)benzamide (59f) as a yellow solid (60 mg, 59%). $^1$H NMR (300 MHz, $CDCl_3$) δ 7.46-7.42 (m, 1H), 7.33-7.29 (m, 2H), 7.11 (t, J=2.2 Hz, 2H), 6.34 (t, J=2.2 Hz, 2H), 2.96 (s, 3H).

The synthesis of compound 73 was conducted by following a procedure similar to that of compound 66, starting from compound 59f and 2-(4-(2-(dimethylamino)ethyl)piperazin-1-yl)nicotinaldehyde (32c). The title compound (29 mg, 34%) was obtained as a pale-yellow foam. $^1$H NMR (300 MHz, $CDCl_3$) δ 8.40 (dd, J=4.8, 1.8 Hz, 1H), 7.81 (dd, J=7.5, 1.8 Hz, 1H), 7.61 (dd, J=8.4, 2.1 Hz, 1H), 7.51-7.47 (m, 2H), 7.26 (dd, J=3.0, 1.5 Hz, 1H), 7.04 (dd, J=7.5, 4.8 Hz, 1H), 6.38-6.36 (m, 2H), 5.99-5.72 (m, 3H), 3.39-3.22 (m, 4H), 2.61-2.47 (m, 8H), 2.26 (s, 6H). $^{13}$C NMR (75 MHz, $CDCl_3$) δ 168.0, 162.0, 148.9, 146.1, 139.2, 130.0, 129.7, 127.6, 124.8, 122.2, 118.5, 117.4, 115.7, 114.9, 111.7, 108.0, 71.9, 56.8, 56.7, 53.7, 51.4, 45.9. HRMS (ESI) calcd for $C_{25}H_{31}N_6O_2$, 447.2508 $[M+H]^+$; found, 447.2499.

4-(2-(4-(2-(dimethylamino)ethyl)piperazin-1-yl)pyridin-3-yl)-N-(2-(methylsulfonyl)ethyl)-4H-benzo[b]pyrrolo[1,2-d][1,4]oxazine-7-carboxamide (74)

Compound 74 was prepared as a pale-yellow foam by following a procedure similar to that used to prepare compound 73, starting from of methyl 3-hydroxy-4-(1H-pyrrol-1-yl)benzoate (59e), 2-(methylsulfonyl)ethanamine hydrochloride, and 2-(4-(2-(dimethylamino)ethyl)piperazin-1-yl)nicotinaldehyde (32c). $^1$H NMR (300 MHz, $CDCl_3$) δ 8.38 (dd, J=4.9, 1.9 Hz, 1H), 7.78 (dd, J=7.6, 1.8 Hz, 1H), 7.55-7.42 (m, 3H), 7.25-7.20 (m, 1H), 7.04-6.97 (m, 2H), 6.36-6.31 (m, 2H), 5.70 (d, J=3.8 Hz, 1H), 4.03-3.95 (m, 2H), 3.39-3.28 (m, 4H), 3.27-3.19 (m, 2H), 2.99 (s, 3H), 2.63-2.55 (m, 4H), 2.54-2.42 (m, 4H), 2.24 (s, 6H). $^{13}$C NMR (75 MHz, $CDCl_3$) δ 166.6, 162.1, 149.0, 146.4, 139.3, 130.5, 129.8, 127.8, 125.0, 121.8, 118.7, 117.3, 115.9, 115.0, 111.8, 108.2, 72.1, 57.0, 56.8, 54.0, 53.9, 51.6, 46.1, 41.8, 33.7. HRMS (ESI) calcd for $C_{28}H_{37}N_6O_4S$, 553.2597 $[M+H]^+$; found, 553.2586.

(4-(2-(4-(2-(Dimethylamino)ethyl)piperazin-1-yl)pyridin-3-yl)-4H-benzo[b]pyrrolo[1,2-d][1,4]oxazin-1-yl)methanol (75)

$POCl_3$ (23 mg, 0.15 mmol) was added dropwise to DMF (17 mg, 2.3 mmol) at 0° C. and stirred for another 20 min at 0° C. A solution of compound 66 (40 mg, 0.1 mmol) in DMF (1 mL) was added dropwise and the mixture was stirred at 50° C. overnight. Then the mixture was diluted with water (10 mL), extracted with $CH_2Cl_2$ (3×20 mL), dried over anhydrous $Na_2SO_4$, and concentrated. The residue was purified by silica gel chromatograph ($CH_2Cl_2$/MeOH) to give 4-(2-(4-(2-(dimethylamino)ethyl)piperazin-1-yl)pyridin-3-yl)-4H-benzo[b]pyrrolo[1,2-d][1,4]oxazine-1-carbaldehyde (38 mg, 88%) as a pale-yellow foam. $^1$H NMR (300 MHz, $CDCl_3$) δ 9.71 (s, 1H), 8.42-8.34 (m, 1H), 8.24-8.16 (m, 1H), 7.80-7.69 (m, 1H), 7.21-7.12 (m, 3H), 7.12-7.00 (m, 2H), 6.17 (s, 1H), 5.82 (d, J=4.1 Hz, 1H), 3.37-3.27 (m, 2H), 3.25-3.16 (m, 2H), 2.61-2.53 (m, 4H), 2.51-2.41 (m, 4H), 2.23 (s, 6H). $^{13}$C NMR (75 MHz, $CDCl_3$) δ 178.3, 162.1, 149.2, 147.7, 139.5, 139.1, 131.7, 128.0, 127.2, 126.5, 124.0, 123.1, 121.4, 118.7, 118.0, 108.5, 72.1, 56.9, 56.8, 53.7, 51.5, 46.0.

To a solution of compound 4-(2-(4-(2-(dimethylamino)ethyl)piperazin-1-yl)pyridin-3-yl)-4H-benzo[b]pyrrolo[1,2-d][1,4]oxazine-1-carbaldehyde (35 mg, 0.08 mmol) in 2 mL of dry EtOH was added $NaBH_4$ (7 mg, 0.16 mmol). The reaction mixture was stirred at RT for 6 h, and then quenched with ice water. The mixture was evaporated in vacuo and purified by silica gel column chromatography ($CH_2Cl_2$/MeOH) to give compound 75 as a pale white foam (30 mg, 85%). $^1H$ NMR (300 MHz, $CDCl_3$) δ 8.36 (dd, J=4.8, 2.0 Hz, 1H), 8.18-8.11 (m, 1H), 7.81 (dd, J=7.6, 1.9 Hz, 1H), 7.17-6.98 (m, 4H), 6.24 (d, J=3.6 Hz, 1H), 6.13 (s, 1H), 5.56 (d, J=3.6 Hz, 1H), 4.82 (d, J=13.1 Hz, 1H), 4.66 (d, J=13.1 Hz, 1H), 3.38-2.97 (m, 5H), 2.61-2.36 (m, 8H), 2.19 (s, 6H). $^{13}C$ NMR (75 MHz, $CDCl_3$) δ 161.7, 148.5, 147.7, 139.1, 131.2, 130.6, 127.4, 125.5, 124.8, 123.0, 118.5, 118.4, 118.0, 112.4, 105.8, 71.8, 56.8, 56.7, 56.5, 53.6, 51.3, 45.8. HRMS (ESI) calcd for $C_{25}H_{32}N_5O_2$, 434.2556 $[M+H]^+$; found, 434.2547.

N,N-Dimethyl-2-(4-(3-(1-(trifluoromethyl)-4H-benzo[b]pyrrolo[1,2-d][1,4]oxazin-4-yl)pyridin-2-yl)piperazin-1-yl)ethan-1-amine (76)

To a mixture of compound 66 (25 mg, 0.06 mmol) and $K_2CO_3$ (22 mg, 0.16 mmol) in 1 mL of DMF was added S-(trifluoromethyl)dibenzothiophenium triflate (120 mg, 0.30 mmol). The mixture was stirred at 80° C. for 48 h. Then the mixture was diluted with EtOAc, washed with $H_2O$, dried over anhydrous $Na_2SO_4$, and concentrated. The residue was purified by preparative TLC ($CH_2Cl_2$/MeOH) to afford compound 48 as a pale-yellow foam (6 mg, 21%). $^1H$ NMR (300 MHz, Chloroform-d) δ 8.42 (dd, J=4.8, 1.8 Hz, 1H), 7.87-7.76 (m, 2H), 7.25-7.06 (m, 4H), 6.79 (d, J=3.9 Hz, 1H), 6.15 (s, 1H), 5.70 (d, J=3.9 Hz, 1H), 3.35-3.20 (m, 4H), 2.60-2.48 (m, 8H), 2.29 (s, 6H). $^{13}C$ NMR (75 MHz, $CDCl_3$) δ 161.9, 148.9, 147.8, 139.0, 134.4, 134.4, 126.8, 126.4, 124.1, 123.1, 123.0, 119.9, 119.4, 118.6, 118.5, 118.4, 118.4, 118.4, 115.2, 115.1, 115.0, 115.0, 106.2, 71.7, 56.6, 56.4, 53.6, 51.4, 45.8. $^{19}F$ NMR (282 MHz, $CDCl_3$) δ −56.1. HRMS (ESI) calcd for $C_{25}H_{29}F_3N_5O$, 472.2324 $[M+H]^+$; found, 472.2313.

4.2 Cell Culture and Transfection

H1299, PLC/PRF/5 and HEK 293T cells were purchased from ATCC and cultured with DMEM supplemented with 10% FBS and 1% streptomycin-penicillin. BV2 cells were cultured with DMEM/F12 supplemented with 10% FBS, 2 mM Glutamine and 1% streptomycin-penicillin. R28 cells were cultured with DMEM supplemented with 10% calf serum, 2 mM Glutamine, 1% MEM non-essential amino acids, 1% MEM vitamin and 100 μg/mL Gentamicin. H1299 and PLC/PRF/5 cells were seeded in 6-well plates overnight and transfected with 20 nM control siRNA or Sirt6 siRNA (Dharmacon) by LIPOFECTAMINE RNA iMAX according to the manufacturer's instruction (Invitrogen). The knockdown efficiency of Sirt6 was verified by Western blot.

4.3. MTT Assay

R28 cells were seeded in 96 well plates at a density of $1\times10^4$/well overnight, then treated with compounds for 24 h. MTT (MilliporeSigma) was added to cells (20 μL/well) and incubated for 3.5 h. After medium was removed, 100 μL dimethyl sulfoxide (DMSO) was added into each well. Absorbance was measured at 540 nm using a microplate reader.

4.4. Sirt6 Sirt1/Sirt2 Sirt3 Activity Assay

Sirt6/Sirt1/Sirt2/Sirt3 activity was tested by Activity Assay Kits (Abcam) according to the manufacturer's instruction with minor modification. Briefly, compounds of indicated concentrations were added into the reaction system, 2.5 μL 10× buffer+2.5 μL Fluoro-substrate peptide (0.1 mM)+0.5 μL NAD+ (8 mM)+2.5 μL Developer+1 μL recombinant Sirt6/Sirt1/Sirt2/Sirt3, and the mixture was brought up to 25 μL with ddH2O. Fluorescence intensity was detected using a microplate reader at Ex/Em=490 nm/530 nm for Sirt6/Sirt2 activity or at Ex/Em=350 nm/450 nm for Sirt1/Sirt3 activity for 125 minutes. All experiments were conducted at room temperature.

Sirt5 Activity Assay

Sirt5 activity was tested by Fluorogenic Sirt5 Assay Kit (BPS Bioscience) according to the manufacturer's instruction. Briefly, 100 μM compounds were incubated with Sirt5 substrate, cosubstrate NAD+ and Sirt5 enzyme at 37° C. for 30 min, followed by incubation with Sirt Developer (containing Nicotinamide) at room temperature for 15 min. Fluorescence intensity was detected using a microplate reader at Ex/Em=350 nm/450 nm. The fold-change of Sirt5 activity in the presence of selected compounds was calculated as compared to vehicle group.

4.5. Molecular Docking Method

The molecular docking study was performed using SCHRODINGER SMALL-MOLECULE DRUG DISCOVERY SUITE (Schrödinger, LLC, New York, NY, 2020). Human Sirt6 in complex with an activator UBCS039 crystal structure (PDB ID: 5MF6) was downloaded from RCSB PDB bank [28]. The structure was prepared using Protein Preparation Wizard with default settings. During the preparation, hydrogens were added, crystal waters beyond 3 Å from existing ligand were removed, partial charges were assigned, and structure was minimized. 3D-structure of compound 38 (GL0710) was generated using Maestro and further prepared with LigPrep using OPLS3 forcefield. Compound 38 was ionized at target pH 7.4, desalted and tautomers were generated using Epik, and a low energy conformation was calculated. The grid box in size of 24 Å on each side was created with Glide. The grid center was chosen on the center of the existing ligand based on the binding site of crystal structure. Docking was employed with Glide using the SP protocol. Docked poses were incorporated into SCHRODINGER MAESTRO for a ligand-receptor interactions analysis. The final pose selected was among the best scoring poses. The selected pose was superimposed with Sirt6-UBCS039 complex structure for an overlay analysis.

4.6. Nucleosome Test

Nucleosome was extracted from HEK 293T cells with NUCLEOSOME PREPARATION KIT (Active Motif) according to the manufacturer's instruction. Briefly, HEK 293T cells in 100 mm dish were lysed with lysis buffer supplemented with PIC and PMSF for 30 min. After centrifugation for 10 min at 5000 rpm at 4° C., supernatant was removed and nuclei pellet was resuspended with digestion buffer supplemented with PIC and PMSF for 5 min at 37° C. Working enzymatic sharing cocktail was added to digest the chromatin, and EDTA was added after incubation to stop the digestion. Digested nucleosome was obtained in the supernatant after centrifugation for 10 min at 15000 rpm at 4° C. and the concentration was quantified by measuring the absorbance at 230 nm. 20 μg nucleosome was incubated in solution (1× buffer, 0.5 μL recombinant Sirt6 and 160 M NAD, from SIRT6 ACTIVITY ASSAY KIT) for 60 min. To test the effects of the compounds on Sirt6 activity, corresponding compound or DMSO control was added before incubation. The reaction mixture was analyzed by Western blot.

4.7. Western Blot

Proteins were extracted from cells with PIERCE RIPA BUFFER (89901, ThermoFisher Scientific), and protein concentration was determined using PIERCE BCA PROTEIN ASSAY KIT (23225, ThermoFisher Scientific). Equal amounts of protein were loaded and separated by SDS-PAGE gel. Next, separated proteins were transferred onto Nitrocellulose Blotting Membranes (A29457237, GE Healthcare Life science), and then the membranes were blocked by 5% non-fat dry milk. After incubation with corresponding primary antibodies against H3K9ac, H3 and Sirt6 at a 1:1000 dilution, or α-tubulin at a 1:5000 dilution, goat anti-mouse or goat anti-rabbit secondary antibodies at a 1:5000 dilution were applied. Finally, membranes were incubated with enhanced chemiluminescent and protein bands were detected by CHEMIDOC imaging system (Bio-Rad). Image-Lab software was used to analyze the intensities of the protein bands.

4.8. SARS-CoV-2-nluc Antiviral Assay

The antiviral activities were evaluated in A549-hACE2 cells using a protocol described previously [46]. In brief, 12,000 cells per well in phenol-red free medium containing 2% FBS were plated into a white opaque 96-well plate (Corning). On the next day, 2-fold serial dilutions of compounds were prepared in DMSO. The compounds were further diluted 100-fold in the phenol-red free culture medium containing 2% FBS. Cell culture fluids were removed and incubated with 50 μL of diluted compound solutions and 50 μL of SARS-CoV2-Nluc viruses (MOI 0.05). At 48 h post-infection, 50 μL Nano luciferase substrates (Promega) were added to each well. Luciferase signals were measured using a SYNERGY™ NEO 2 microplate reader. The relative luciferase signals were calculated by normalizing the luciferase signals of the compound-treated groups to that of the DMSO-treated groups (set as 100%). The relative luciferase signal (Y-axis) versus the log 10 values of compound concentration (X-axis) was plotted in software PRISM 9. The $EC_{50}$ (compound concentration for reducing 50% of luciferase signal) was calculated using a nonlinear regression model (four parameters). Two experiments were performed with technical duplicates.

4.9. Colony Formation Assay

H1299 and PLC/PRF/5 were seeded into 6-well plates and cultured for one week with or without indicated compounds treatment. After obvious colonies were formed, culture medium was removed, and colonies were fixed with 4% paraformaldehyde for 15 min and followed by staining with 1% crystal violet (C6158, Sigma-Aldrich) for 30 min at room temperature. After washing and drying, the stained colonies were photographed by CHEMIDOC IMAGING SYSTEM (Bio-Rad) and analyzed by IMAGE J.

It is to be understood that the foregoing descriptions are exemplary, and thus do not restrict the scope of the invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

[1] T. Finkel, C.-X. Deng, R. Mostoslavsky, Recent progress in the biology and physiology of sirtuins, Nature, 460 (2009) 587-591.

[2] F. Fiorentino, A. Mai, D. Rotili, Emerging therapeutic potential of SIRT6 modulators, J. Med. Chem., 64 (2021) 9732-9758.

[3] J. Du, Y. Zhou, X. Su, J. J. Yu, S. Khan, H. Jiang, J. Kim, J. Woo, J. H. Kim, B. H. Choi, B. He, W. Chen, S. Zhang, R. A. Cerione, J. Auwerx, Q. Hao, H. Lin, Sirt5 is a NAD-dependent protein lysine demalonylase and desuccinylase, Science, 334 (2011) 806-809.

[4] Johannes Gregor M. Rack, R. Morra, E. Barkauskaite, R. Kraehenbuehl, A. Ariza, Y. Qu, M. Ortmayer, O. Leidecker, David R. Cameron, I. Matic, Anton Y. Peleg, D. Leys, A. Traven, I. Ahel, Identification of a Class of Protein ADP-Ribosylating Sirtuins in Microbial Pathogens, Mol. Cell, 59 (2015) 309-320.

[5] G. Liu, H. Chen, H. Liu, W. Zhang, J. Zhou, Emerging roles of SIRT6 in human diseases and its modulators, Med. Res. Rev., 41 (2021) 1089-1137.

[6] A. A. Sauve, C. Wolberger, V. L. Schramm, J. D. Boeke, The biochemistry of sirtuins, Annu. Rev. Biochem., 75 (2006) 435-465.

[7] A. Chalkiadaki, L. Guarente, The multifaceted functions of sirtuins in cancer, Nat. Rev. Cancer, 15 (2015) 608-624.

[8] E. Michishita, R. A. McCord, E. Berber, M. Kioi, H. Padilla-Nash, M. Damian, P. Cheung, R. Kusumoto, T. L. A. Kawahara, J. C. Barrett, H. Y. Chang, V. A. Bohr, T. Ried, O. Gozani, K. F. Chua, SIRT6 is a histone H3 lysine 9 deacetylase that modulates telomeric chromatin, Nature, 452 (2008) 492-496.

[9] E. Michishita, R. A. McCord, L. D. Boxer, M. F. Barber, T. Hong, O. Gozani, K. F. Chua, Cell cycle-dependent deacetylation of telomeric histone H3 lysine K56 by human SIRT6, Cell Cycle, 8 (2009) 2664-2666.

[10] B. Yang, B. M. M. Zwaans, M. Eckersdorff, D. B. Lombard, The sirtuin SIRT6 deacetylates H3 K56Ac in vivo to promote genomic stability, Cell Cycle, 8 (2009) 2662-2663.

[11] L. Tasselli, Y. Xi, W. Zheng, R. I. Tennen, Z. Odrowaz, F. Simeoni, W. Li, K. F. Chua, SIRT6 deacetylates H3K18ac at pericentric chromatin to prevent mitotic errors and cellular senescence, Nat. Struct. Mol. Biol., 23 (2016) 434-440.

[12] Z. Mao, C. Hine, X. Tian, M. V. Meter, M. Au, A. Vaidya, A. Seluanov, V. Gorbunova, SIRT6 promotes DNA repair under stress by activating PARP1, Science, 332 (2011) 1443-1446.

[13] S. Kugel, R. Mostoslavsky, Chromatin and beyond: the multitasking roles for SIRT6, Trends Biochem. Sci., 39 (2014) 72-81.

[14] H. Jiang, S. Khan, Y. Wang, G. Charron, B. He, C. Sebastian, J. Du, R. Kim, E. Ge, R. Mostoslavsky, H. C. Hang, Q. Hao, H. Lin, SIRT6 regulates TNF-α secretion through hydrolysis of long-chain fatty acyl lysine, Nature, 496 (2013) 110-113.

[15] G. Liszt, E. Ford, M. Kurtev, L. Guarente, Mouse Sir2 homolog SIRT6 is a nuclear ADP-ribosyltransferase, J. Biol. Chem., 280 (2005) 21313-21320.

[16] R. Mostoslavsky, K. F. Chua, D. B. Lombard, W. W. Pang, M. R. Fischer, L. Gellon, P. Liu, G. Mostoslavsky, S. Franco, M. M. Murphy, K. D. Mills, P. Patel, J. T. Hsu, A. L. Hong, E. Ford, H.-L. Cheng, C. Kennedy, N. Nunez, R. Bronson, D. Frendewey, W. Auerbach, D. Valenzuela, M. Karow, M. O. Hottiger, S. Hursting, J. C. Barrett, L. Guarente, R. Mulligan, B. Demple, G. D. Yancopoulos, F. W. Alt, Genomic instability and aging-like phenotype in the absence of mammalian SIRT6, Cell, 124 (2006) 315-329.

[17] L. Tasselli, W. Zheng, K. F. Chua, Sirt6: Novel mechanisms and links to aging and disease, Trends Endocrinol. Metab., 28 (2017) 168-185.

[18] Y. Kanfi, S. Naiman, G. Amir, V. Peshti, G. Zinman, L. Nahum, Z. Bar-Joseph, H. Y. Cohen, The sirtuin SIRT6 regulates lifespan in male mice, Nature, 483 (2012) 218-221.

[19] C. Sebastián, Bernadette M. M. Zwaans, Dafne M. Silberman, M. Gymrek, A. Goren, L. Zhong, O. Ram, J. Truelove, Alexander R. Guimaraes, D. Toiber, C. Cosentino, Joel K. Greenson, Alasdair I. MacDonald, L. McGlynn, F. Maxwell, J. Edwards, S. Giacosa, E. Guccione, R. Weissleder, Bradley E. Bernstein, A. Regev, Paul G. Shiels, David B. Lombard, R. Mostoslavsky, The histone deacetylase SIRT6 is a tumor suppressor that controls cancer metabolism, Cell, 151 (2012) 1185-1199.

[20] E. Koyuncu, H. G. Budayeva, Y. V. Miteva, D. P. Ricci, T. J. Silhavy, T. Shenk, I. M. Cristea, D. E. Griffin, Sirtuins are evolutionarily conserved viral restriction factors, mBio, 5 (2014) e02249-02214.

[21] P. Li, Y. Jin, F. Qi, F. Wu, S. Luo, Y. Cheng, R. R. Montgomery, F. Qian, SIRT6 acts as a negative regulator in dengue virus-induced inflammatory response by targeting the DNA binding domain of NF-κB p65, Front. Cell. Infect. Microbiol., 8 (2018) 113.

[22] M. A. Klein, J. M. Denu, Biological and catalytic functions of sirtuin 6 as targets for small-molecule modulators, J. Biol. Chem., 295 (2020) 11021-11041.

[23] J. L. Feldman, J. Baeza, J. M. Denu, Activation of the protein deacetylase SIRT6 by long-chain fatty acids and widespread deacylation by mammalian sirtuins, J. Biol. Chem., 288 (2013) 31350-31356.

[24] M. Rahnasto-Rilla, T. Kokkola, E. Jarho, M. Lahtela-Kakkonen, R. Moaddel, N-acylethanolamines bind to SIRT6, ChemBioChem, 17 (2016) 77-81.

[25] W. You, W. Zheng, S. Weiss, K. F. Chua, C. Steegborn, Structural basis for the activation and inhibition of Sirtuin 6 by quercetin and its derivatives, Sci. Rep., 9 (2019) 19176.

[26] M. Rahnasto-Rilla, J. Tyni, M. Huovinen, E. Jarho, T. Kulikowicz, S. Ravichandran, V. A. Bohr, L. Ferrucci, M. Lahtela-Kakkonen, R. Moaddel, Natural polyphenols as sirtuin 6 modulators, Sci. Rep., 8 (2018) 4163.

[27] C. Jiang, Z. M. Sun, J. N. Hu, Y. Jin, Q. Guo, J. J. Xu, Z. X. Chen, R. H. Jiang, Y. S. Wu, Cyanidin ameliorates the progression of osteoarthritis via the Sirt6/NF-κB axis in vitro and in vivo, Food Funct, 10 (2019) 5873-5885.

[28] W. You, D. Rotili, T.-M. Li, C. Kambach, M. Meleshin, M. Schutkowski, K. F. Chua, A. Mai, C. Steegborn, Structural basis of Sirtuin 6 activation by synthetic small molecules, Angew. Chem. Int. Ed., 56 (2017) 1007-1011.

[29] M. A. Klein, C. Liu, V. I. Kuznetsov, J. B. Feltenberger, W. Tang, J. M. Denu, Mechanism of activation for the sirtuin 6 protein deacylase, J. Biol. Chem., 295 (2020) 1385-1399.

[30] Z. Huang, J. Zhao, W. Deng, Y. Chen, J. Shang, K. Song, L. Zhang, C. Wang, S. Lu, X. Yang, B. He, J. Min, H. Hu, M. Tan, J. Xu, Q. Zhang, J. Zhong, X. Sun, Z. Mao, H. Lin, M. Xiao, Y. E. Chin, H. Jiang, Y. Xu, G. Chen, J. Zhang, Identification of a cellularly active SIRT6 allosteric activator, Nat. Chem. Biol., 14 (2018) 1118-1126.

[31] J. Shang, Z. Zhu, Y. Chen, J. Song, Y. Huang, K. Song, J. Zhong, X. Xu, J. Wei, C. Wang, L. Cui, C. Y. Liu, J. Zhang, Small-molecule activating SIRT6 elicits therapeutic effects and synergistically promotes anti-tumor activity of vitamin D(3) in colorectal cancer, Theranostics, 10 (2020) 5845-5864.

[32] X. Chen, W. Sun, S. Huang, H. Zhang, G. Lin, H. Li, J. Qiao, L. Li, S. Yang, Discovery of potent small-molecule SIRT6 activators: Structure-activity relationship and anti-pancreatic ductal adenocarcinoma activity, J. Med. Chem., 63 (2020) 10474-10495.

[33] C. Schlicker, G. Boanca, M. Lakshminarasimhan, C. Steegborn, Structure-based development of novel sirtuin inhibitors, Aging, 3 (2011) 852-872.

[34] Z. G. Zhang, C. Y. Qin, Sirt6 suppresses hepatocellular carcinoma cell growth via inhibiting the extracellular signal-regulated kinase signaling pathway, Molecular medicine reports, 9 (2014) 882-888.

[35] Y. Wang, T. Pan, H. Wang, L. Li, J. Li, D. Zhang, H. Yang, Overexpression of SIRT6 attenuates the tumorigenicity of hepatocellular carcinoma cells, Oncotarget, 8 (2017) 76223-76230.

[36] Y. Cai, Z. Y. Sheng, S. X. Liang, Radiosensitization effect of overexpression of adenovirus-mediated SIRT6 on A549 non-small cell lung cancer cells, Asian Pac. J. Cancer Prev., 15 (2014) 7297-7301.

[37] Z. Han, L. Liu, Y. Liu, S. Li, Sirtuin SIRT6 suppresses cell proliferation through inhibition of Twist1 expression in non-small cell lung cancer, Int. J. Clin. Exp. Pathol., 7 (2014) 4774-4781.

[38] K. L. Mendes, D. d. F. Lelis, S. H. S. Santos, Nuclear sirtuins and inflammatory signaling pathways, Cytokine Growth Factor Rev., 38 (2017) 98-105.

[39] H. S. Lee, S. O. Ka, S. M. Lee, S. I. Lee, J. W. Park, B. H. Park, Overexpression of sirtuin 6 suppresses inflammatory responses and bone destruction in mice with collagen-induced arthritis, Arthritis. Rheum., 65 (2013) 1776-1785.

[40] K. L. Hou, S. K. Lin, L. H. Chao, E. Hsiang-Hua Lai, C. C. Chang, C. T. Shun, W. Y. Lu, J. H. Wang, M. Hsiao, C. Y. Hong, S. H. Kok, Sirtuin 6 suppresses hypoxia-induced inflammatory response in human osteoblasts via inhibition of reactive oxygen species production and glycolysis-A therapeutic implication in inflammatory bone resorption, Biofactors, 43 (2017) 170-180.

[41] T. L. A. Kawahara, E. Michishita, A. S. Adler, M. Damian, E. Berber, M. Lin, R. A. McCord, K. C. L. Ongaigui, L. D. Boxer, H. Y. Chang, K. F. Chua, SIRT6 links histone h3 lysine 9 deacetylation to NF-κB-dependent gene expression and organismal life span, Cell, 136 (2009) 62-74.

[42] E. Blasi, R. Barluzzi, V. Bocchini, R. Mazzolla, F. Bistoni, Immortalization of murine microglial cells by a v-raf/v-myc carrying retrovirus, J. Neuroimmunol., 27 (1990) 229-237.

[43] J. Xu, P.-Y. Shi, H. Li, J. Zhou, Broad spectrum antiviral agent niclosamide and its therapeutic potential, ACS Infect. Dis., 6 (2020) 909-915.

[44] J. Xu, Y. Xue, R. Zhou, P.-Y. Shi, H. Li, J. Zhou, Drug repurposing approach to combating coronavirus: Potential drugs and drug targets, Med. Res. Rev., 41 (2021) 1375-1426.

[45] S. K. Samrat, J. Xu, X. Xie, E. Gianti, H. Chen, J. Zou, J. G. Pattis, K. Elokely, H. Lee, Z. Li, M. L. Klein, P.-Y.

Shi, J. Zhou, H. Li, Allosteric inhibitors of the main protease of SARS-CoV-2, Antiviral Res., 205 (2022) 105381.

[46] X. Xie, A. E. Muruato, X. Zhang, K. G. Lokugamage, C. R. Fontes-Garfias, J. Zou, J. Liu, P. Ren, M. Balakrishnan, T. Cihlar, C.-T. K. Tseng, S. Makino, V. D. Menachery, J. P. Bilello, P.-Y. Shi, A nanoluciferase SARS-CoV-2 for rapid neutralization testing and screening of anti-infective drugs for COVID-19, Nat. Commun., 11 (2020) 5214.

All publications mentioned herein are incorporated by reference to the extent they support the present invention.

We claim:

1. A compound according to Formula (I):

Formula (I)

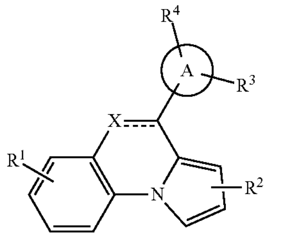

or a pharmaceutically acceptable salt, tautomer, or isotopologue thereof, wherein:

$\overset{----}{----}$ represents a single or double bond;

X is $NR^5$ or N or O or C;

$R^5$ is chosen from hydrogen, alkyl, cycloalkyl, alkoxyalkyl, alkylcarbonyl, or alkylsulfonyl;

A is a five to ten membered ring chosen from heteroaryl, or fused heteroaryl;

$R^1$, $R^2$, $R^4$ are independently chosen from hydrogen, alkyl, cycloalkyl, haloalkyl, haloalkoxy, alkoxy, halo, cyano, carboxy, alkoxycarbonyl-$R^8$, alkylcarbonyl-$R^8$, aminocarbonyl, alkylaminocarbonyl-$R^8$, alkoxyalkyl, aminoalkyl, aminoalkoxy, hydroxyl, and hydroxyalkyl;

$R^3$ is a four to eight membered heterocycle, substituted with one or more $R^6$ substituents;

$R^6$ is chosen from hydrogen, hydroxyl, halo, alkyl-$R^7$, alkoxy, cycloalkyl, carbonyl-$R^7$, alkylcarbonyl-$R^7$, alkylsulfonyl, heteroaryl, or heterocyclyl; wherein $R^7$ is chosen from hydrogen, hydroxyl, halo, alkoxy, amino, cyano, alkylamino, dialkylamino, aminocarbonyl, alkylaminocarbonyl, dialkylaminocarbonyl, heterocyclyl, or heteroaryl; wherein $R^7$ is chosen from hydrogen, halo, hydroxyl, cycloalkyl, alkoxy, or alklysulfonyl.

2. The compound of claim 1, wherein X is $NR^5$ or N or O.

3. The compound of claim 2, wherein $R^5$ is hydrogen, or alkylcarbonyl.

4. The compound of claim 1, wherein $R^2$ is hydrogen, $CF_3$, or $CH_2OH$.

5. The compound of claim 1, wherein A is aryl, pyrazinyl, or pyridyl.

6. The compound of claim 1, wherein $R^4$ is hydrogen or halo.

7. The compound of claim 1, wherein the heterocycle in $R^3$ is chosen from piperazine, morpholine, piperidine, pyrrolidine, and azetidine.

8. The compound of claim 1, wherein $R^6$ is chosen from hydrogen, acetyl, methane sulfonyl, halo, pyridyl, methyl, hydroxyl, hydroxyalkyl, N,N-dimethylaminoalkyl, alkoxyalkyl, $CH_2C(O)N(Me)_2$, pyrrolidon-1-yl, urea, cyanoalkyl, chloromethylacetyl, 2-(imidazol-1-yl)-ethyl, and 2-(morpholin-4-yl)-ethyl.

9. A compound chosen from any of the following structures:

| Cpd No. | Structure |
|---|---|
| 21 | 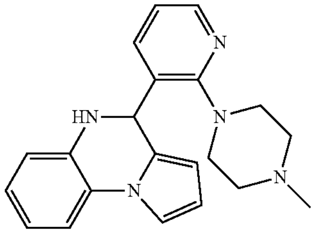 [SMILES: CN1CCN(c2ncccc2C2Nc3ccccc3-n3cccc32)CC1] |
| 30 | 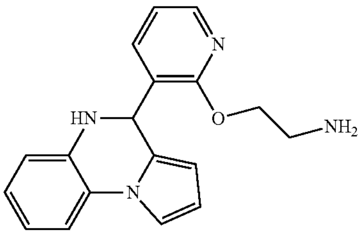 [SMILES: NCCOc1ncccc1C1Nc2ccccc2-n2cccc21] |

-continued
| Cpd No. | Structure |
| --- | --- |
| 22 | 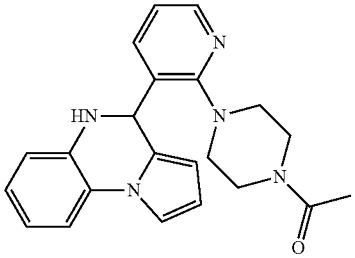 [SMILES: CC(=O)N1CCN(c2ncccc2C2Nc3ccccc3-n3cccc32)CC1] |
| 23 | 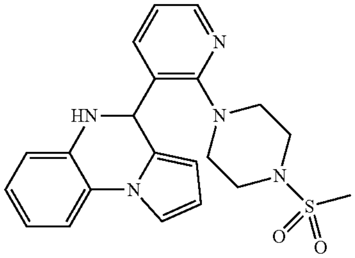 [SMILES: CS(=O)(=O)N1CCN(c2ncccc2C2Nc3ccccc3-n3cccc32)CC1] |
| 24 | 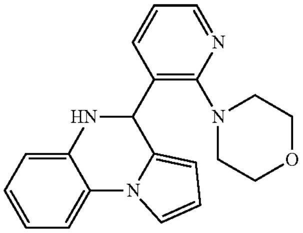 [SMILES: c1ccc2c(c1)NC(c1cccnc1N1CCOCC1)c1cccn1-2] |
| 25 | 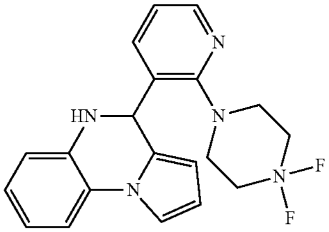 |
| 18 | 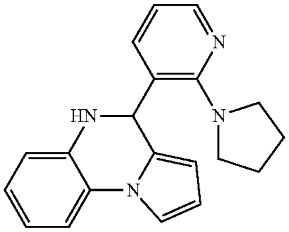 [SMILES: c1ccc2c(c1)NC(c1cccnc1N1CCCC1)c1cccn1-2] |
| 28 | 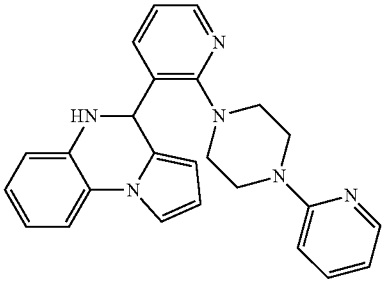 [SMILES: c1ccc(N2CCN(c3ncccc3C3Nc4ccccc4-n4cccc43)CC2)nc1] |

-continued
| Cpd No. | Structure |
|---|---|
| 29 | 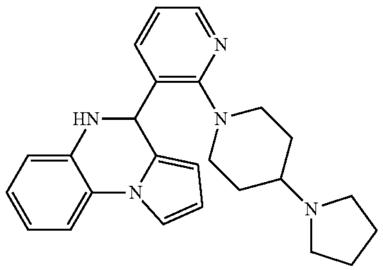 [SMILES: c1ccc2c(c1)NC(c1cccnc1N1CCC(N3CCCC3)CC1)c1cccn1-2] |
| 16 | 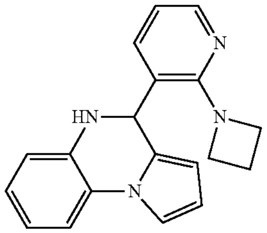 [SMILES: c1ccc2c(c1)NC(c1cccnc1N1CCC1)c1cccn1-2] |
| 19 | 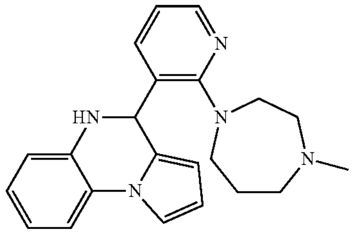 [SMILES: CN1CCCN(c2ncccc2C2Nc3ccccc3-n3cccc32)CC1] |
| 26 | 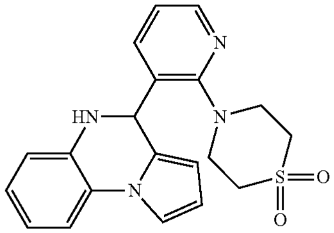 [SMILES: O=S1(=O)CCN(c2ncccc2C2Nc3ccccc3-n3cccc32)CC1] |
| 20 | 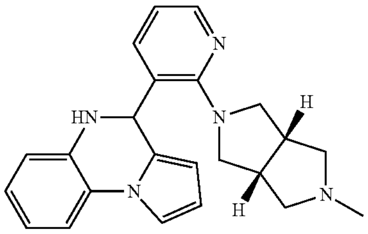 [SMILES: CN1C[C@@H]2CN(c3ncccc3C3Nc4ccccc4-n4cccc43)C[C@@H]2C1] |
| 27 | 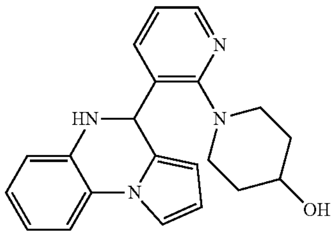 [SMILES: OC1CCN(c2ncccc2C2Nc3ccccc3-n3cccc32)CC1] |

-continued
| Cpd No. | Structure |
| --- | --- |
| 17 | 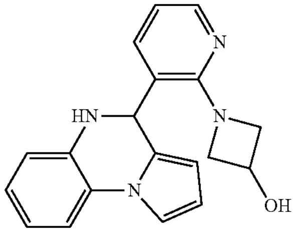 [SMILES: OC1CN(c2ncccc2C2Nc3ccccc3-n3cccc32)C1] |
| 35 | 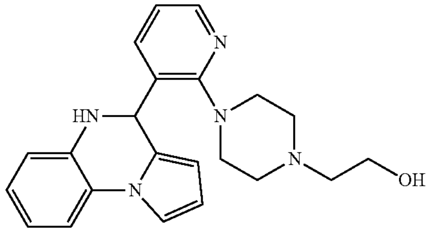 [SMILES: OCCN1CCN(c2ncccc2C2Nc3ccccc3-n3cccc32)CC1] |
| 38 | 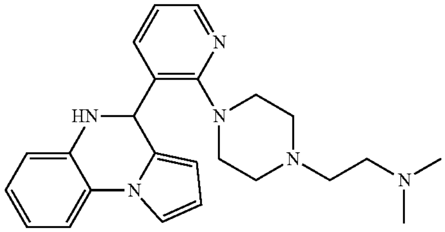 [SMILES: CN(C)CCN1CCN(c2ncccc2C2Nc3ccccc3-n3cccc32)CC1] |
| 36 | 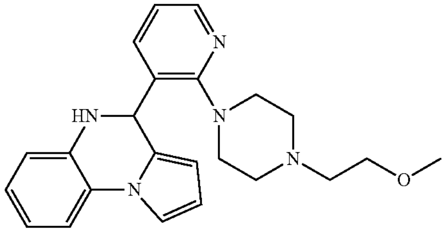 [SMILES: COCCN1CCN(c2ncccc2C2Nc3ccccc3-n3cccc32)CC1] |
| 65 | 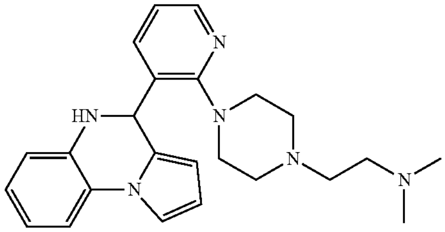 [SMILES: CN(C)CCN1CCN(c2ncccc2C2Nc3ccccc3-n3cccc32)CC1] |
| 37 | 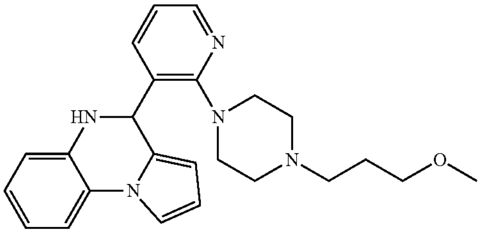 [SMILES: COCCCN1CCN(c2ncccc2C2Nc3ccccc3-n3cccc32)CC1] |

-continued
| Cpd No. | Structure |
| --- | --- |
| 39 | 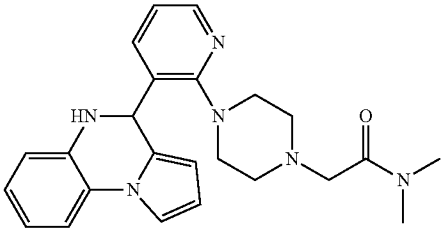 [SMILES: CN(C)C(=O)CN1CCN(c2ncccc2C2Nc3ccccc3-n3cccc32)CC1] |
| 48 | 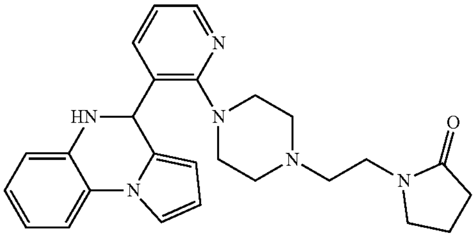 [SMILES: O=C1CCCN1CCN1CCN(c2ncccc2C2Nc3ccccc3-n3cccc32)CC1] |
| 44 | 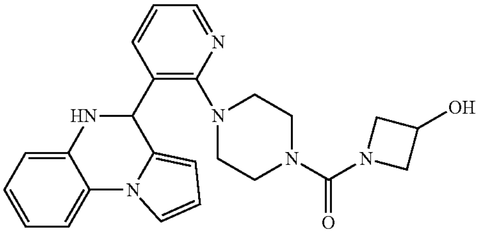 [SMILES: O=C(N1CCN(c2ncccc2C2Nc3ccccc3-n3cccc32)CC1)N1CC(O)C1] |
| 40 | 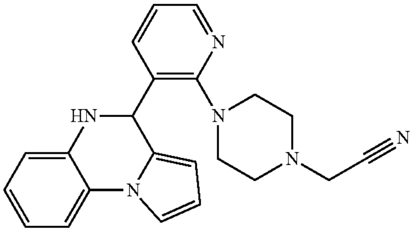 [SMILES: N#CCN1CCN(c2ncccc2C2Nc3ccccc3-n3cccc32)CC1] |
| 41 | 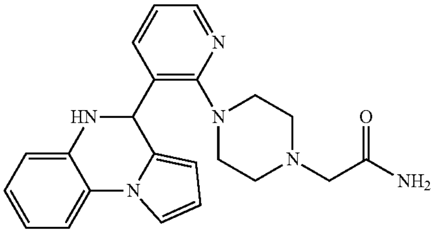 [SMILES: NC(=O)CN1CCN(c2ncccc2C2Nc3ccccc3-n3cccc32)CC1] |
| 42 | 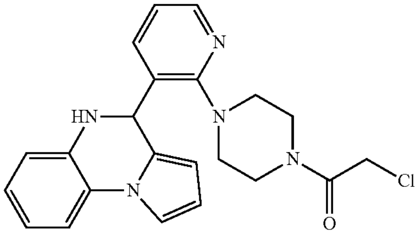 [SMILES: O=C(CCl)N1CCN(c2ncccc2C2Nc3ccccc3-n3cccc32)CC1] |

-continued
| Cpd No. | Structure |
|---|---|
| 43 | 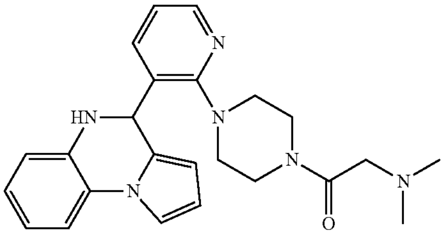 [SMILES: CN(C)CC(=O)N1CCN(c2ncccc2C2Nc3ccccc3-n3cccc32)CC1] |
| 45 | 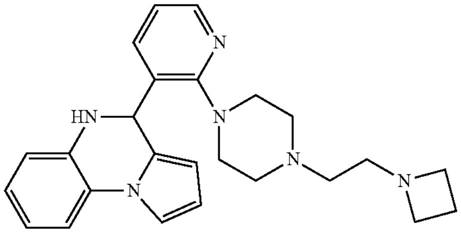 [SMILES: c1ccc2c(c1)NC(c1cccnc1N1CCN(CCN3CCC3)CC1)c1cccn1-2] |
| 46 | 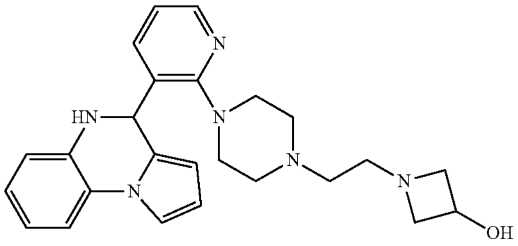 [SMILES: OC1CN(CCN2CCN(c3ncccc3C3Nc4ccccc4-n4cccc43)CC2)C1] |
| 50 | 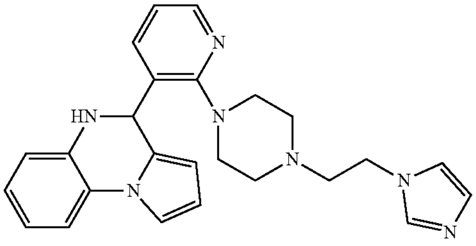 [SMILES: c1ccc2c(c1)NC(c1cccnc1N1CCN(CCn3ccnc3)CC1)c1cccn1-2] |
| 47 | 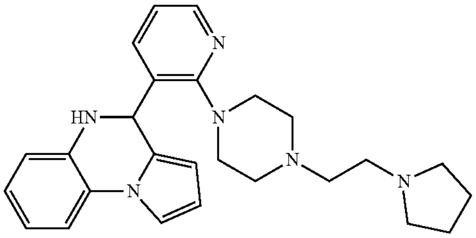 [SMILES: c1ccc2c(c1)NC(c1cccnc1N1CCN(CCN3CCCC3)CC1)c1cccn1-2] |
| 49 | 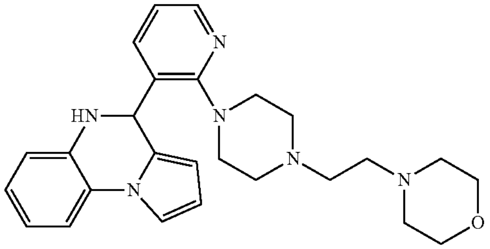 [SMILES: c1ccc2c(c1)NC(c1cccnc1N1CCN(CCN3CCOCC3)CC1)c1cccn1-2] |

-continued
| Cpd No. | Structure |
| --- | --- |
| 64 | 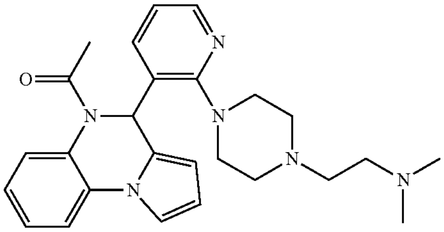 [SMILES: CC(=O)N1c2ccccc2-n2cccc2C1c1cccnc1N1CCN(CCN(C)C)CC1] |
| 60 | 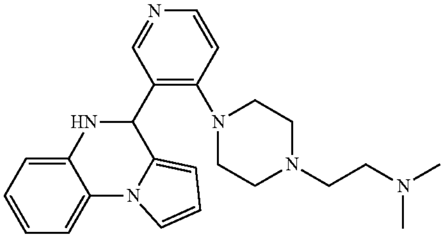 [SMILES: CN(C)CCN1CCN(c2ccncc2C2Nc3ccccc3-n3cccc32)CC1] |
| 62 | 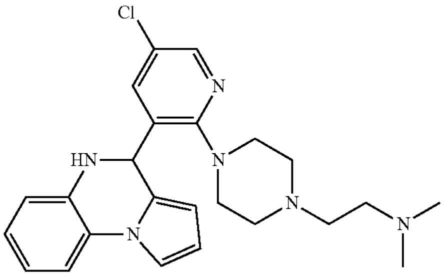 [SMILES: CN(C)CCN1CCN(c2ncc(Cl)cc2C2Nc3ccccc3-n3cccc32)CC1] |
| 61 | 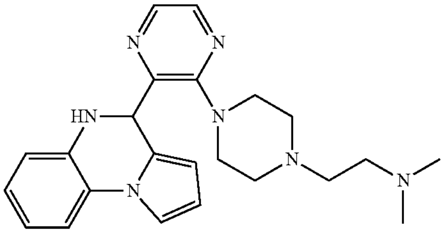 |
| 66 | 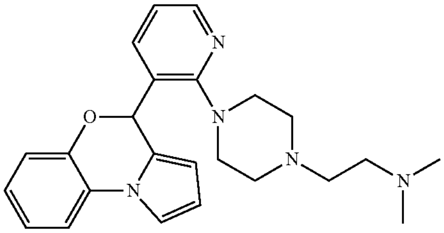 [SMILES: CN(C)CCN1CCN(c2ncccc2C2Oc3ccccc3-n3cccc32)CC1] |
| 68 | 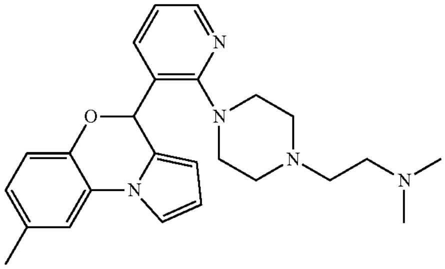 [SMILES: Cc1ccc2c(c1)-n1cccc1C(c1cccnc1N1CCN(CCN(C)C)CC1)O2] |

-continued
| Cpd No. | Structure |
|---|---|
| 70 | 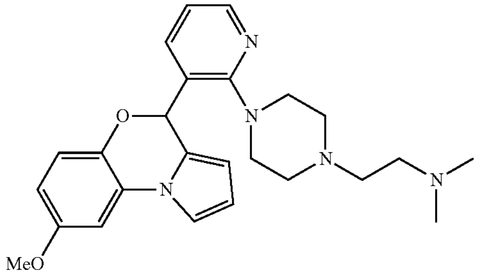 [SMILES: COc1ccc2c(c1)-n1cccc1C(c1cccnc1N1CCN(CCN(C)C)CC1)O2] |
| 69 | 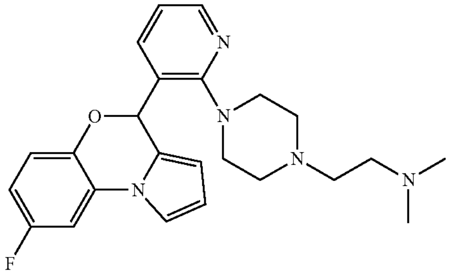 [SMILES: CN(C)CCN1CCN(c2ncccc2C2Oc3ccc(F)cc3-n3cccc32)CC1] |
| 73 | 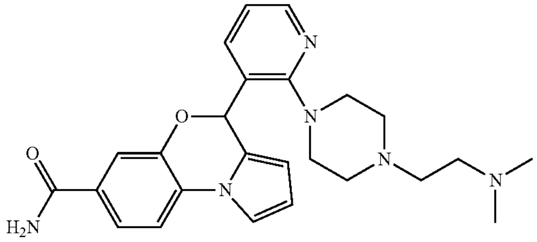 [SMILES: CN(C)CCN1CCN(c2ncccc2C2Oc3cc(C(N)=O)ccc3-n3cccc32)CC1] |
| 71 | 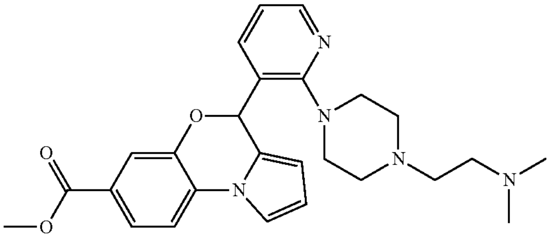 |
| 72 | 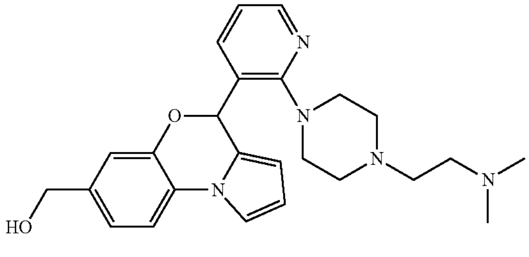 [SMILES: CN(C)CCN1CCN(c2ncccc2C2Oc3cc(CO)ccc3-n3cccc32)CC1] |

-continued
| Cpd No. | Structure |
|---|---|
| 74 | 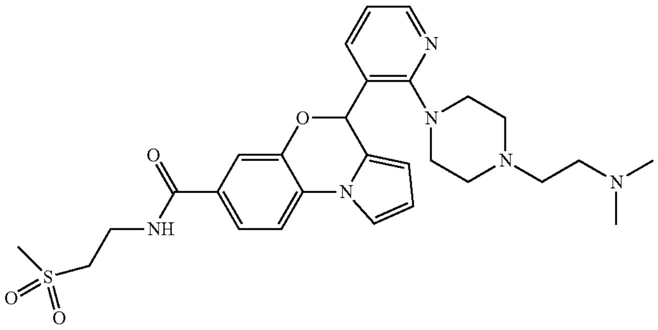 [SMILES: CN(C)CCN1CCN(c2ncccc2C2Oc3cc(C(=O)NCCS(C)(=O)=O)ccc3-n3cccc32)CC1] |
| 76 | 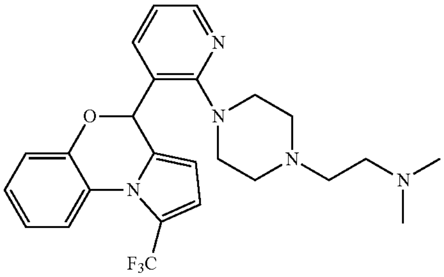 [SMILES: CN(C)CCN1CCN(c2ncccc2C2Oc3ccccc3-n3c2ccc3C(F)(F)F)CC1] |
| 75 | 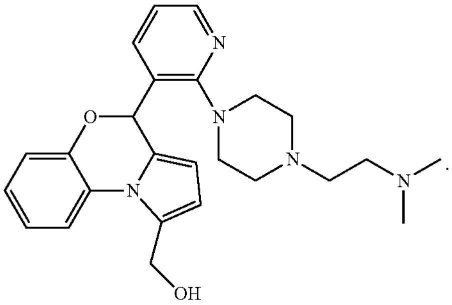 [SMILES: CN(C)CCN1CCN(c2ncccc2C2Oc3ccccc3-n3c(CO)ccc32)CC1] |
10. The compound of claim 1, wherein the compound of Formula (I) is:
Compound 35
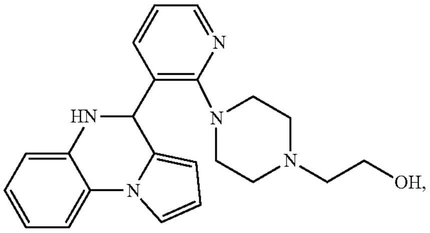
-continued
Compound 36
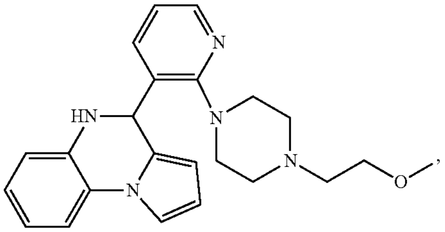
Compound 38
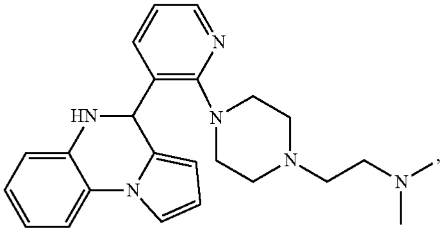

-continued
Compound 46
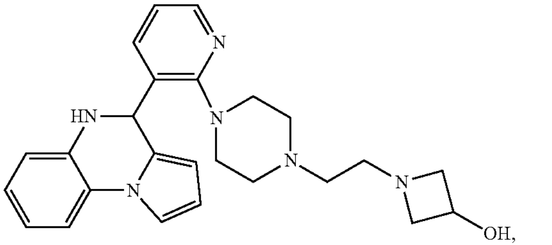
OH,
Compound 47
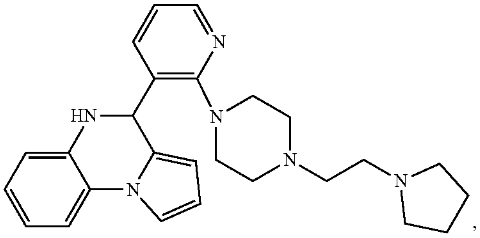
, or
-continued
Compound 50
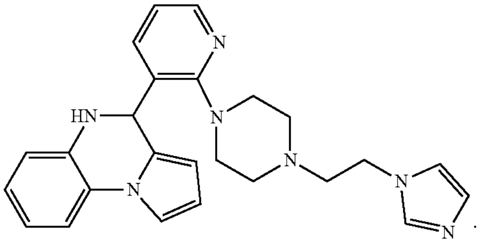
.
* * * * *